US010414864B2

(12) United States Patent
Becker et al.

(10) Patent No.: US 10,414,864 B2
(45) Date of Patent: Sep. 17, 2019

(54) DEGRADABLE AMINO ACID-BASED POLY (ESTER UREA) COPOLYMER ADHESIVES

(71) Applicant: THE UNIVERSITY OF AKRON, Akron, OH (US)

(72) Inventors: Matthew Becker, Stow, OH (US); Jinjun Zhou, Akron, OH (US); Adrian Defante, Parma Heights, OH (US); Ali Dhinojwala, Akron, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 61 days.

(21) Appl. No.: 15/328,983

(22) PCT Filed: Jul. 21, 2015

(86) PCT No.: PCT/US2015/041259
§ 371 (c)(1),
(2) Date: Jan. 25, 2017

(87) PCT Pub. No.: WO2016/014471
PCT Pub. Date: Jan. 28, 2016

(65) Prior Publication Data

US 2017/0210852 A1 Jul. 27, 2017

Related U.S. Application Data

(60) Provisional application No. 62/027,487, filed on Jul. 22, 2014.

(51) Int. Cl.

| | |
|---|---|
| ***C08G 71/00*** | (2006.01) |
| ***A61K 9/00*** | (2006.01) |

(Continued)

(52) U.S. Cl.
CPC ............ *C08G 71/02* (2013.01); *A61K 8/0204* (2013.01); *A61K 8/84* (2013.01); *A61K 8/85* (2013.01);
(Continued)

(58) Field of Classification Search
CPC .......... A61K 8/84; A61K 8/85; A61K 9/0014; A61K 47/34; A61L 26/0019; C09J 175/02; C08G 71/02
See application file for complete search history.

(56) References Cited

U.S. PATENT DOCUMENTS

| | | | | |
|---|---|---|---|---|
| 2007/0299155 A1* | 12/2007 | Carpenter | C08L 77/12 | 523/105 |
| 2008/0139746 A1* | 6/2008 | Pacetti | A61L 27/34 | 525/188 |

(Continued)

OTHER PUBLICATIONS

"Synthesis of new poly(ether—urethane—urea)s based on amino acid cyclopeptide and PEG: study of their environmental degradation" Amino Acids (2013) 44:449-459. Rafiemanzelat et al.*

*Primary Examiner* — Michael L Leonard
(74) *Attorney, Agent, or Firm* — Renner Kenner Greive Bobak Taylor & Weber

(57) ABSTRACT

The present invention is directed to a novel group of amino acid-based poly(ester urea)s (PEUs) for use in biodegradable adhesive and related methods for their making and use. These novel amino acid-based PEUs have a wide variation in mechanical properties and degradation behavior that can be tuned by varying the amino acids and polyols used to form the polyester monomers that form the PEUs. Importantly, these novel PEUs have been shown to be non-toxic in vitro and in vivo and may be suitable to a wide variety of biomedical and other uses. In some embodiments, the adhesive properties of these degradable amino acid-based poly (ester urea) adhesives has been further improved by the
(Continued)

incorporation of controlled amounts of catechol functional groups into the side chains of the PEU via post-polymerization functionalization chemistry.

21 Claims, 13 Drawing Sheets

(51) Int. Cl.

| | |
|---|---|
| ***C08G 71/02*** | (2006.01) |
| ***A61K 47/34*** | (2017.01) |
| ***A61K 8/84*** | (2006.01) |
| ***A61L 26/00*** | (2006.01) |
| ***A61Q 19/00*** | (2006.01) |
| ***C09J 175/02*** | (2006.01) |
| ***A61Q 1/02*** | (2006.01) |
| ***A61K 8/85*** | (2006.01) |
| ***A61K 8/02*** | (2006.01) |

(52) U.S. Cl.
CPC ............ *A61K 9/0014* (2013.01); *A61K 47/34* (2013.01); *A61L 26/0019* (2013.01); *A61Q 1/025* (2013.01); *A61Q 19/00* (2013.01); *C09J 175/02* (2013.01); *A61K 2800/10* (2013.01)

(56) References Cited

U.S. PATENT DOCUMENTS

2008/0171836 A1* 7/2008 Lee .................. C08G 65/33389
525/418
2013/0053594 A1* 2/2013 Lee ...................... C08G 65/329
556/56

* cited by examiner

DEGRADABLE AMINO ACID-BASED POLY (ESTER UREA) COPOLYMER ADHESIVES

CROSS REFERENCE TO RELATED APPLICATIONS

This application claims the benefit of U.S. provisional patent application Ser. No. 62/027,487 entitled “Degradable Amino Acid-Based Poly(ester urea) Copolymer Adhesives,” filed Jul. 22, 2014, and incorporated herein by reference in its entirety.

REFERENCE TO GOVERNMENT SUPPORT

This invention was made with government support under grant number DMR-1105370 awarded by U.S. National Science Foundation. The government has certain rights in the invention.

FIELD OF THE INVENTION

One or more embodiments of the present invention relate to degradable amino acid-based poly(ester urea) adhesives. In certain embodiments, the present invention relates to degradable amino acid-based poly(ester urea) adhesives having phenylalanine, tyrosine and/or catechol functional groups.

BACKGROUND OF THE INVENTION

Marine organisms, such as mussels, provide examples of strong adhesive systems that have not been mimicked well by human technology. Barnacles and marine mussels are able to affix themselves to virtually all types of surfaces, including metals, rocks and even polytetrafluoroethylene (PTFE, TEFLON™). They are capable of securing themselves over wide temperature range (−40 to 40° C.), fluctuating salinities, humidity and in the currents of marine environments. Mussel adhesive proteins have been isolated and sequenced. These proteins are rich in the unusual amino acid 3,4-dihydroxyphenylalanine (DOPA), which is believed to be critical for the formation of adhesive surface bonding and cohesive cross-links. The surface adhesion could originate from metal chelation, hydrogen bonding or radical-surface coupling provided by the catechol moiety in DOPA. Bulk cohesive strength has been found to be a result of oxidative cross-linking or metal chelation of DOPA. Various types of polymers carrying catechol groups have been prepared to investigate the nature of catechol functional group and to develop adhesives for specialty applications. Synthetic polymers incorporating DOPA-like chemistry have been explored with polypeptides, polyacrylates, poly(ethylene glycol)s, and polystyrene based systems. These materials, however, lacked the adhesion, elasticity, and/or degredation properties necessary for a soft tissue adhesive.

One intriguing application of these synthetic biomimetic materials is to provide the next generation of surgical adhesives and orthopedic cements. All surgical patients require a proper wound closure procedure to enable healing. Though devices such as sutures and staples have been used for many years, they are somewhat invasive and there are many potential sources of infection and inflammation of the wound area associated with these methods. Less invasive methods are continually explored in an effort to find optimal tissue adhesives. Cyanoacrylate based synthetic glues have been used as topical skin adhesives because they polymerize rapidly upon contact with water or blood. However, a limitation of these materials is moisture sensitivity and carcinogenic degradation byproducts. Another commercially available tissue adhesive is based on fibrin. Although this fibrin-based glue is made from human serum and is non-toxic, it is limited by poor mechanical strength. The ideal tissue adhesive design should incorporate simplicity, safety, efficacy, and possess setting times tailored for the specific clinical application. For commercial applications they should ideally be inexpensive, painless and cosmetic. Catechol-functionalized hydrogels have been developed as potential tissue adhesives and hemostatic materials. However, most of these adhesive materials lack tunability of elastic modulus and degradation rates for specific biomedical applications.

What is needed in the art is an inexpensive, painless and cosmetic adhesive design that incorporates simplicity, safety, and efficacy; mechanical strength; setting times tailored for specific clinical applications; and tunable elastic modulus and degradation rates for specific biomedical applications.

SUMMARY OF THE INVENTION

One or more embodiments of the present invention provide an inexpensive, painless and cosmetic adhesive design that incorporates simplicity, safety, efficacy, and possesses setting times tailored for the specific clinical applications and tunability of elastic modulus and degradation rates for specific biomedical applications. The poly(ester urea)s (PEUs) of various embodiments of the present invention have a wide variation in mechanical properties and degradation behavior that can be tuned by varying the amino acids and diols used to form the PEU. Importantly the PEUs of the present invention have been shown to be non-toxic in vitro and in vivo. In one or more embodiments, the present invention is directed to a degradable amino acid-based poly(ester urea) adhesive having controlled amounts of catechol groups incorporated into side chains of the PEU. In some embodiments, these catechol groups may be introduced via post-polymerization functionalization chemistry.

In a first aspect, the present invention is directed to a biodegradable adhesive comprising an amino acid-based poly(ester urea). In some embodiments, the amino acid-based poly(ester urea) adhesive of the present invention comprises a residue of phenylalanine or tyrosine. In one or more embodiments, the amino acid-based poly(ester urea) adhesive of the present invention includes any one or more of the above referenced embodiments of the first aspect of the present invention comprises one or more catechol functional groups.

In one or more embodiments, the amino acid-based poly (ester urea) adhesive of the present invention includes any one or more of the above referenced embodiments of the first aspect of the present invention wherein the amino acid-based poly(ester urea) further comprises two or more monomer segments; the two or more monomer segments comprising the residue of two or more amino acids separated by from 2 to 20 carbon atoms. In one or more embodiments, the amino acid-based poly(ester urea) adhesive of the present invention includes any one or more of the above referenced embodiments of the first aspect of the present invention wherein the two or more amino acids in the two or more monomer segments are each selected from the group consisting of alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), serine (ser—S), threonine (thr—T), tryptophan (trp—W), tyrosine (tyr—Y), valine (val—V), benzyl protected tyrosine, tert-butyloxycarbonyl (BOC) protected tyrosine and combinations thereof.

In one or more embodiments, the amino acid-based poly (ester urea) adhesive of the present invention includes any one or more of the above referenced embodiments of the first aspect of the present invention wherein the at least one of the two or more monomer segments contains a catechol functionalized phenylalanine or tyrosine residue. In one or more embodiments, the amino acid-based poly(ester urea) adhesive of the present invention includes any one or more of the above referenced embodiments of the first aspect of the present invention wherein the at least one of the two or more monomer segments is branched.

In one or more embodiments, the amino acid-based poly (ester urea) adhesive of the present invention includes any one or more of the above referenced embodiments of the first aspect of the present invention wherein the amino acid-based poly(ester urea) adhesive comprises: a first segment containing two catechol-functionalized amino acid groups separated by from 2 to 20 carbon atoms; and a second segment containing two amino acid groups separated by from 2 to 20 carbon atoms. In one or more embodiments, the amino acid-based poly(ester urea) adhesive of the present invention includes any one or more of the above referenced embodiments of the first aspect of the present invention where the first segment has the formula:

(I)

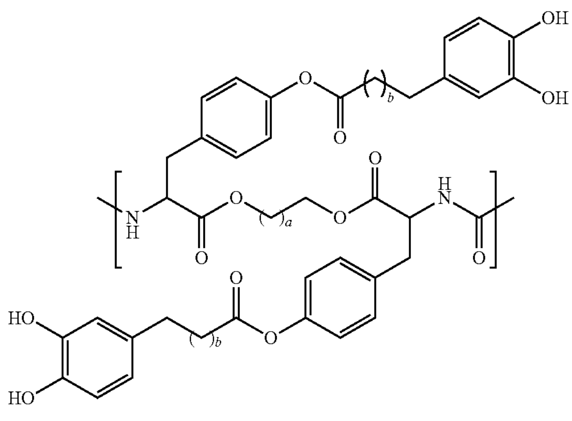

wherein a is an integer from 1 to 20 and b is an integer from 1 to 6.

In one or more embodiments, the amino acid-based poly (ester urea) adhesive of the present invention includes any one or more of the above referenced embodiments of the first aspect of the present invention wherein the two amino acid groups of the second segment are selected from the group consisting of alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), serine (ser—S), threonine (thr—T), tryptophan (trp—W), tyrosine (tyr—Y), valine (val—V), and combinations thereof.

In one or more embodiments, the amino acid-based poly (ester urea) adhesive of the present invention includes any one or more of the above referenced embodiments of the first aspect of the present invention where the second segment has the formula:

(II)

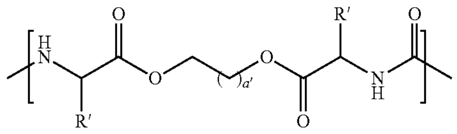

wherein R' is $—CH_3$, $—(CH_2)_3NHC(NH_2)C{=}NH$, $—CH_2CONH_2$, $—CH_2COOH$, $—CH_2SH$, $—(CH_2)_2COOH$, $—(CH_2)_2CONH_2$, $—NH_2$, $—CH_2C{=}CH—N{=}CH—NH$, $—CH(CH_3)CH_2CH_3$, $—CH_2CH(CH_3)_2$, $—(CH_2)_4NH_2$, $—(CH_2)_2SCH_3$, $—CH_2Ph$, $—CH_2OH$, $—CH(OH)CH_3$, $—CH_2—C{=}CH—NH\text{-}Ph$, $—CH_2Ph\text{-}OH$, or $—CH(CH_3)_2$; and a' is an integer from 1 to 20.

In one or more embodiments, the amino acid-based poly (ester urea) adhesive of the present invention includes any one or more of the above referenced embodiments of the first aspect of the present invention having the formula:

(III)

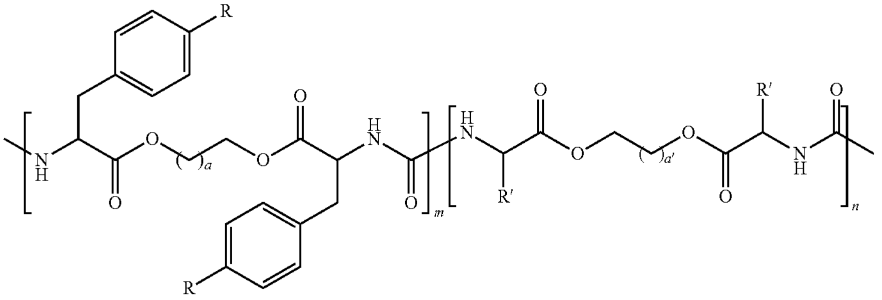

where R is H, OH, or —OCOO$(CH_2)_2C_6H_3(OH)_2$; R' is —$CH_3$, —$(CH_2)_3NHC(NH_2)C$═NH, —$CH_2CONH_2$, —$CH_2COOH$, —$CH_2SH$, —$(CH_2)_2COOH$, —$(CH_2)_2CONH_2$, —$NH_2$, —$CH_2C$═CH—N═CH—NH, —$CH(CH_3)CH_2CH_3$, —$CH_2CH(CH_3)_2$, —$(CH_2)_4NH_2$, —$(CH_2)_2SCH_3$, —$CH_2Ph$, —$CH_2OH$, —CH(OH)$CH_3$, —$CH_2$—C═CH—NH-Ph, —$CH_2$-Ph-OH, or —$CH(CH_3)_2$; a and a' are each an integer from about 1 to about 20; and m and n are mole fractions.

In one or more embodiments, the amino acid-based poly (ester urea) adhesive of the present invention includes any one or more of the above referenced embodiments of the first aspect of the present invention having the formula:

(IV)

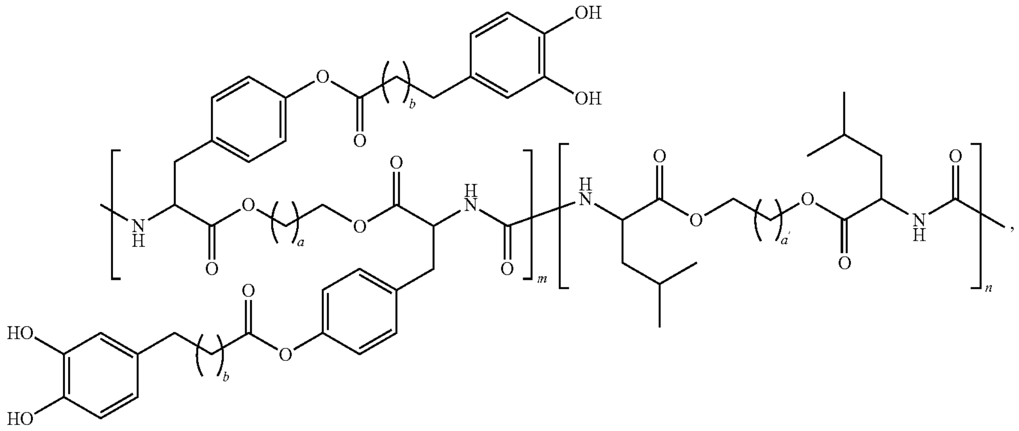

(V)

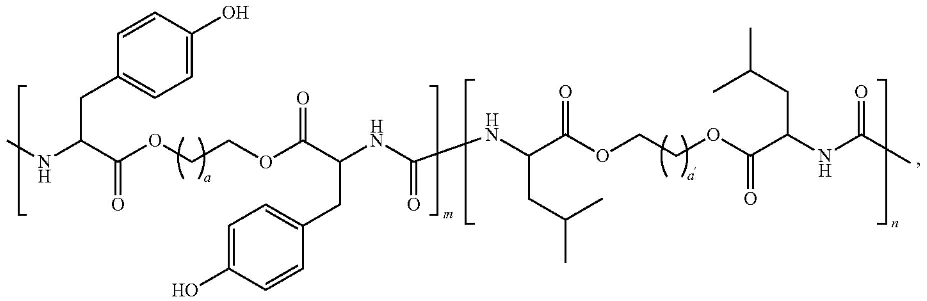

(VI)

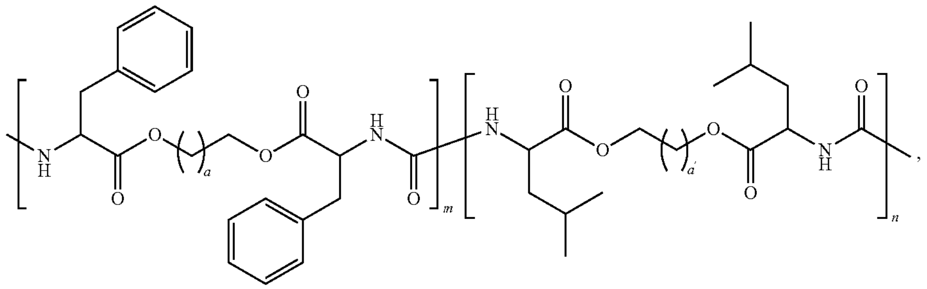

-continued
(VII)
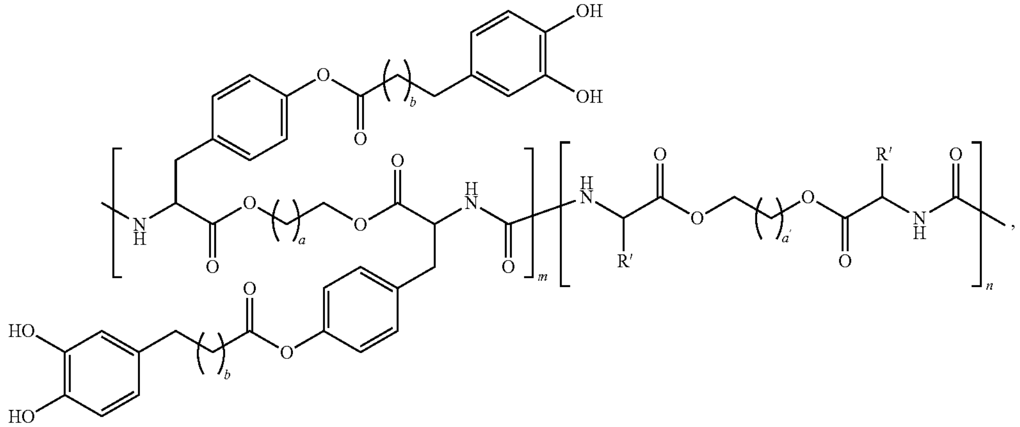
(VIII)
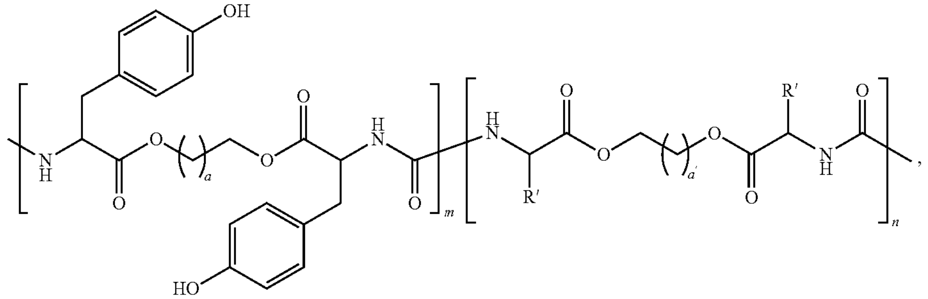
(IX)
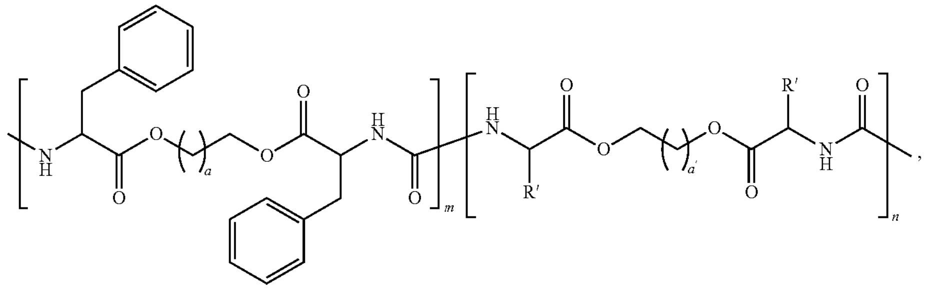
(X)
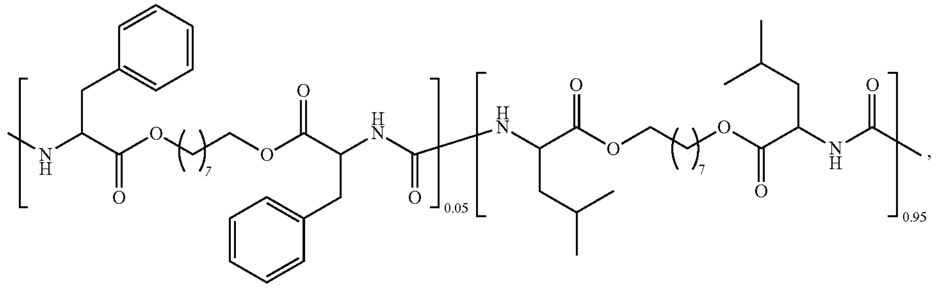
(XI)
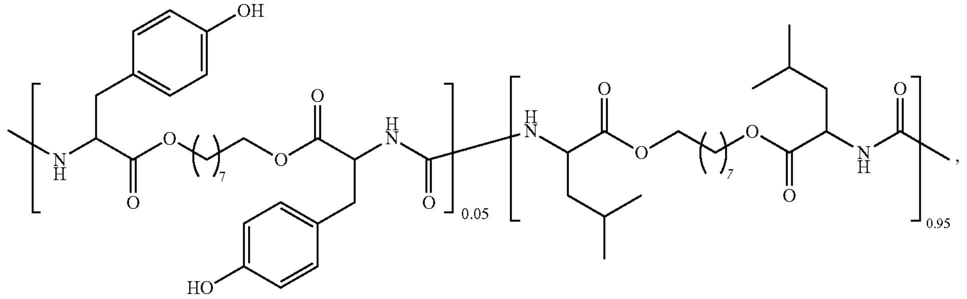

-continued
(XII)
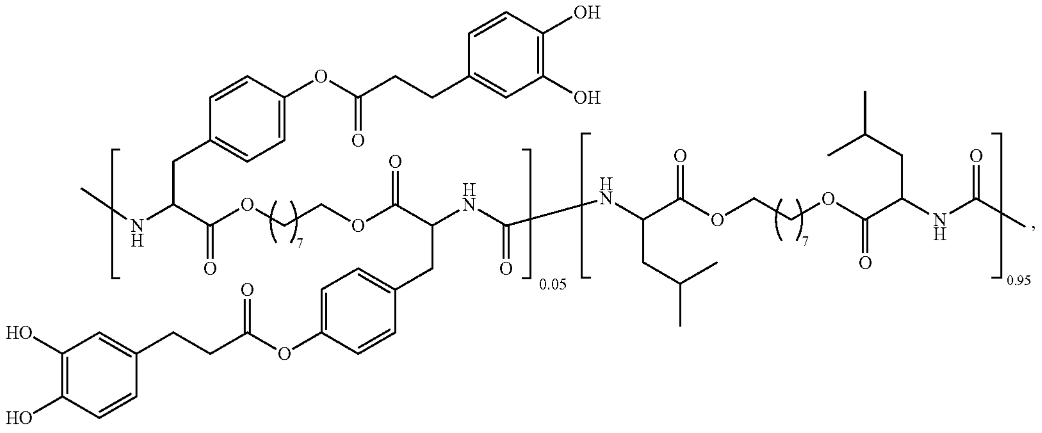
(XIII)
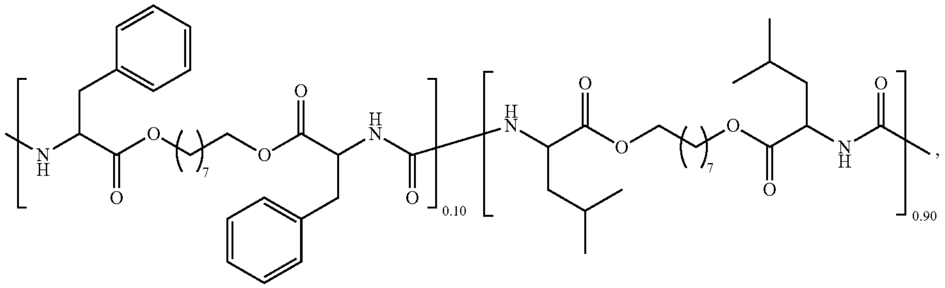
(XIV)
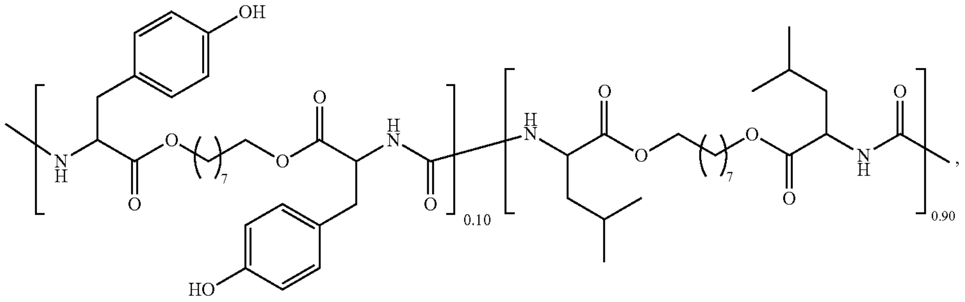
(XV)
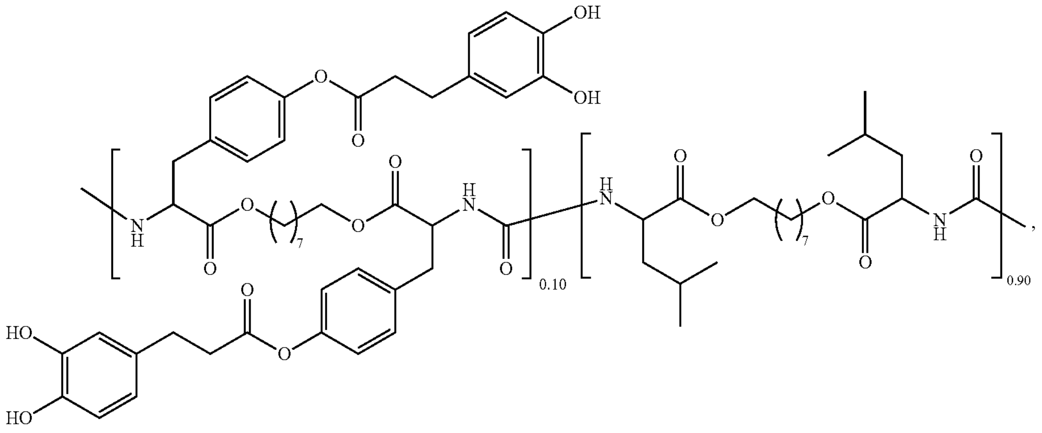

-continued
(XVI)
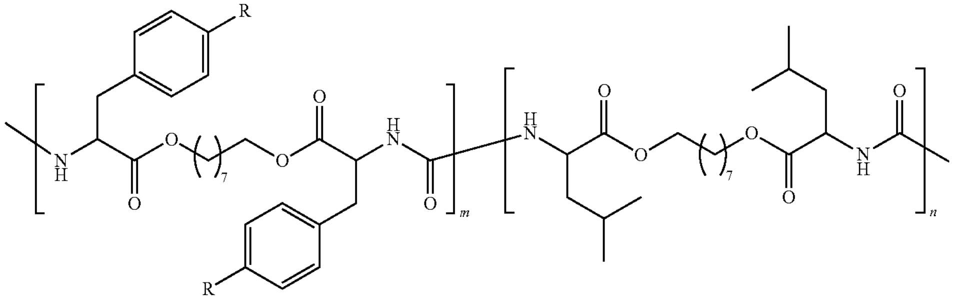
,
(XVII)
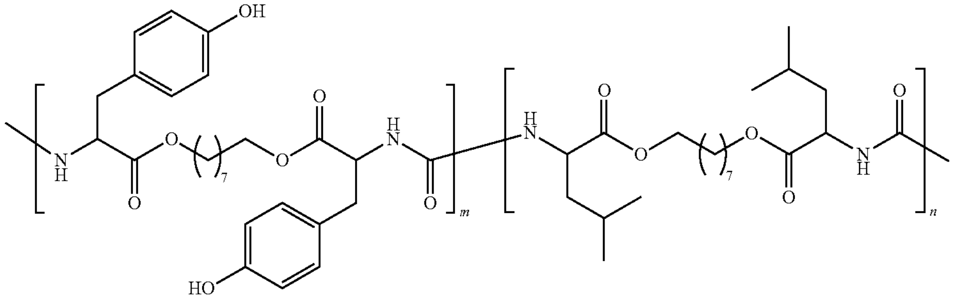
,
(XVIII)
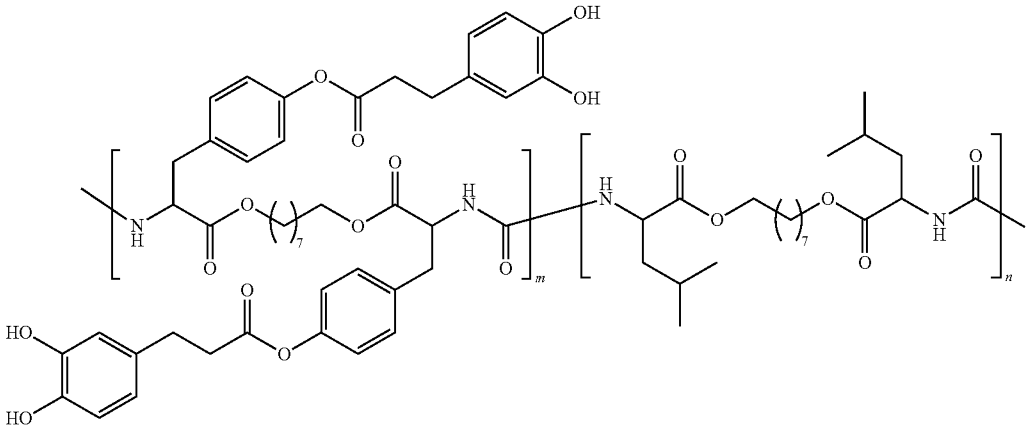
, or
(XIX)
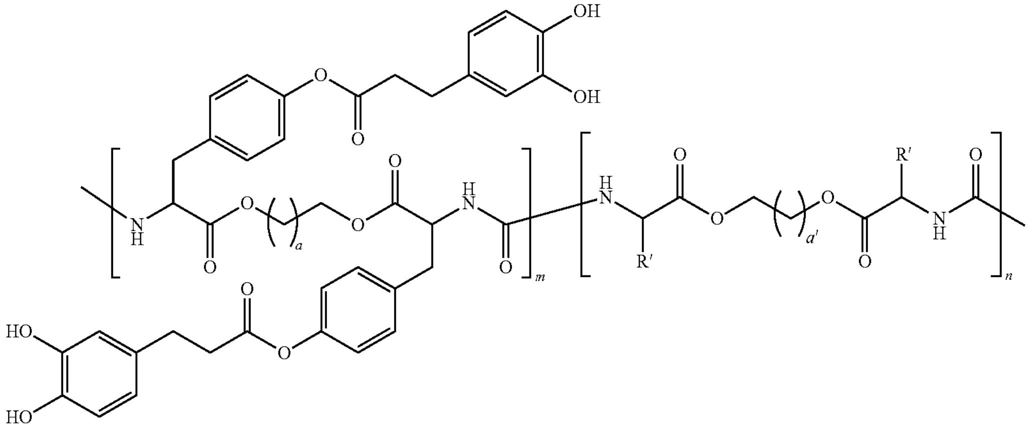
wherein R' is —$CH_3$, —$(CH_2)_3NHC(NH_2)C$═NH, —$CH_2CONH_2$, —$CH_2COOH$, —$CH_2SH$, —$(CH_2)_2COOH$, —$(CH_2)_2CONH_2$, —$NH_2$, —$CH_2C$═CH—N═CH—NH, —$CH(CH_3)CH_2CH_3$, —$CH_2CH(CH_3)_2$, —$(CH_2)_4NH_2$, —$(CH_2)_2SCH_3$, —$CH_2Ph$, —$CH_2OH$, —$CH(OH)CH_3$, —$CH_2$—C═CH—NH-Ph, —$CH_2$-Ph-OH, or —$CH(CH_3)_2$; a and a' are each integers from 1 to 20; b is an integer from 1 to 6; m is a mole fraction from 0.01 to 0.30; and n is a mole fraction from 0.70 to 0.99.

In one or more embodiments, the amino acid-based poly (ester urea) adhesive of the present invention includes any one or more of the above referenced embodiments of the first aspect of the present invention further comprising an oxidative cross linker.

In a second aspect, the present invention is directed to a method for making the biodegradable PEU adhesive described above comprising: preparing a first counter-ion protected polyesterester monomer, wherein the first counter-ion protected polyesterester monomer comprises two phenylalanine residues separated by from 2 to 20 carbon atoms; preparing a second counter-ion protected polyester monomer, wherein the second counter-ion protected polyester monomer comprises two amino acid residues separated by from 2 to 20 carbon atoms; reacting the first counter-ion protected polyester monomer and second counter-ion protected polyester monomer with a poly(ester urea) forming compound to form an amino acid-based poly(ester urea) having a first segment comprising the residue of the first counter-ion protected polyester monomer and a second segment comprising the residue of the second counter-ion protected polyester monomer.

In some of these embodiments, the first counter-ion protected polyester monomer has the formula:

(XX)

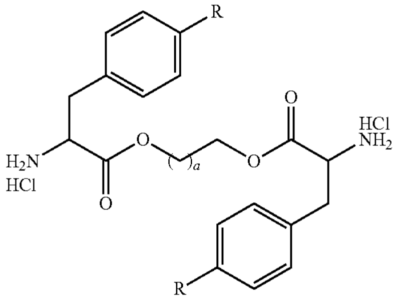

wherein R is H, OH, $OCH_2$-Ph or —$OCOOCH(CH_3)_3$; and a is an integer from about 1 to about 20. In one or more embodiments, the method of the present invention includes any one or more of the above referenced embodiments of the second aspect of the present invention wherein one or both of the first counter-ion protected polyester monomer and the second counter-ion protected polyester monomer are branched.

In one or more embodiments, the method of the present invention includes any one or more of the above referenced embodiments of the second aspect of the present invention wherein the first counter-ion protected polyester monomer comprises two benzyl protected tyrosine residues separated by from 2 to 20 carbon atoms, the method further comprising: reacting the first counter-ion protected polyester monomer and second counter-ion protected polyester monomer with a urea forming compound to form a first amino acid-based poly(ester urea) intermediate having a first segment comprising two benzyl protected tyrosine residues separated by from 2 to 20 carbon atoms and a second segment comprising the residue of two amino acids separated by from 2 to 20 carbon atoms; and removing the protecting benzyl groups from the tyrosine residues of the first segment the amino acid-based poly(ester urea) to form a tyrosine-based poly(ester urea) adhesive.

In one or more embodiments, the method of the present invention includes any one or more of the above referenced embodiments of the second aspect of the present invention further comprising preparing a carboxyl functionalized protected catechol compound, the carboxyl functionalized protected catechol compound comprising a protected catechol group and a carboxyl group; reacting the carboxyl functionalized protected catechol compound with the hydroxyl groups of the tyrosine-based poly(ester urea) urea, thereby coupling the protected catechol group to the first amino acid-based poly(ester urea) intermediate to form a second amino acid-based poly(ester urea) intermediate having one or more protected catechol groups; and deprotecting the one or more protected catechol groups on the third poly(ester urea) intermediate to produce a degradable amino acid-based poly(ester urea) adhesive.

In one or more embodiments, the method of the present invention includes any one or more of the above referenced embodiments of the second aspect of the present invention wherein, the second counter-ion protected polyester monomer comprises the residues of two amino acids selected from the group consisting of alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), serine (ser—S), threonine (thr—T), tryptophan (trp—W), tyrosine (tyr—Y), valine (val—V), benzyl protected tyrosine, BOC protected tyrosine and combinations thereof, separated by from 2 to 20 carbon atoms.

In one or more embodiments, the method of the present invention includes any one or more of the above referenced embodiments of the second aspect of the present invention wherein, the molar ratio of the first counter-ion protected polyester monomer to the second counter-ion protected counter-ion protected polyester monomer is from about 1:20 to about 1:10. In one or more embodiments, the method of the present invention includes any one or more of the above referenced embodiments of the second aspect of the present invention wherein the protected catechol group and the carboxyl group of the carboxyl functionalized protected catechol compound are separated by from 1 to 6 carbon atoms.

In one or more embodiments, the method of the present invention includes any one or more of the above referenced embodiments of the second aspect of the present invention wherein the carboxyl functionalized protected catechol compound comprises 2,2-dimethyl-1,3-benzodioxole-5-propanoic acid, 2,2-dimethyl-1,3-benzodioxole-5-butanoic acid, 2,2-dimethyl-1,3-benzodioxole-5-petnanoic acid, 2,2-dimethyl-1,3-benzodioxole-5-hexanoic acid, 2,2-dimethyl-1,3-benzodioxole-5-heptanoic acid, or 2,2-dimethyl-1,3-benzodioxole-5-octanoic acid.

In one or more embodiments, the method of the present invention includes any one or more of the above referenced embodiments of the second aspect of the present invention wherein the carboxyl functionalized protected catechol compound has the formula:

(XXI)

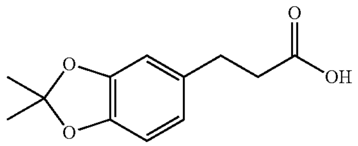

In one or more embodiments, the method of the present invention includes any one or more of the above referenced embodiments of the second aspect of the present invention wherein, the first amino acid-based poly(ester urea) intermediate has the formula:

(III)

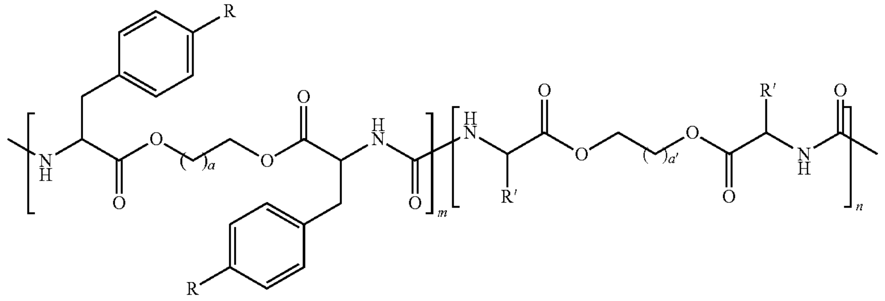

wherein R is $OCH_2$-Ph or —$OCOOCH(CH_3)_3$; R' is —$CH_3$, —$(CH_2)_3NHC(NH_2)C{=}NH$, —$CH_2CONH_2$, $CH_2COOH$, —$CH_2SH$, —$(CH_2)_2COOH$, —$(CH_2)_2CONH_2$, —$NH_2$, —$CH_2C{=}CH{-}N{=}CH{-}NH$, —$CH(CH_3)CH_2CH_3$, —$CH_2CH(CH_3)_2$, —$(CH_2)_4NH_2$, —$(CH_2)_2SCH_3$, —$CH_2Ph$, —$CH_2OH$, —$CH(OH)CH_3$, —$CH_2{-}C{=}CH{-}$NH-Ph, —$CH_2$-Ph-OH, or —$CH(CH_3)_2$; a and a' are each an integer from about 1 to about 20; and m and n are mole fractions.

In one or more embodiments, the method of the present invention includes any one or more of the above referenced embodiments of the second aspect of the present invention wherein, the tyrosine-based poly(ester urea) adhesive has the formula:

(VIII)

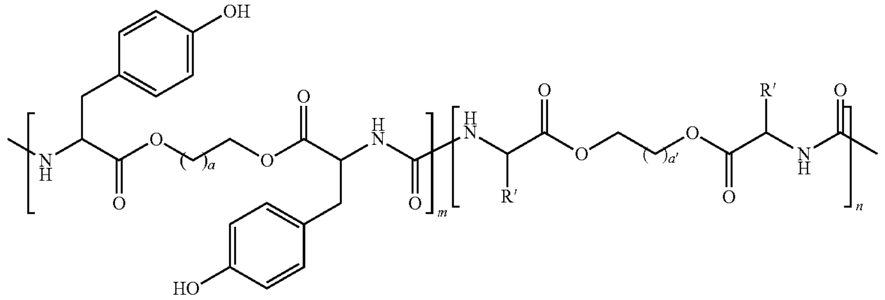

wherein R' is —$CH_3$, —$(CH_2)_3NHC(NH_2)C{=}NH$, —$CH_2CONH_2$, —$CH_2COOH$, —$CH_2SH$, —$(CH_2)_2COOH$, —$(CH_2)_2CONH_2$, —$NH_2$, —$CH_2C{=}CH{-}N{=}CH{-}NH$, —$CH(CH_3)CH_2CH_3$, —$CH_2CH(CH_3)_2$, —$(CH_2)_4NH_2$, —$(CH_2)_2SCH_3$, —$CH_2Ph$, —$CH_2OH$, —$CH(OH)CH_3$, —$CH_2C{=}CH{-}$NH-Ph, —$CH_2$-Ph-OH, or —$CH(CH_3)_2$; a and a' are each an integer from about 1 to about 20; and m and n are mole fractions.

In one or more embodiments, the method of the present invention includes any one or more of the above referenced embodiments of the second aspect of the present invention wherein, the third amino acid-based poly(ester urea) intermediate has the formula:

(XXII)

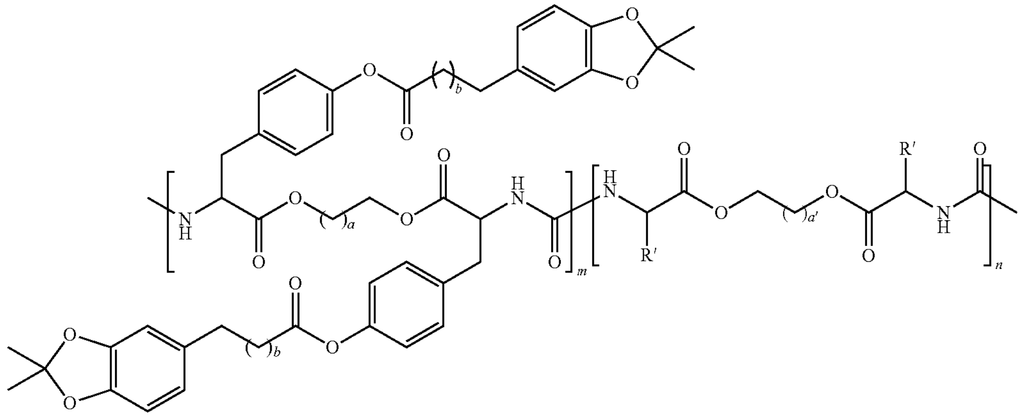

wherein R is $—CH_3$, $—(CH_2)_3NHC(NH_2)C═NH$, $—CH_2CONH_2$, $—CH_2COOH$, $—CH_2SH$, $—(CH_2)_2COOH$, $—(CH_2)_2CONH_2$, $—NH_2$, $—CH_2C═CH—N═CH—NH$, $—CH(CH_3)CH_2CH_3$, $—CH_2CH(CH_3)_2$, $—(CH_2)_4NH_2$, $—(CH_2)_2SCH_3$, $—CH_2Ph$, $—CH_2OH$, $—CH(OH)CH_3$, $—CH_2C═CH—NH\text{-}Ph$, $—CH_2\text{-}Ph\text{-}OH$, or $—CH(CH_3)_2$; a and a' are each an integer from about 1 to about 20; b is an integer from 1 to 6; and m and n are mole fractions. In some of these embodiments, a and a' are 7 and b is 1.

In one or more embodiments, the method of the present invention includes any one or more of the above referenced embodiments of the second aspect of the present invention, wherein the degradable amino acid-based poly(ester urea) adhesive has the formula:

BRIEF DESCRIPTION OF THE DRAWINGS

For a more complete understanding of the features and advantages of the present invention, reference is now made to the detailed description of the invention along with the accompanying figures in which.

(VII)

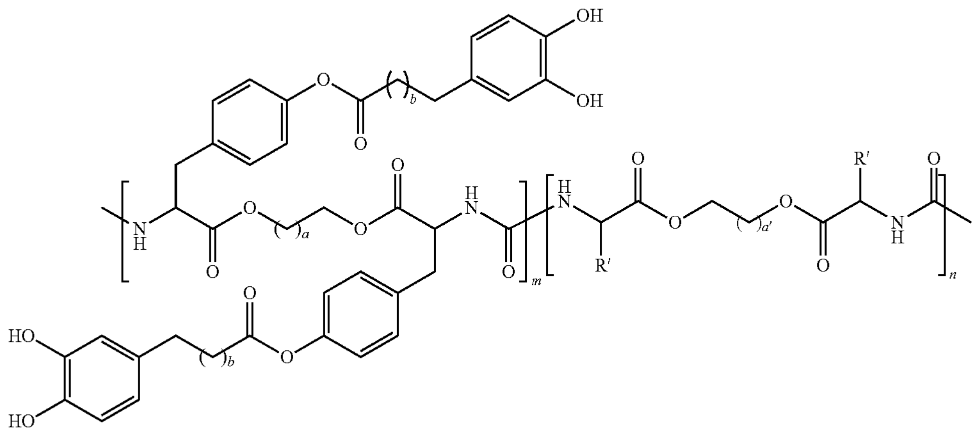

wherein R' is $—CH_3$, $—(CH_2)_3NHC(NH_2)C═NH$, $—CH_2CONH_2$, $—CH_2COOH$, $—CH_2SH$, $—(CH_2)_2COOH$, $—(CH_2)_2CONH_2$, $—NH_2$, $—CH_2C═CH—N═CH—NH$, $—CH(CH_3)CH_2CH_3$, $—CH_2CH(CH_3)$, $—(CH_2)_4NH_2$, $—(CH_2)_2SCH_3$, $—CH_2Ph$, $—CH_2OH$, $—CH(OH)CH_3$, $—CH_2—C═CH—NH\text{-}Ph$, $—CH_2\text{-}Ph\text{-}OH$, or $—CH(CH_3)_2$; a and a' are each integers from 1 to 20; b is an integer from 1 to 6; m is a mole fraction from 0.01 to 0.30; and n is a mole fraction from 0.70 to 0.99.

Figure 2:
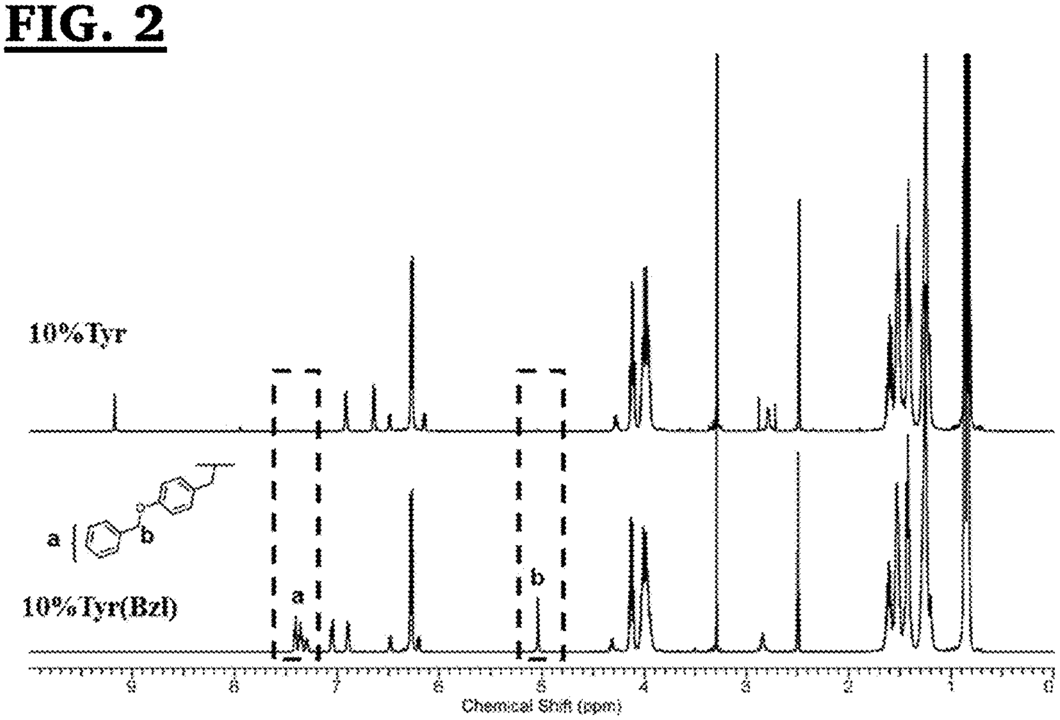

FIG. 2 is a schematic comparison of the $^1$H NMR spectra of PEU polymers having 10% benzyl protected tyrosine groups (10% Tyr(Bzl)) (lower) and 10% tyrosine groups (10% Tyr) (upper).

Figure 3:
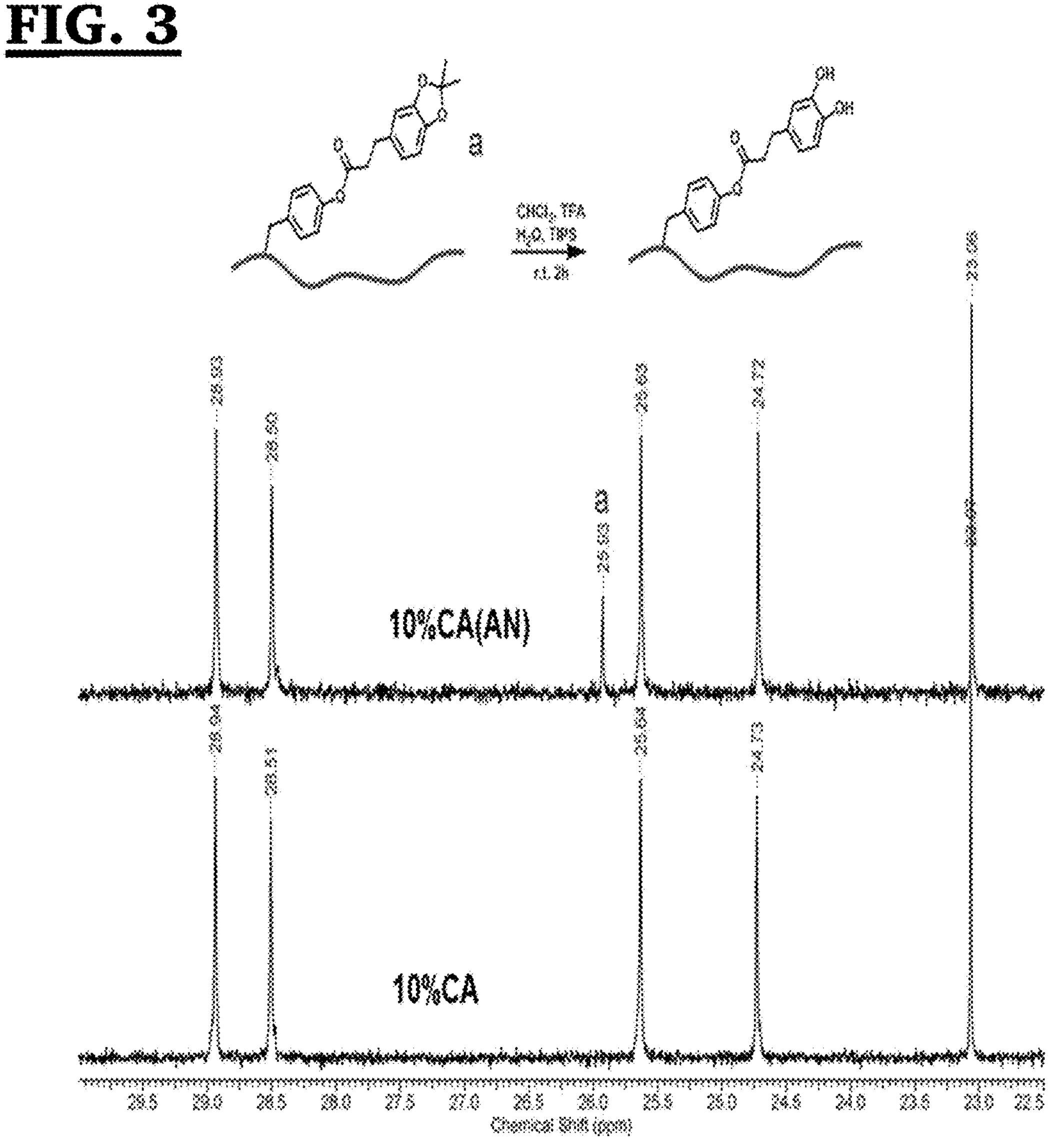

FIG. 3 is a schematic comparison of part of the $^{13}$C NMR spectra of PEU polymers having 10% acetonide protected catechol groups (10% Ca(AN)) (upper) and 10% catechol groups (10% CA) (lower). The disappearance of the peak at 25.93 ppm indicates the deprotection is successful.

Figure 4A:
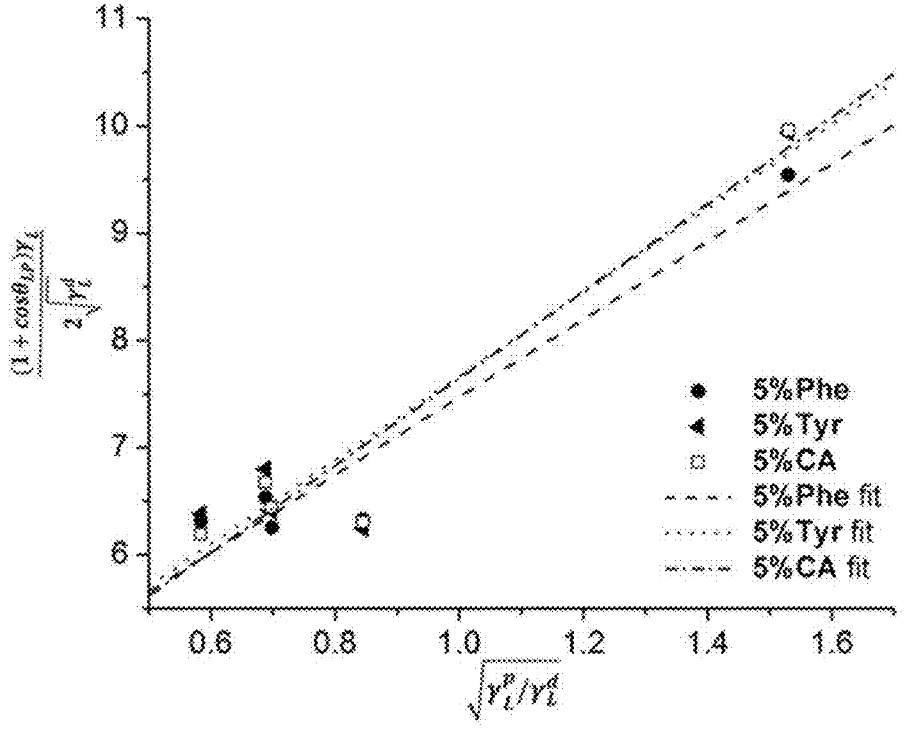
Figure 4B:
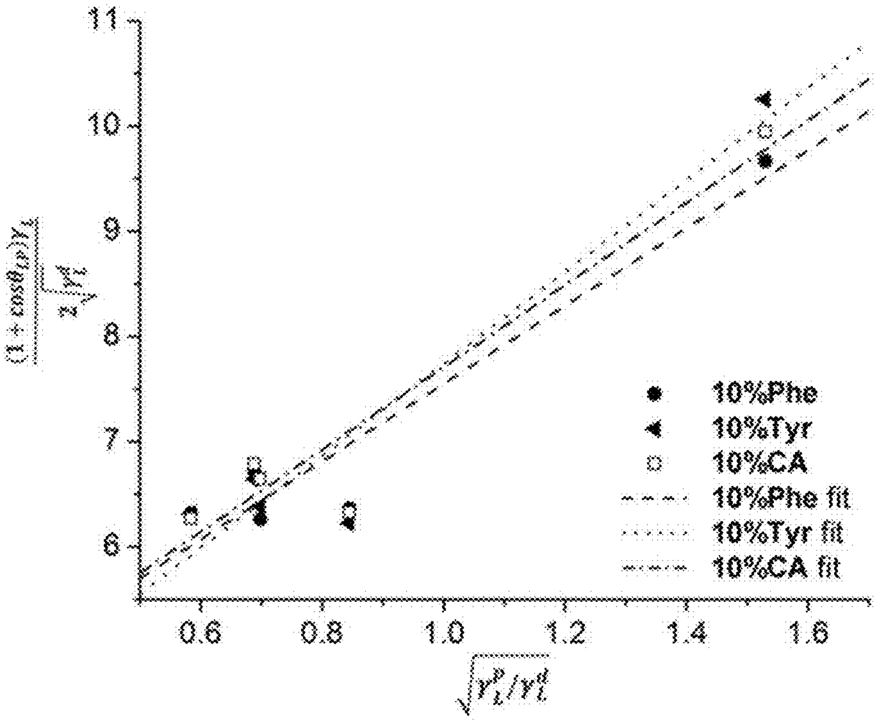

FIGS. 4A-B are surface energy fitting plots derived from contact angle measurements. FIG. 4A is a surface energy plot fitting curves for PEUs having 5% phenylalanine groups (5% Phe), 5% tyrosine groups (5% Tyr), and 5% catechol groups (5% CA) and FIG. 4B is a surface energy plot fitting curves for PEUs having 10% phenylalanine groups (10% Phe), 10% tyrosine groups (10% Tyr), and 10% catechol groups (10% CA).

Figure 5A:
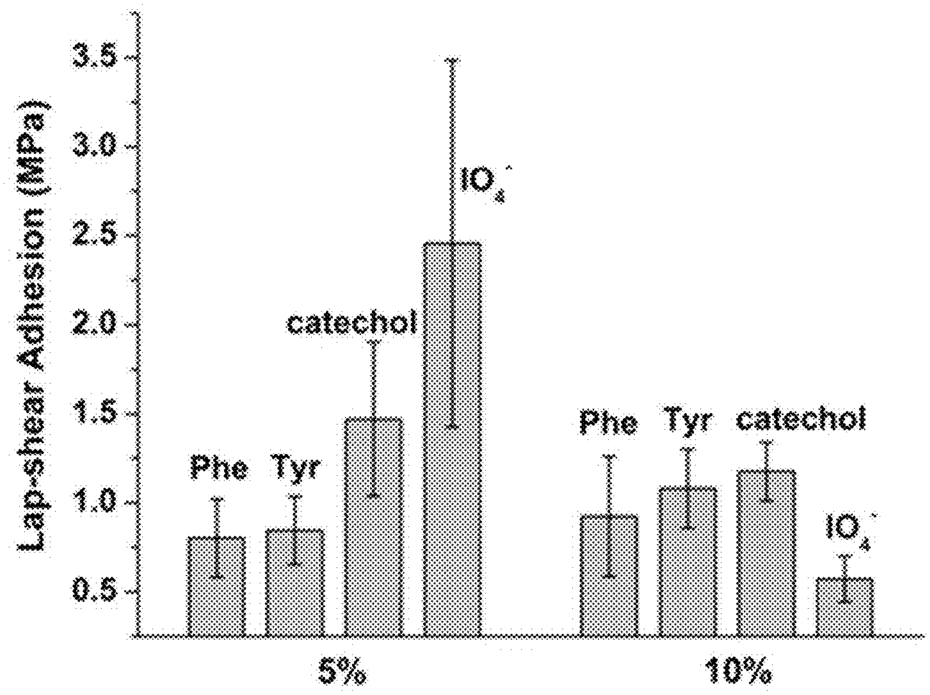

FIG. 5A is a graph showing the results of lap-shear adhesion tests on PEU polymers having 5% and 10% phenylalanine groups, tyrosine groups, catechol groups, and catechol groups with the addition of tetrabutylammonium periodate as cross-linker on aluminum adherends. Tests performed at room temperature (r.t.). For each test, at least six samples were measured and averaged.

Figure 5B:
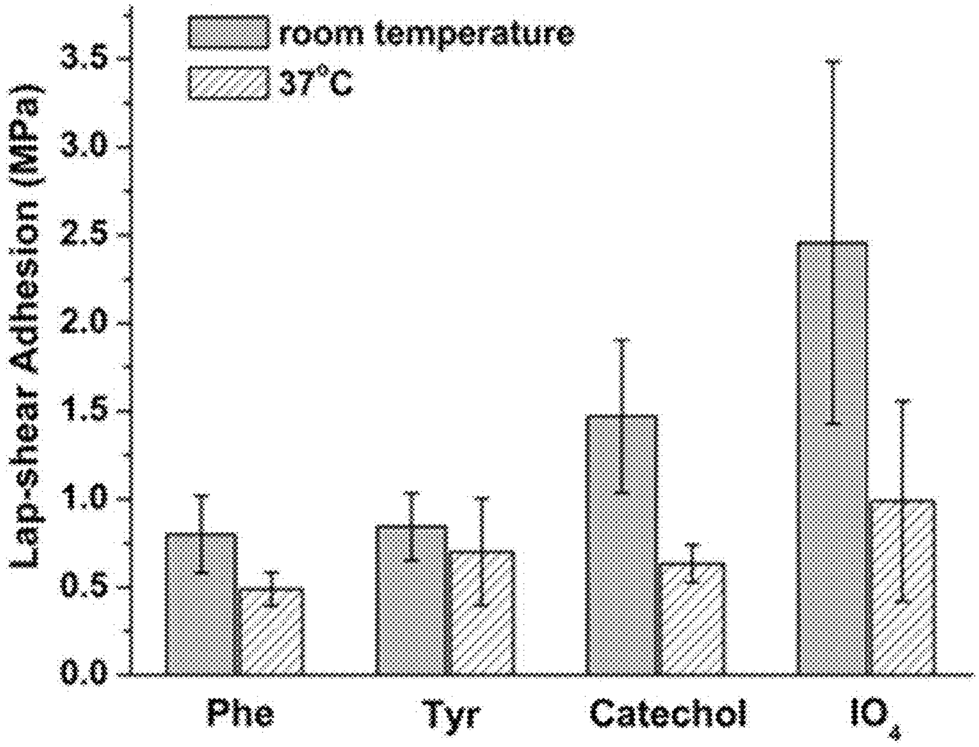

FIG. 5B is a graph comparing lap-shear test results for PEU polymers having 5% phenylalanine groups, 5% tyrosine groups, 5% catechol groups, and 5% catechol groups with the addition of tetrabutylammonium periodate as cross-linker at room temperature and at 37° C. For each test, at least six samples were measured and averaged.

Figure 6A:
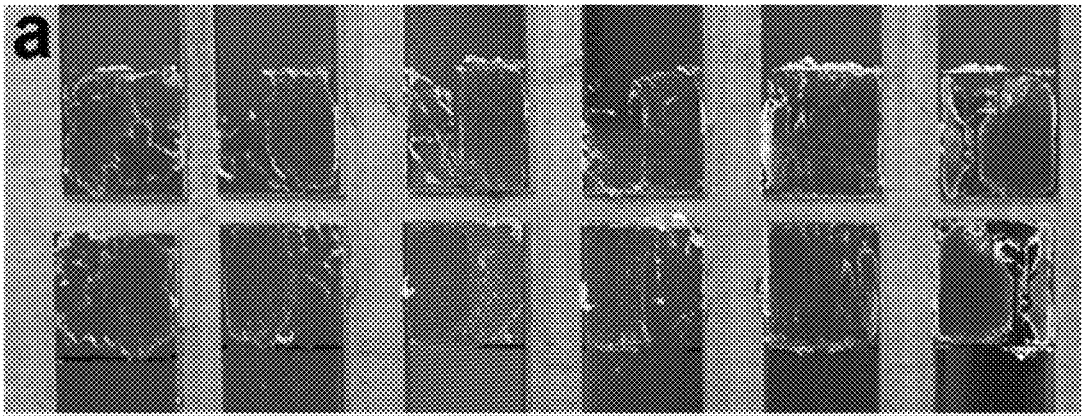
Figure 6B:
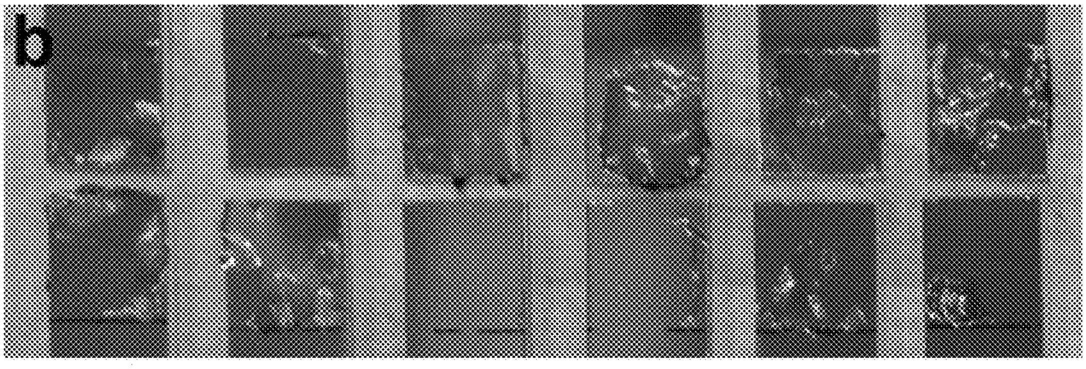

FIGS. 6A-B are representative images of adherends with different failure types. FIG. 6A shows images of the adherends after a lap-shear adhesion test of 10% CA with a majority of cohesive failure. FIG. 6B shows images of the adherends after a lap-shear adhesion test of 10% CA with cross-linker showing adhesive failure.

Figure 7:
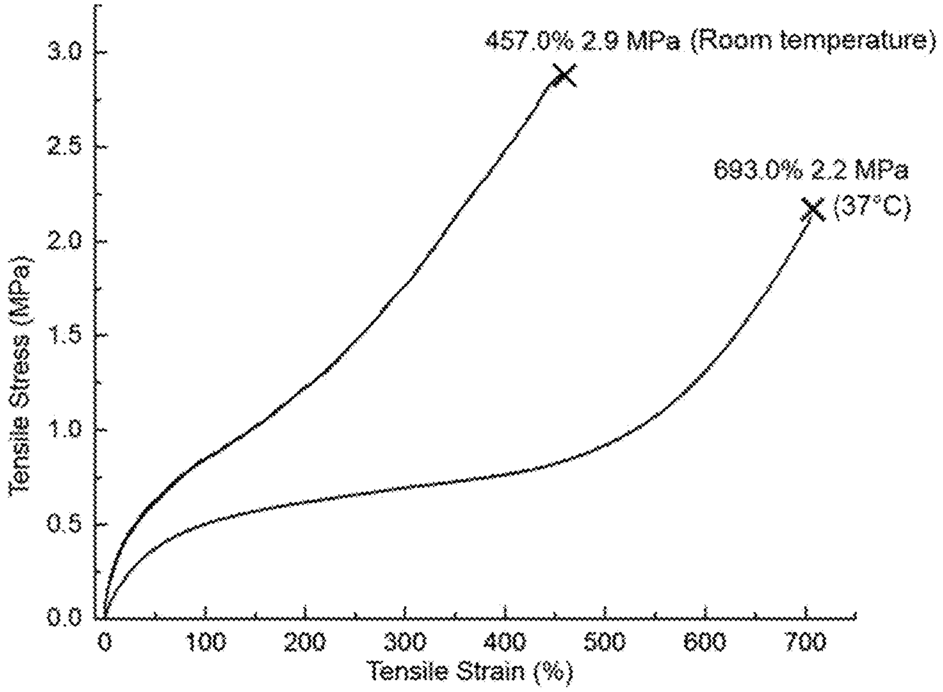

FIG. 7 is a stress-strain curve for 5% Phe measured at room temperature (25±1° C.) with rectangular samples and measured at physiological temperature (37±1° C.). Three measurements were done for each sample.

Figure 8:
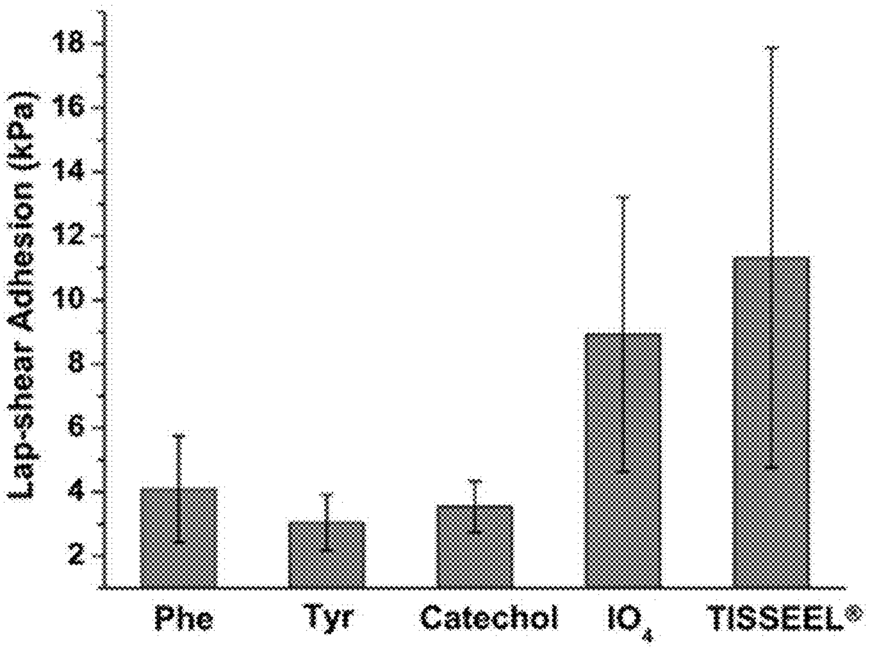

FIG. 8 is a graph showing lap-shear adhesion properties of PEU adhesives having 5% phenylalanine groups, 5% tyrosine groups, 5% catechol groups, 5% catechol groups with the addition of tetrabutylammonium periodate as cross-linker, and TISSEEL® fibrin glue, using porcine skin adherends. At least five samples were measured for each test and results were averaged.

Figure 9A:
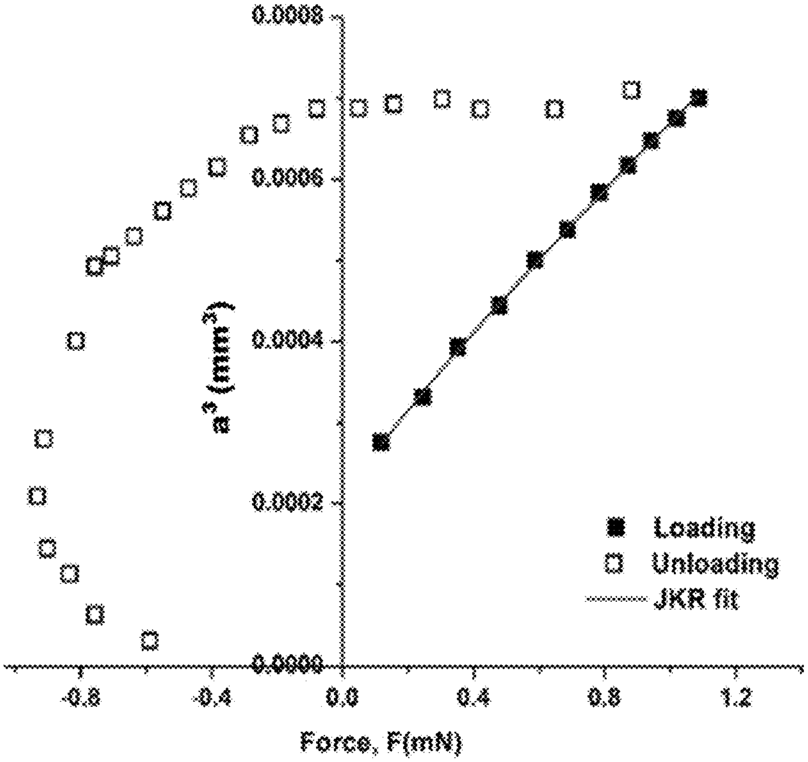
Figure 9B:
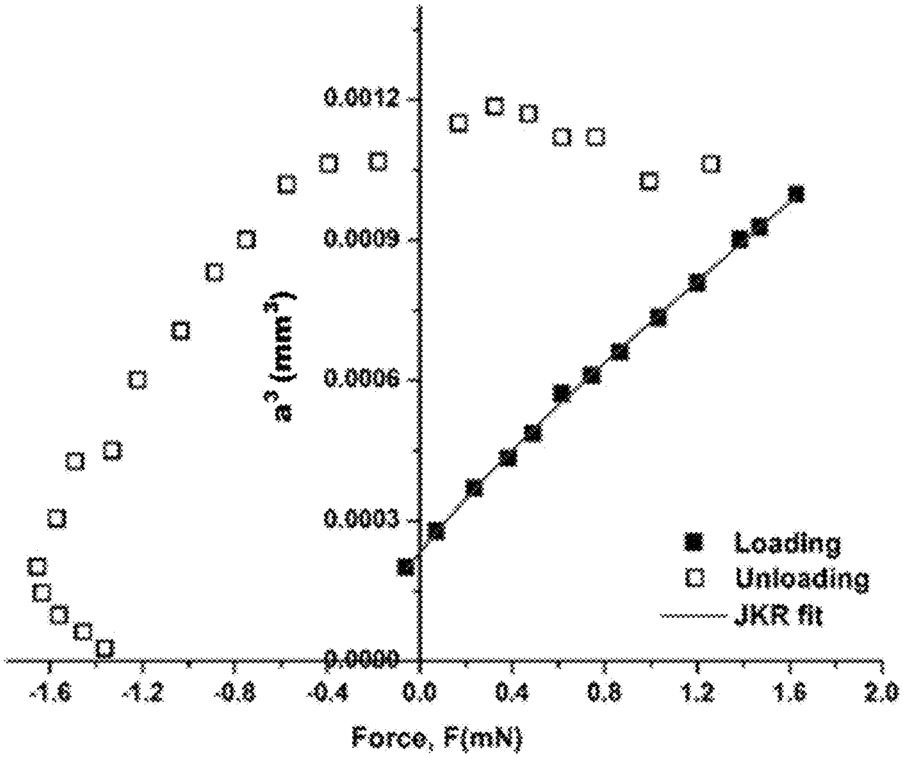
Figure 9C:
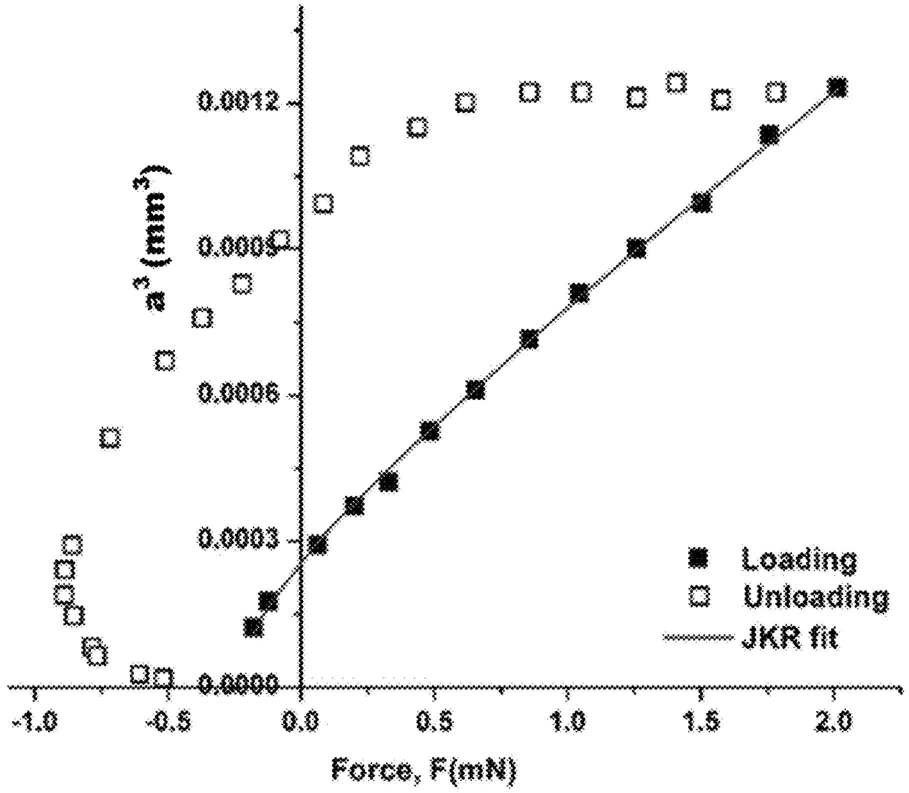

FIGS. 9A-C are plots showing of cubic contact radius versus compressive force during the loading and unloading processes of Jackson-Kendall-Roberts (JKR) measurements on PEU surfaces having: 5% phenylalanine groups (FIG. 8A), 5% tyrosine groups (FIG. 8B), and 5% catechol groups (FIG. 8C) in air.

DETAILED DESCRIPTION OF THE ILLUSTRATIVE EMBODIMENTS

In general outline, the present invention is directed to a novel group of amino acid-based poly(ester urea)s for use in biodegradable adhesive and related methods for its making and use. These novel amino acid-based poly(ester urea)s (PEUs) have a wide variation in mechanical properties and degradation behavior that can be tuned by varying the amino acids and polyols used to form the polyester monomers that form these PEUs. Importantly, these novel PEUs have been shown to be non-toxic in vitro and in vivo and may be suitable to a wide variety of biomedical and other uses. In some embodiments, the adhesive properties of these degradable amino acid-based poly(ester urea) adhesives have been further improved by the incorporation of controlled amounts of catechol functional groups into the side chains of the PEU via post-polymerization functionalization chemistry.

Further, the amino acid-based PEU adhesives of various embodiments of the present invention are biodegradable. As used herein, the terms "degradable," and "biodegradable" are used interchangeably to refer to a macromolecule or other polymeric substance susceptible to degradation by biological activity by lowering the molecular masses of the macromolecules that form the substance. The PEU polymers used to form the amino acid-based PEU adhesives of various embodiments of the present invention are degradable, but their degradation properties will depend upon such things as the molecular weight of the PEU, the size and structure of the diol or polyol residue used, the particular amino acid residue(s) present, and any additional functional groups added after polymerization. By manipulating these variables, the degradation properties of the amino acid-based PEU adhesives of the present invention may be tuned to obtain a wide variety degradation profiles and other characteristics and may be tuned for specific applications.

The PEUs of various embodiments of the present invention may be synthesized from counter-ion protected polyester monomers comprising the residue of two or more amino acids and a diol or other polyol and a PEU forming compound such as phosgene, diphosgene, or triphosgene, as will be described in more detail below. Accordingly, the PEUs of the various embodiments of the present invention may comprise a series of amino acid-based polyester segments/units, each having the residue of two or more amino acids separated from each other by the residue of a diol or other polyol, that are joined to each other by urea bonds.

The amino acid-based polyester segments may comprise the residues any α-amino acid other than proline. As used herein, the term "residue(s)" is used to refer generally to the part of a monomer or other chemical unit that has been incorporated into a polymer or large molecule. By extension, the terms "residue of an amino acid" and "amino acid residue" are used interchangeably to refer to part of the amino acids used to form the counter-ion protected amino acid-based polyester monomers that is incorporated into the counter-ion protected polyester monomers and the terms "residue of a diol or other polyol," "diol or other polyol residue," "diol residue," and "polyol residue" are used to refer to the part of the diol or other polyol used to form the counter-ion protected amino acid-based polyester monomers that is incorporated into the counter-ion protected amino acid-based polyester monomers. Likewise, the terms "monomer residue," "polyester monomer residue," "amino acid-based polyester monomer residue," are used interchangeably to refer to the part of a counter-ion protected amino acid-based polyester monomer that is incorporated into amino acid-based PEU adhesives of the present invention. Finally, the terms "polyester segments," "polyester units," "amino acid-based polyester segments," and "amino acid-based polyester units" are used interchangeably to refer to portions of the amino acid-based PEU adhesives of the present invention formed from a particular counter-ion protected amino acid-based polyester monomer.

In some embodiments, the amino acid-based polyester segments may comprise residues of alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), serine (ser—S), threonine (thr—T), tryptophan (trp—W), tyrosine (tyr—Y), valine (val—V), or any combinations or derivatives thereof. In some embodiments, at least one of the amino acid-based polyester segments may comprise residues of phenylalanine or tyrosine. In some embodiments, at least one of the amino acid-based polyester segments may be functionalized after polymerization to contain a catechol group.

In some embodiments, all of the amino acid residues in a particular amino acid-based polyester segment may be the same, but this need not be the case. In some other embodiments, a particular amino acid-based polyester segment may contain different amino acid residues.

As set forth above, the amino acids residues in the polyester segments may be separated from each other by the residue of a linear or branched diol or other polyol. In some embodiments, the amino acids residues may be separated from each other by the residue of a linear diol including, without limitation, 1,6-hexanediol, 1,8-octanediol, 1,9-nonanediol, 1,10-decanediol, 1,11-undecanediol, 1,12-dodecanediol, 1,13-trinecanediol, 1,14-tetradecanediol, 1,15-pentadecanediol, 1,16-hexadecanediol, 1,17-heptadecanediol, 1,18-octadecanediol, 1,19-nonadecanediol, 1,20-icosanediol, and combinations thereof. In the embodiments, the polyol may be 1,8-octanediol and is commercially available from Sigma Aldrich Company LLC (St. Louis, Mo.) or Alfa Aesar (Ward Hill, Mass.). In some other embodiments, the amino acids residues may be separated from each other by the residue of a branched polyol including, without limitation, 2-butene-1,4-diol, 3,4-dihydroxy-1-butene, 7-octene-1,2-diol, 3-hexene-1,6-diol, 1,4-butynediol, trimethylolpropane allyl ether, 3-allyloxy-1,2-propanediol, 2,4-hexadiyne-1,6-diol, 2-hydroxymethyl-1,3-propanediol, 1,1,1-tris(hydroxymethyl)propane, 1,1,1-tris(hydroxymethyl) ethane, pentaerythritol, di(trimethylolpropane) dipentaerythritol and combinations thereof.

In some embodiments, the amino acid-based polyester segments are linear and the amino acid residues of the amino-acid-based polyester segments are separated by from about 2 to about 20 carbon atoms. In some of these embodiments, the amino acid residues are separated by from about 2 to about 15 carbon atoms. In some of these embodiments, the amino acid residues are separated by from about 2 to about 10 carbon atoms. In some of these embodiments, the amino acid residues are separated by from about 4 to about 12 carbon atoms. In some of these embodiments, the amino acid residues are separated by from about 6 to about 12 carbon atoms. In some of these embodiments, the amino acid residues are separated by from about 6 to about 15 carbon atoms. In some of these embodiments, the amino acid residues are separated by from about 8 to about 12 carbon atoms.

In some embodiments having a branched polyol residue, the amino acid residues of the amino-acid-based polyester segments are separated by from about 2 to about 60 carbon atoms. In some of these embodiments, the amino acid residues are separated by from about 2 to about 40 carbon atoms. In some of these embodiments, the amino acid residues are separated by from about 2 to about 20 carbon atoms. In some of these embodiments, the amino acid residues are separated by from about 10 to about 60 carbon atoms. In some of these embodiments, the amino acid residues are separated by from about 20 to about 60 carbon atoms. In some of these embodiments, the amino acid residues are separated by from about 30 to about 60 carbon atoms. In some of these embodiments, the amino acid residues are separated by from about 40 to about 60 carbon atoms. In some of these embodiments, the amino acid residues are separated by from about 6 to about 15 carbon atoms.

In some embodiments, the amino acid-based polyester segments are branched and may contain two or more amino acid residues. In these embodiments, these amino acid residues may be separated from each other by from 2 to about 60 carbon atoms. In some of these embodiments, the amino acid residues are separated from each other by from about 10 to about 60 carbon atoms. In some of these embodiments, the amino acid residues are separated from each other by from about 20 to about 60 carbon atoms. In some of these embodiments, the amino acid residues are separated from each other by from about 30 to about 60 carbon atoms. In some of these embodiments, the amino acid residues are separated from each other by from about 40 to about 60 carbon atoms. In some of these embodiments, the amino acid residues are separated from each other by from about 50 to about 60 carbon atoms. In some of these embodiments, the amino acid residues are separated from each other by from about 2 to about 50 carbon atoms. In some of these embodiments, the amino acid residues are separated from each other by from about 2 to about 40 carbon atoms. In some of these embodiments, the amino acid residues are separated from each other by from about 2 to about 30 carbon atoms. In some of these embodiments, the amino acid residues are separated from each other by from about 2 to about 20 carbon atoms. In some of these embodiments, the amino acid residues are separated from each other by from about 2 to about 10 carbon atoms. In some of these embodiments, the amino acid residues are separated from each other by from about 4 to about 15 carbon atoms.

In some embodiments, the amino acid-based polyester segments may have the formula:

(II)

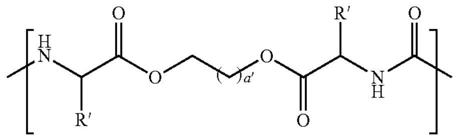

wherein R' is $-CH_3$, $-(CH_2)_3NHC(NH_2)C{=}NH$, $-CH_2CONH_2$, $-CH_2COOH$, $-CH_2SH$, $-(CH_2)_2COOH$, $-(CH_2)_2CONH_2$, $-NH_2$, $-CH_2C{=}CH{-}N{=}CH{-}NH$, $-CH(CH_3)CH_2CH_3$, $-CH_2CH(CH_3)_2$, $-(CH_2)_4NH_2$, $-(CH_2)_2SCH_3$, $-CH_2Ph$, $-CH_2OH$, $-CH(OH)CH_3$, $-CH_2{-}C{=}CH{-}NH{-}Ph$, $-CH_2{-}Ph{-}OH$, $-CH(CH_3)_2$, or $-CH_2C_6H_4OCH_2C_6H_5$; and a' is an integer from 1 to 20. In some of these embodiments, a' may be an integer from about 1 to about 18. In some of these embodiments, a' may be an integer from about 1 to about 15. In some of these embodiments, a' may be an integer from about 1 to about 10. In some of these embodiments, a' may be an integer from about 1 to about 8. In some of these embodiments, a' may be an integer from about 1 to about 6. In some of these embodiments, a' may be an integer from about 2 to about 20. In some of these embodiments, a' may be an integer from about 5 to about 20. In some of these embodiments, a' may be an integer from about 10 to about 20. In some of these embodiments, a' may be an integer from about 6 to about 12.

As will be described in more detail below, in one or more embodiments of the present invention, it has been found that the addition of a catechol functional group to the side chain of one or more of the amino acid residues in one or more of the amino acid-based polyester segments substantially improves the adhesive properties of the amino acid-based adhesives of the present invention. In some embodiments, the catechol functional groups may be separated from the side chains of the amino acid residues by from 1 to 6 carbon atoms. In some embodiments, the catechol functional groups may be separated from the side chains of the amino acid residues by from 2 to 5 carbon atoms. In some embodiments, the catechol functional groups may be separated from the side chains of the amino acid residues by from 2 to 4 carbon atoms. In some embodiments, the catechol functional groups may be separated from the side chains of the amino acid residues by 3 carbon atoms.

These catechol functional group are preferably joined to the side chain of a tyrosine residue. As will be discussed in more detail below, in some of these embodiments, the catechol functional group may be functionalized to include contain a carboxyl end group and then joined to the phenol group of a tyrosine residue by means of an ester bond between the phenol group of the tyrosine residue and the carboxyl end group of the functionalized catechol group.

In some embodiments, the catechol functionalized amino acid-based polyester segments of the amino acid-based PUE adhesives of the present invention may have the formula:

(I)

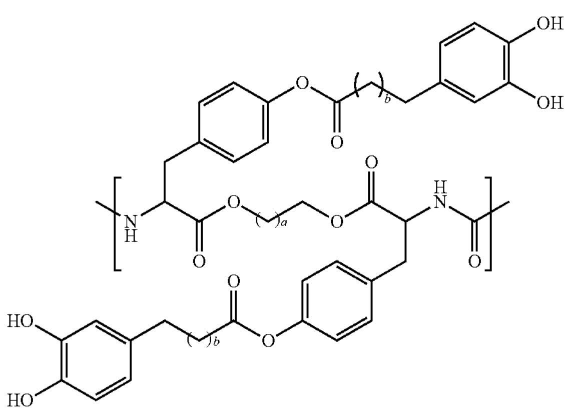

wherein a is an integer from 1 to 20 and b is an integer from 1 to 6. In some of these embodiments, a may be an integer from about 4 to about 20. In some of these embodiments, a may be an integer from about 8 to about 20. In some of these embodiments, a may be an integer from about 12 to about 20. In some of these embodiments, a may be an integer from about 2 to about 15. In some of these embodiments, a may be an integer from about 2 to about 10. In some of these embodiments, a may be an integer from about 4 to about 15. In some of these embodiments, a may be 8. In some of these embodiments, b may be an integer from about 1 to about 6. In some of these embodiments, b may be an integer from about 2 to about 4. In some of these embodiments, b may be an integer from about 3 to about 5. In some of these embodiments, b may be 3.

As will be described in more detail below, the amino acid-based PEU adhesives of various embodiments of the present invention may be a copolymer prepared from two or more different counter-ion protected amino acid-based polyester monomers. In these embodiments, each counter-ion protected monomer is ordinarily prepared from a single type of amino acid and single type of diol or polyol as to create a PEU segment having known and/or predictable qualities. By carefully selecting each of these monomers and controlling their ratio in the PEU copolymer, the mechanical, adhesive, degradation, solubility based methods of delivery, and other properties of the amino acid-based PEU adhesives of various embodiments of the present invention may be controlled and/or tuned.

Accordingly, in one or more embodiments of the present invention, the amino acid-based PEU adhesives may be a copolymer comprised of two or more different types of amino acid-based polyester segments, each type of polyester segment being the residue of a different monomer used to form the PEU. As used herein, reference to a particular "type" of amino acid-based polyester segment is intended to refer to one or more amino acid-based polyester segments formed from the same counter-ion protected amino acid-based polyester monomer and having identical structure and function.

In some embodiments of the present invention, the amino acid-based PEU adhesives may comprise a copolymer having a first type of amino acid-based polyester segment that has relatively good adhesive properties (hereinafter "first segment" or "first segments") and a second type of amino acid-based polyester segment (hereinafter "second segment" or "second segments") that has other desirable qualities such as elasticity, degradability, and/or methods of application or delivery, as set for the above. As used herein, the term "adhesive properties" refers to the ability of an amino acid-based polyester segment to adhere to the surface of another substance. Likewise, an amino acid-based polyester segment that has better adhesive properties than many or most of the other amino acid-based polyester segments described herein, may be said to have "good adhesive properties" or "relatively good adhesive properties." In general, it has been found that amino acid-based polyester segments having residues of amino acids having side chains with the ability to form hydrogen bonds tend to have better adhesive properties. While not wishing to be bound by theory, it is believed that these amino acids have better adhesive qualities because the form hydrogen bonds with other substances. In some embodiments, amino acid-based polyester segments having good adhesive properties may include those having one or more phenylalanine and/or tyrosine residues. In some embodiments, amino acid-based polyester segments having good adhesive properties may include segments in which one or more of the amino acid residues has been functionalized to include a catechol group.

In some of these embodiments, the first segments may comprise two or more residues of amino acids having particularly good adhesive properties, such as tyrosine or phenylalanine, or a catechol functionalized amino acid, as described above. In some embodiments, the first segments may comprise the residue of two phenylalanine molecules separated by from about 2 to about 20 carbon atoms. In some embodiments, the first segments may comprise the residue of two phenylalanine molecules separated by from about 2 to about 15 carbon atoms. In some embodiments, the first segments may comprise the residue of two phenylalanine molecules separated by from about 2 to about 12 carbon atoms. In some embodiments, the first segments may comprise the residue of two phenylalanine molecules separated by from about 4 to about 20 carbon atoms. In some embodiments, the first segments may comprise the residue of two phenylalanine molecules separated by from about 4 to about 15 carbon atoms. In some embodiments, the first segments may comprise the residue of two phenylalanine molecules separated by from about 4 to about 10 carbon atoms. In some embodiments, the first segments may comprise the residue of two phenylalanine molecules separated by from about 10 to about 20 carbon atoms. In some embodiments, the first segments may comprise the residue of two phenylalanine molecules separated by from about 6 to about 12 carbon atoms. In some embodiments, the first segments may comprise the residue of two phenylalanine molecules separated by 8 carbon atoms.

In some embodiments, the first segments may comprise the residue of two tyrosine molecules separated by from about 2 to about 20 carbon atoms. In some embodiments, the first segments may comprise the residue of two tyrosine molecules separated by from about 2 to about 15 carbon atoms. In some embodiments, the first segments may comprise the residue of two tyrosine molecules separated by from about 2 to about 12 carbon atoms. In some embodiments, the first segments may comprise the residue of two tyrosine molecules separated by from about 4 to about 20 carbon atoms. In some embodiments, the first segments may comprise the residue of two tyrosine molecules separated by from about 4 to about 15 carbon atoms. In some embodiments, the first segments may comprise the residue of two tyrosine molecules separated by from about 4 to about 10 carbon atoms. In some embodiments, the first segments may comprise the residue of two tyrosine molecules separated by from about 10 to about 20 carbon atoms. In some embodiments, the first segments may comprise the residue of two tyrosine molecules separated by from about 6 to about 12 carbon atoms. In some embodiments, the first segments may comprise the residue of two tyrosine molecules separated by 8 carbon atoms.

In some embodiments, the first segments of the amino acid-based PEU adhesives of the present invention may comprise two or more catechol functionalized amino acids separated by from about 2 to about 20 carbon atoms. In some of these embodiments, the two or more catechol functionalized amino acids may be separated from each other by from about 2 to about 15 carbon atoms. In some of these embodiments, the two or more catechol functionalized amino acids may be separated from each other by from about 2 to about 10 carbon atoms. In some of these embodiments, the two or more catechol functionalized amino acids may be separated from each other by from about 10 to about 20 carbon atoms. In some of these embodiments, the two or more catechol functionalized amino acids may be separated from each other by from about 4 to about 20 carbon atoms. In some of these embodiments, the two or more catechol functionalized amino acids may be separated from each other by from about 6 to about 12 carbon atoms. In some of these embodiments, the two or more catechol functionalized amino acids may be separated from each other by about 8 carbon atoms.

In some embodiments, the catechol functional groups may be separated from the side chains of the amino acid residues by from 1 to 6 carbon atoms. In some embodiments, the catechol functional groups may be separated from the side chains of the amino acid residues by from 2 to 6 carbon atoms. In some embodiments, the catechol functional groups may be separated from the side chains of the amino acid residues by from 3 to 6 carbon atoms. In some embodiments, the catechol functional groups may be separated from the side chains of the amino acid residues by from 3 to 5 carbon atoms. In some embodiments, the catechol functional groups may be separated from the side chains of the amino acid residues by from 2 to 5 carbon atoms. In some embodiments, the catechol functional groups may be separated from the side chains of the amino acid residues by from 2 to 4 carbon atoms. In some embodiments, the catechol functional groups may be separated from the side chains of the amino acid residues by 3 carbon atoms.

In some embodiments, the first segments of the amino acid-based PEU adhesives of the present invention may have the formula:

(XXIII)

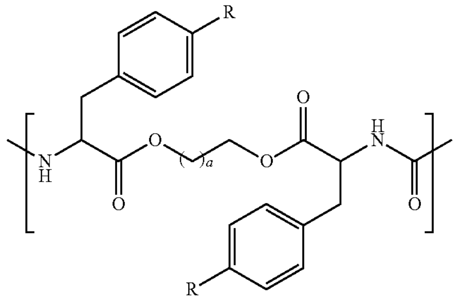

wherein R is H, OH, or —$OCOO(CH_2)_2C_6H_3(OH)_2$; and a is an integer from about 1 to about 20. In some of these embodiments, a may be an integer from about 1 to about 15. In some of these embodiments, a may be an integer from about 1 to about 10. In some of these embodiments, a may be an integer from about 15 to about 20. In some of these embodiments, a may be an integer from about 10 to about 20. In some of these embodiments, a may be an integer from about 2 to about 15. In some of these embodiments, a may be an integer from about 2 to about 12. In some of these embodiments, a may be an integer from about 4 to about 12. In some of these embodiments, a may be an integer from about 6 to about 14. In some of these embodiments, a may be 8. In some of the embodiments, b may be an integer from 1 to 6.

In some embodiments, the first segments may have the formula:

(I)

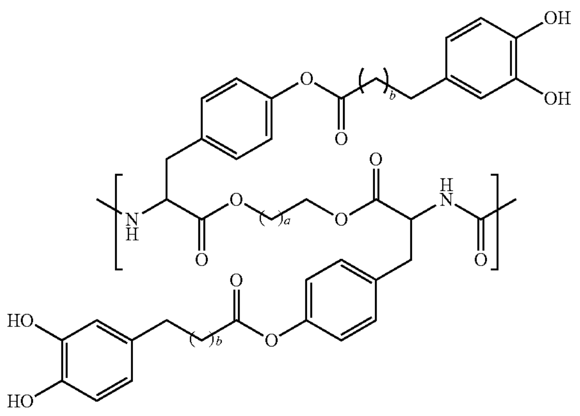

wherein a is an integer from 1 to 20 and b is an integer from about 1 to about 6. In some of these embodiments, a may be an integer from about 1 to about 15. In some of these embodiments, a may be an integer from about 1 to about 10. In some of these embodiments, a may be an integer from about 2 to about 20. In some of these embodiments, a may be an integer from about 2 to about 15. In some of these embodiments, a may be an integer from about 4 to about 12. In some of these embodiments, a may be an integer from about 6 to about 12. In some of these embodiments, a may be 8. In some of the embodiments, b may be an integer from 1 to 5. In some of the embodiments, b may be an integer from 3 to 5. In some of the embodiments, b may be 1.

In some of these embodiments, the first segments may comprise a molar fraction of from about 0.01 to about 0.3 of the amino acid-based PEU adhesives of the present invention. It has been found that if the mole fraction of the first segments is too high (over about 30%) self-adhesion between first segments in different parts of the PEU can become a significant factor reducing the adhesiveness of the amino acid-based PEU adhesives of the present invention. In some of these embodiments, the molar fraction of first segments of the amino acid-based PEU adhesives of the present invention may be from about 0.01 to about 0.2. In some of these embodiments, the molar fraction of first segments in the amino acid-based PEU adhesives of the present invention may be from about 0.01 to about 0.15. In some of these embodiments, the molar fraction of first segments in the amino acid-based PEU adhesives of the present invention may be from about 0.01 to about 0.10. In some of these embodiments, the molar fraction of first segments in the amino acid-based PEU adhesives of the present invention may be from about 0.01 to about 0.05. In some of these embodiments, the molar fraction of first segments in the amino acid-based PEU adhesives of the present invention may be from about 0.05 to about 0.20. In some of these embodiments, the molar fraction of first segments in the amino acid-based PEU adhesives of the present invention may be from about 0.05 to about 0.15. In some of these embodiments, the molar fraction of first segments in the amino acid-based PEU adhesives of the present invention may be from about 0.05 to about 0.10. In some of these embodiments, the molar fraction of first segments in the amino acid-based PEU adhesives of the present invention may be 0.10. In some of these embodiments, the molar fraction of first segments in the amino acid-based PEU adhesives of the present invention may be 0.05.

As set forth above, the amino acid-based PEU adhesives of the present invention may also comprise one or more second segments. In some of these embodiments, the second segments may comprise the bulk of the amino acid-based PEU adhesive and are intended to provide the desired mechanical, adhesive, thermal, degradation, solubility based methods of delivery, and other properties to the amino acid-based PEU adhesives of the present invention. As set forth above, by varying the amino acid residues, polyol residues, and mole fraction of the second segments, these polymers can be synthesized to have specific mechanical, adhesive, thermal, degradation, and solubility properties for targeted applications.

In some embodiments, the second segments of these amino acid-based PEU adhesives may comprise the residues of any two or more α-amino acid (other than proline) separated by 2 to 20 carbon atoms, as set forth above. In some embodiments, the two or more amino acid residues of the second segments may be residues of alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), serine (ser S), threonine (thr—T), tryptophan (trp—W), valine (val—V), or any combinations or derivatives thereof. In some embodiments, the second segments of these amino acid-based PEU adhesives may comprise the residues of two leucine molecules.

In some embodiments, the two or more amino acid residues of the second segments may be separated by from about 2 to about 15 carbon atoms. In some embodiments, the two or more amino acid residues of the second segments may be separated by from about 2 to about 12 carbon atoms. In some embodiments, the two or more amino acid residues of the second segments may be separated by from about 2 to about 10 carbon atoms. In some embodiments, the two or more amino acid residues of the second segments may be separated by from about 10 to about 20 carbon atoms. In some embodiments, the two or more amino acid residues of the second segments may be separated by from about 4 to about 15 carbon atoms. In some embodiments, the two or more amino acid residues of the second segments may be separated by from about 6 to about 12 carbon atoms. In some embodiments, the two or more amino acid residues of the second segments may be separated by 8 carbon atoms.

In some embodiments, the mole fraction of second segments in the amino acid-based PEU adhesives of the present invention may be from about 0.70 to about 0.99. In some embodiments, the mole fraction of second segments in the amino acid-based PEU adhesives of the present invention may be from about 0.80 to about 0.99. In some embodiments, the mole fraction of second segments in the amino acid-based PEU adhesives of the present invention may be from about 0.85 to about 0.99. In some embodiments, the mole fraction of second segments in the amino acid-based PEU adhesives of the present invention may be from about 0.85 to about 0.98. In some embodiments, the mole fraction of second segments in the amino acid-based PEU adhesives of the present invention may be from about 0.85 to about 0.95. In some embodiments, the mole fraction of second segments in the amino acid-based PEU adhesives of the present invention may be from about 0.90 to about 0.99. In some embodiments, the mole fraction of second segments in the amino acid-based PEU adhesives of the present invention may be from about 0.90 to about 0.98. In some embodiments, the mole fraction of second segments in the amino acid-based PEU adhesives of the present invention may be from about 0.95 to about 0.99. In some embodiments, the mole fraction of second segments in the amino acid-based PEU adhesives of the present invention may be from about 0.90 to about 0.98. In some embodiments, the mole fraction of second segments in the amino acid-based PEU adhesives of the present invention may be about 0.90. In some embodiments, mole fraction of second segments in the amino acid-based PEU adhesives of the present invention may be about 0.95.

In some embodiments, the second segments of the present invention may have the formula:

(II)

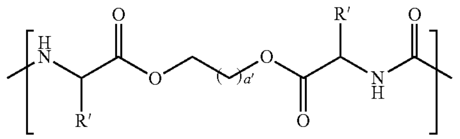

wherein R' is $—CH_3$, $—(CH_2)_3NHC(NH_2)C{=}NH$, $—CH_2CONH_2$, $—CH_2COOH$, $—CH_2SH$, $—(CH_2)_2COOH$, $—(CH_2)_2CONH_2$, $—NH_2$, $—CH_2C{=}CH—N{=}CH—NH$, $—CH(CH_3)CH_2CH_3$, $—CH_2CH(CH_3)_2$, $—(CH_2)_4NH_2$, $—(CH_2)_2SCH_3$, $—CH_2Ph$, $—CH_2OH$, $—CH(OH)CH_3$, $—CH_2—C{=}CH—NH\text{-}Ph$, $—CH_2\text{-}Ph\text{-}OH$, or $—CH(CH_3)_2$; and a' is an integer from 1 to 20. In some of these embodiments, a' may be an integer from about 1 to about 15.

In some of these embodiments, a' may be an integer from about 1 to about 10. In some of these embodiments, a' may be an integer from about 10 to about 20. In some of these embodiments, a' may be an integer from about 2 to about 15.

embodiments, be comprised of more than one type of segments, each having good adhesive properties.

In some embodiments, the amino acid-based PEU adhesives of the present invention may have the formula:

(III)

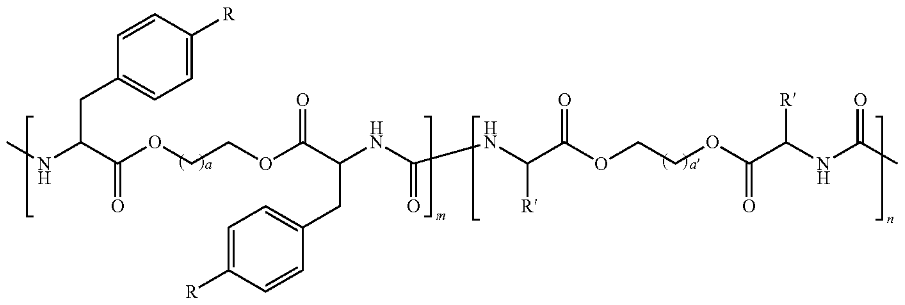

In some of these embodiments, a' may be an integer from about 2 to about 12. In some of these embodiments, a' may be an integer from about 4 to about 12. In some of these embodiments, a' may be an integer from about 6 to about 12. In some of these embodiments, a' may be 8.

As set forth above, amino acid-based PEU adhesives of the present invention may in some embodiments be copolymers of the first segments, second segments, and a PEU forming compound such as phosgene, diphosgene or triphosgene. In some embodiments, the mole fraction of first segments in the amino acid-based PEU adhesives of the present invention may be from about 0.01 to about 0.3 and the mole fraction of the second segments in the amino acid-based PEU adhesives of the present invention may be from about 0.70 to about 0.99. In some embodiments, the mole fraction of first segments in the amino acid-based PEU adhesives of the present invention may be from about 0.20 to about 0.30 and the mole fraction of the second segments in the amino acid-based PEU adhesives of the present invention may be from about 0.70 to about 0.80. In some embodiments, the mole fraction of first segments in the amino acid-based PEU adhesives of the present invention may be from about 0.15 to about 0.20 and the mole fraction of the second segments in the amino acid-based PEU adhesives of the present invention may be from about 0.80 to about 0.85. In some embodiments, the mole fraction of first segments in the amino acid-based PEU adhesives of the present invention may be about 0.10 and the mole fraction of the second segments in the amino acid-based PEU adhesives of the present invention may be about 090. In some embodiments, the mole fraction of first segments in the amino acid-based PEU adhesives of the present invention may be about 0.05 and the mole fraction of the second segments in the amino acid-based PEU adhesives of the present invention may be about 095.

While these second segments have been described herein as a single type of segment, it should be appreciated that in some embodiments of the present invention, the "second segments" could include more than one type of segment, providing various different combinations of mechanical, adhesive, degradation, solubility, and other properties, as described above. Likewise, the first segments may, in same wherein R is H, OH, or $—OCOO(CH_2)_2C_6H_3(OH)_2$; R' is $—CH_3$, $—(CH_2)_3NHC(NH_2)C{=}NH$, $—CH_2CONH_2$, $—CH_2COOH$, $—CH_2SH$, $—(CH_2)_2COOH$, $—(CH_2)_2CONH_2$, —NH, $—CH_2C{=}CH—N{=}CH—NH$, $—CH(CH_3)CH_2CH_3$, $—CH_2CH(CH_3)_2$, $—(CH_2)_4NH_2$, $—(CH_2)_2SCH_3$, $—CH_2Ph$, $—CH_2OH$, $—CH(OH)(CH_3$, $—CH_2—C{=}CH—NH\text{-}Ph$, $—CH_2\text{-}Ph\text{-}OH$, or $—CH(CH_3)_2$; a and a' are each an integer from about 1 to about 20; and m and n are mole fractions.

In some of these embodiments, m is a mole fraction from about 0.1 to about 0.30. In some of these embodiments, m is a mole fraction from about 0.01 to about 0.20. In some of these embodiments, m is a mole fraction from about 0.01 to about 0.15. In some of these embodiments, m is a mole fraction from about 0.01 to about 0.10. In some of these embodiments, m is a mole fraction from about 0.5 to about 0.10. In some of these embodiments, n is a mole fraction from about 0.70 to about 0.99. In some of these embodiments, n is a mole fraction from about 0.80 to about 0.99. In some of these embodiments, n is a mole fraction from about 0.85 to about 0.99. In some of these embodiments, n is a mole fraction from about 0.90 to about 0.99. In some of these embodiments, n is a mole fraction from about 0.90 to about 0.95. In some of these embodiments, a and a' are each integers from 1 to 20. In some of these embodiments, a and a' are each integers from 1 to 15. In some of these embodiments, a and a' are each integers from 1 to 12. In some of these embodiments, a and a' are each integers from 10 to 20. In some of these embodiments, a and a' are each integers from 4 to 12. In some of these embodiments, a and a' are each integers from 6 to 12. In some of these embodiments, a and a' are both 8.

In some embodiments, the amino acid-based PEU adhesives of the present invention may have the formula:

(IV)
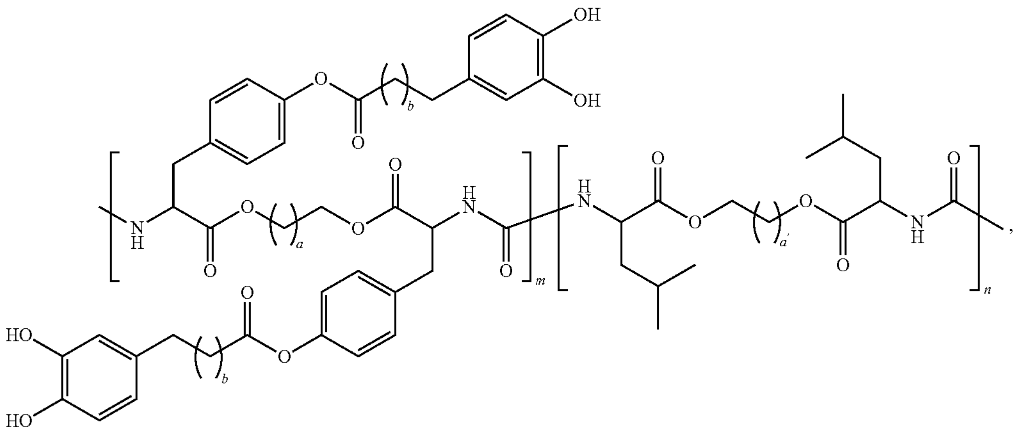
,
(V)
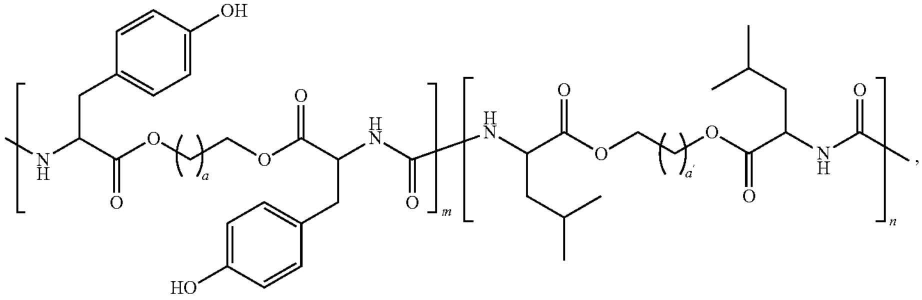
,
(VI)
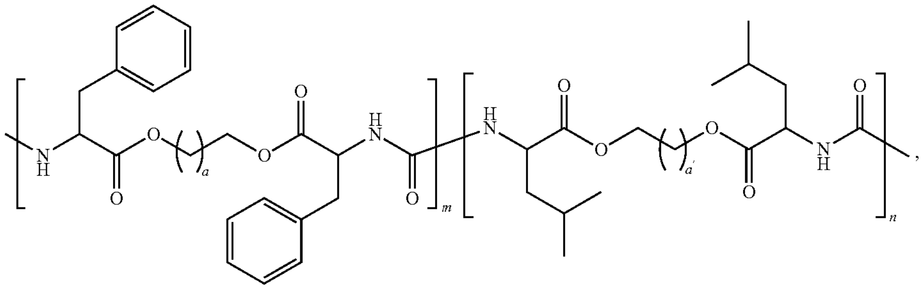
,
(VII)
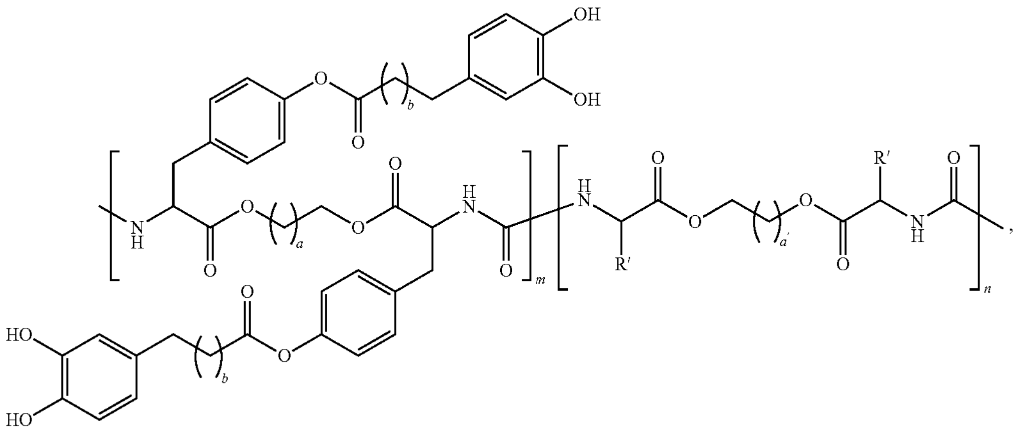
,

-continued
(VIII)
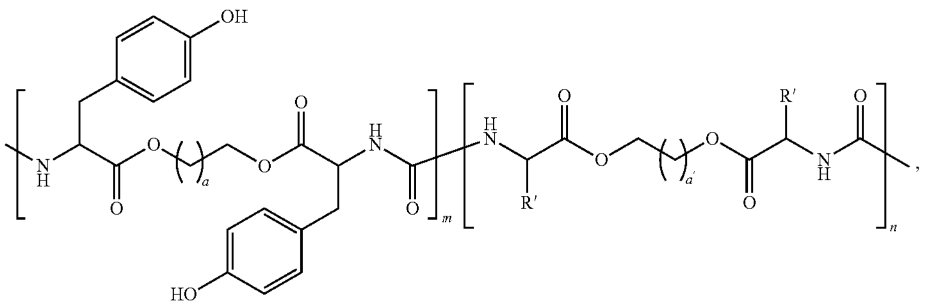
(IX)
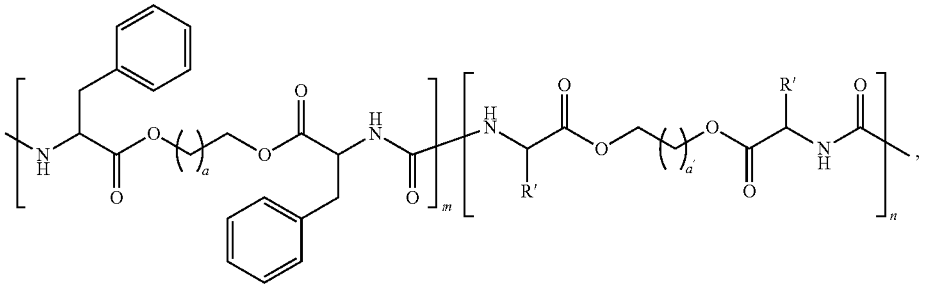
(X)
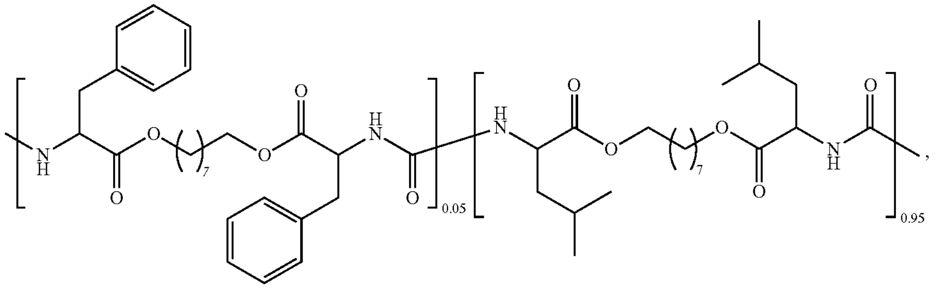
(XI)
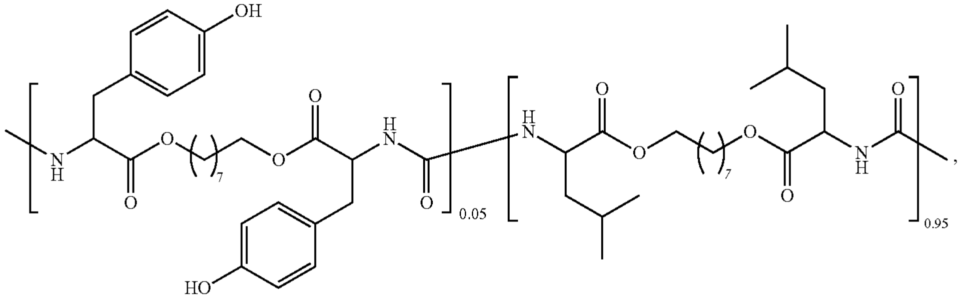
(XII)
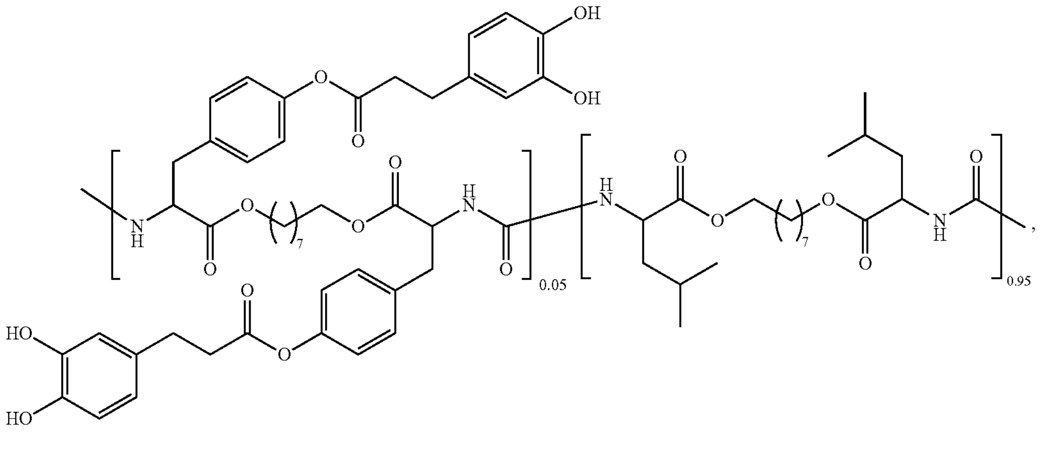

-continued
(XIII)
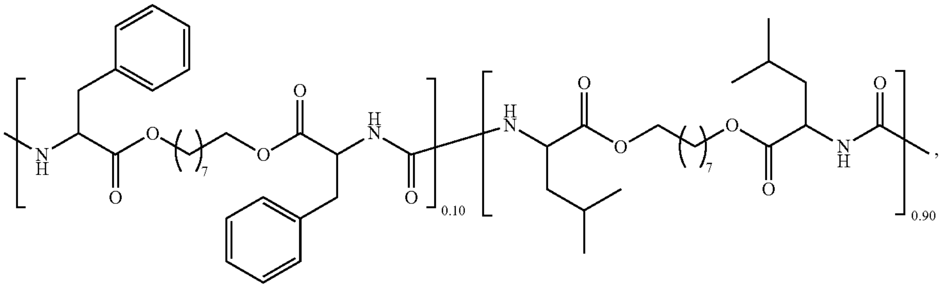
(XIV)
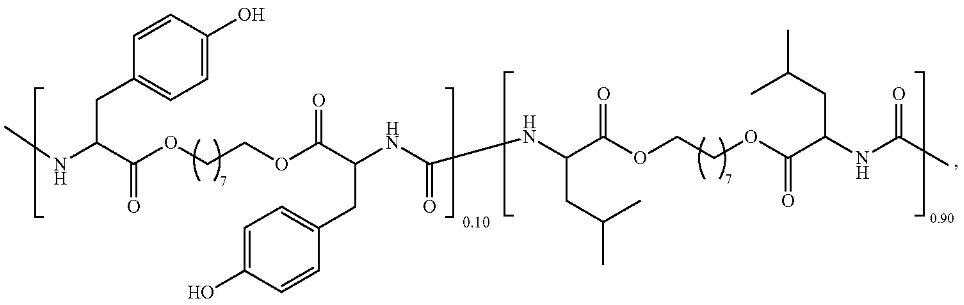
(XV)
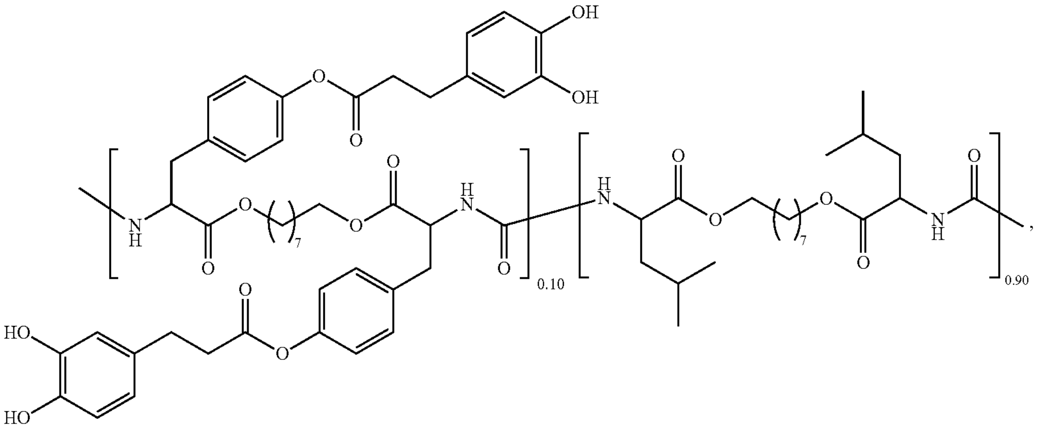
(XVI)
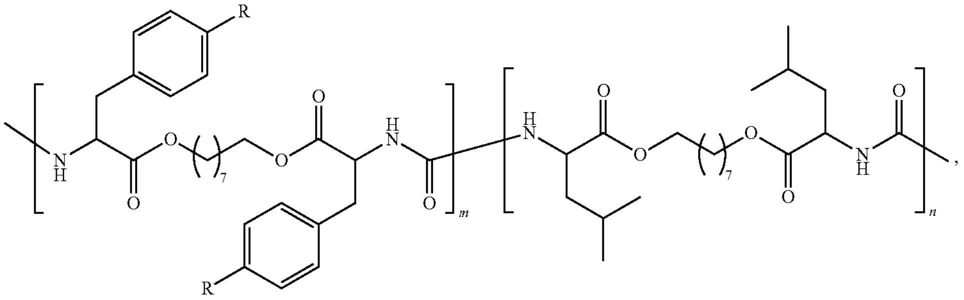
(XVII)
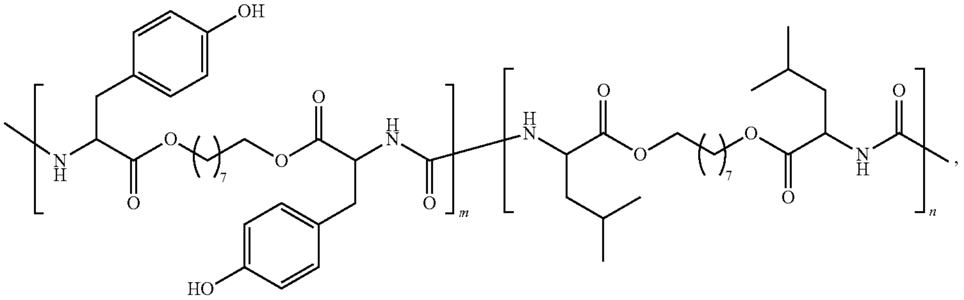

-continued (XVIII)

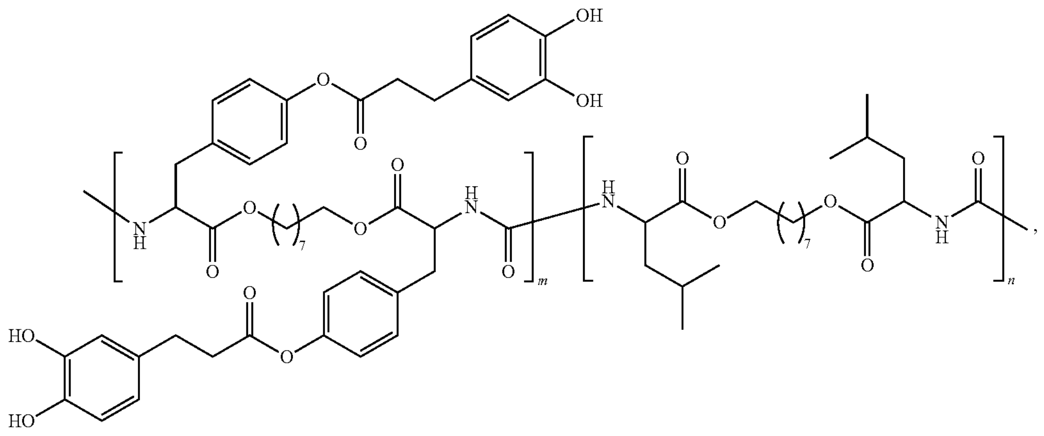

, or (XIX)

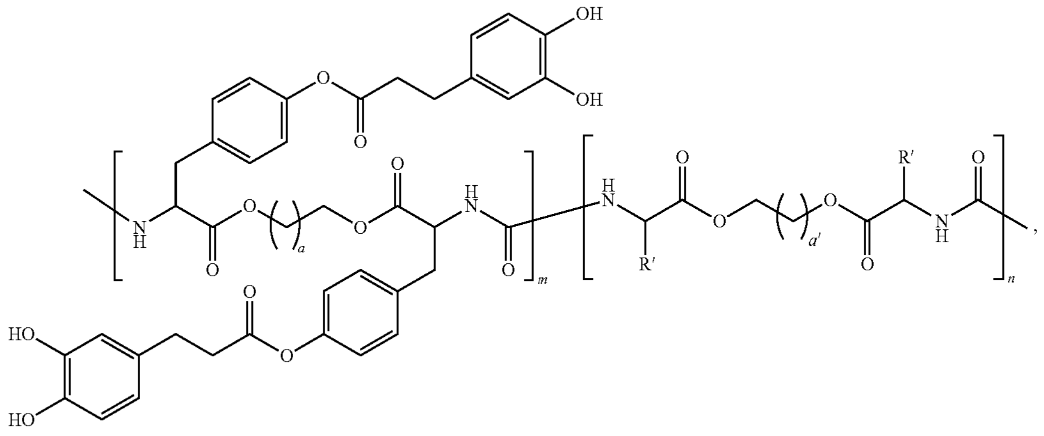

, wherein R' is $-CH_3$, $-(CH_2)_3NHC(NH_2)C{=}NH$, $-CH_2CONH_2$, $-CH_2COOH$, $-CH_2SH$, $(CH_2)_2COOH$, $-(CH_2)_2CONH_2$, $-NH_2$, $-CH_2C{=}CH-N{=}CH-NH$, $-CH(CH_3)CH_2CH_3$, $-CH_2CH(CH_3)_2$, $-(CH_2)_4NH_2$, $-(CH_2)_2SCH_3$, $-CH_2Ph$, $-CH_2OH$, $-CH(OH)CH_3$, $-CH_2-C{=}CH-NH-Ph$, $-CH_2$-Ph-OH, or $-CH(CH_3)_2$; a and a' are each integers from 1 to 20; b is an integer from 1 to 6; m is a mole fraction from 0.01 to 0.30; and n is a mole fraction from 0.70 to 0.99.

In some of these embodiments, m is a mole fraction from about 0.01 to about 0.25. In some of these embodiments, m is a mole fraction from about 0.01 to about 0.20. In some of these embodiments, m is a mole fraction from about 0.01 to about 0.15. In some of these embodiments, m is a mole fraction of about 0.05. In some of these embodiments, m is a mole fraction of about 0.10. In some of these embodiments, n is a mole fraction from about 0.70 to about 0.99. In some of these embodiments, n is a mole fraction from about 0.80 to about 0.99. In some of these embodiments, n is a mole fraction from about 0.85 to about 0.99. In some of these embodiments, n is a mole fraction of about 0.90. In some of these embodiments, n is a mole fraction of about 0.95. In some of these embodiments, a and a' are each integers from 1 to 20. In some of these embodiments, a and a' are each integers from 1 to 15. In some of these embodiments, a and a' are each integers from 1 to 10. In some of these embodiments, a and a' are each integers from 10 to 20. In some of these embodiments, a and a' are each integers from 2 to 15. In some of these embodiments, a and a' are each integers from 4 to 12. In some of these embodiments, a and a' are each integers from 6 to 12. In some of these embodiments, a and a' are both 8.

In some embodiments, the amino acid-based PEU adhesives of the present invention may further comprise comprising one or more oxidative cross linkers. Suitable oxidative cross linkers may include, without limitation, tetrabutyl ammonium periodate ($N(C_4H_9)_4(IO_4)$), $IO_4^-$, tetrapropyl ammonium periodate, tetrapentyl ammonium periodate, tetrahexyl ammonium periodate, tetraoctyl ammonium periodate, or any other suitable oxidant. While not wishing to be bound by theory, it is believed that oxidants, such as periodate form bonds with the catechol groups increasing adhesiveness through self binding at lower concentrations. At higher concentrations, however, oxidants, such as periodate were found to form interchain cross links, thereby reducing adhesiveness.

As will be discussed in greater detail in the Experimental section to follow, basic physical and other properties were tested for amino-acid-based PEU adhesives according to various embodiments of the present invention having the following structures:

5% Phe (X)
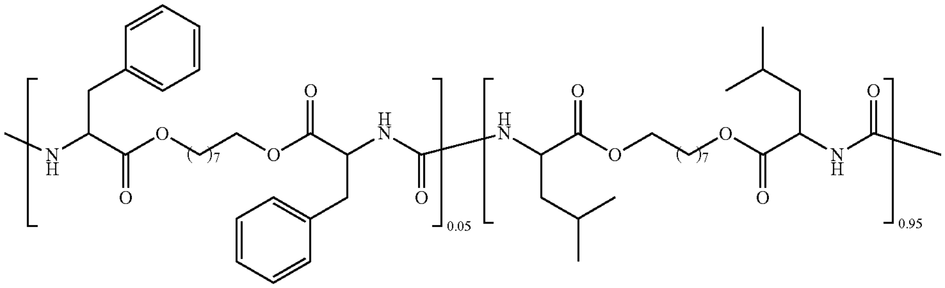
5% Tyr (XI)
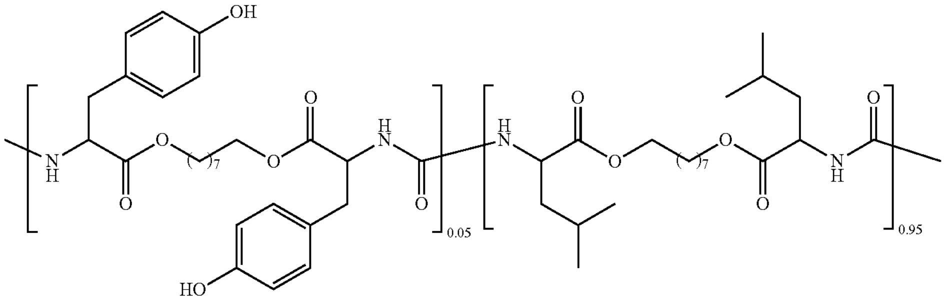
5% CA(AN) (XXI)
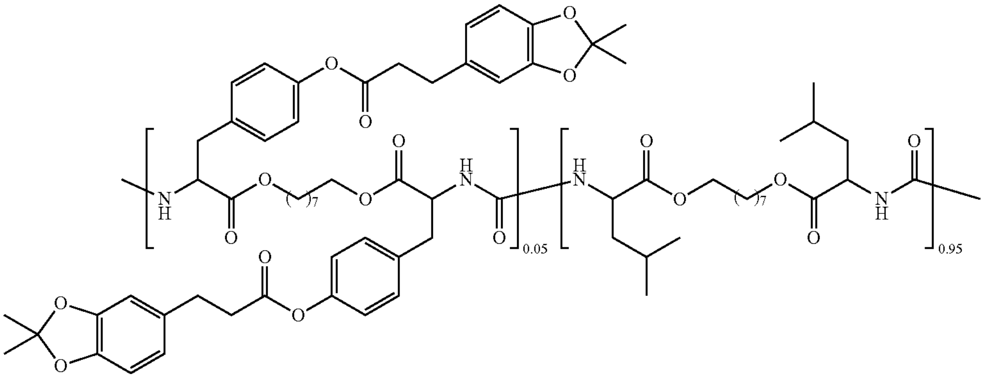
5% CA (XII)
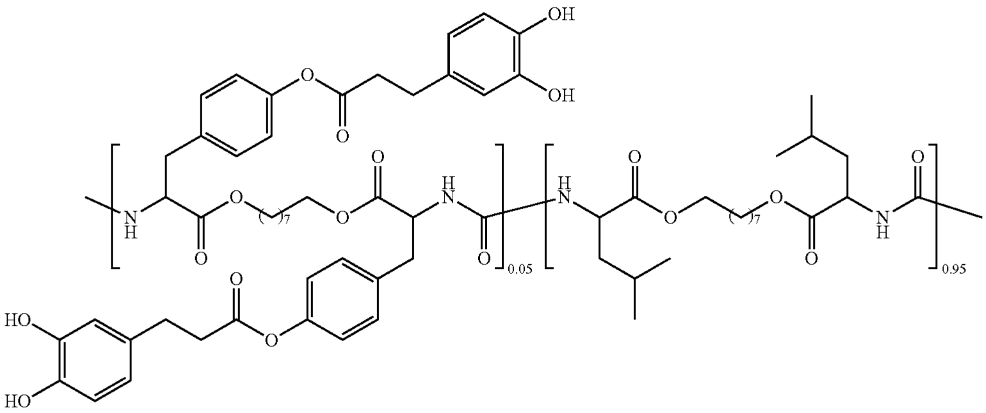

-continued
10% Phe (XIII)
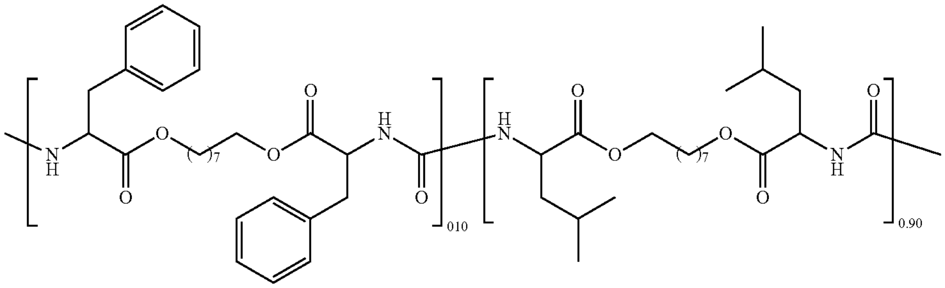
10% Tyr (XIV)
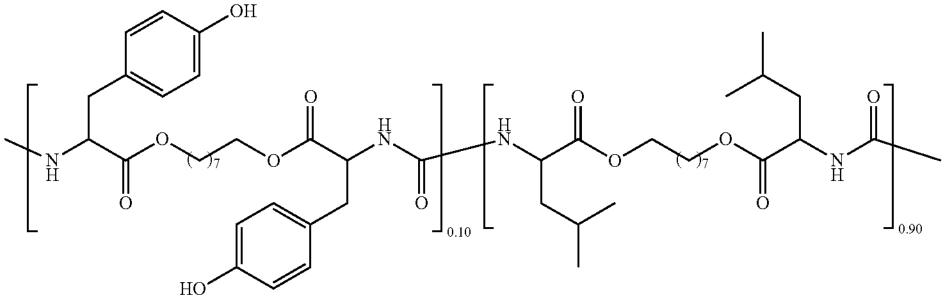
10% CA(AN) (XXII)
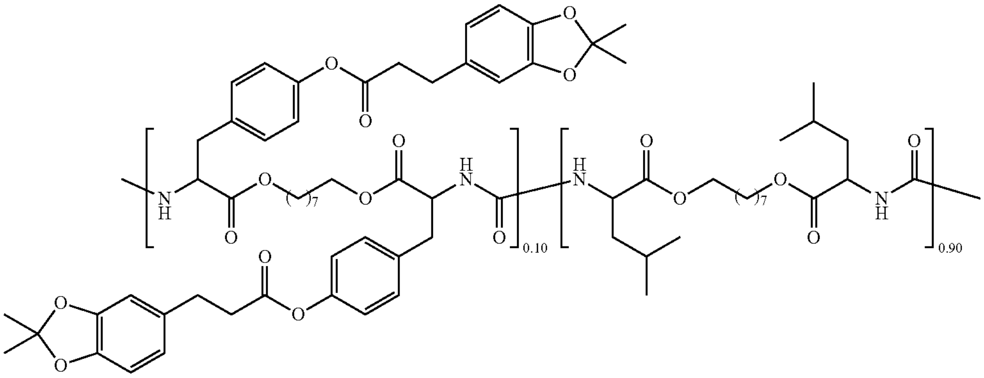
10% CA (XV)
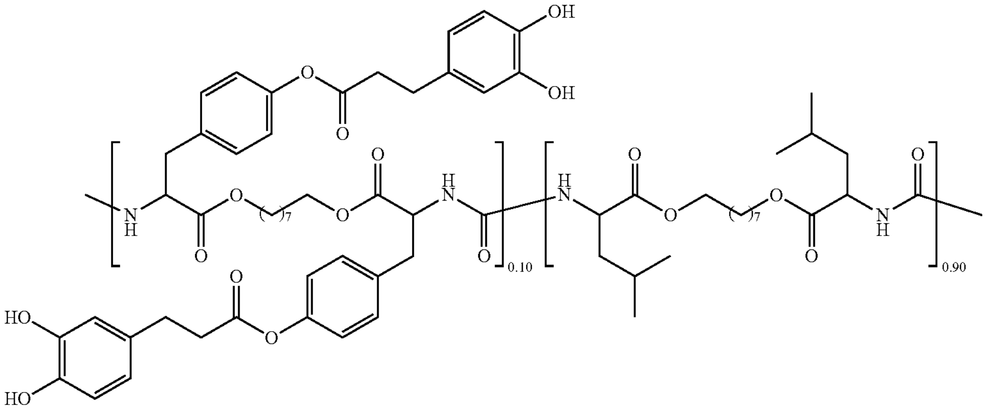

In some embodiments, these acid-based PEU adhesives may have the physical properties, including molecular mass ($M_n$ and $M_w$), molecular mass distribution ($Đ_M$), glass transition temperature ($T_g$) and thermal decomposition temperature ($T_d$), set forth in Table 1, below.

TABLE 1

| | $M_n$[a] (kDa) | $M_w$[b] (kDa) | $Đ_M$[c] | $T_d$[d] (° C.) | $T_g$[e] (° C.) |
|---|---|---|---|---|---|
| 5% Phe | 84.8 | 98.3 | 1.16 | 282 | 36.5 |
| 5% Tyr | 70.6 | 142.3 | 2.02 | 258 | 40.0 |
| 5% CA(AN) | 72.5 | 90.1 | 1.24 | | |
| 5% CA | / | / | / | 267 | 36.4 |
| 10% Phe | 56.7 | 68.8 | 1.22 | 282 | 37.3 |
| 10% Tyr | 51.7 | 71.3 | 1.38 | 262 | 29.2 |
| 10% CA(AN) | 66.0 | 93.5 | 1.42 | | |
| 10% CA | / | / | / | 282 | 44.5 |

[a]Number-average molecular mass.
[b]Weight-average molecular mass.
[c]Molecular mass distribution $Đ_M = M_w/M_n$. This was obtained after polymer precipitation, which narrows the molecular mass distribution comparing which is theoretically expected in a step growth polymerization.
[d]Decomposition temperature (5% weight loss) determined by thermal gravimetric analysis (TGA) under $N_2$.
[e]Glass transition temperature determined by DSC.

The number average molecular mass ($M_n$) of the PEU based adhesives of various embodiments of the present invention is generally in 50 kDa to 150 kDa range, and the molecular mass distribution is generally between 1.1 and 2.0.

Size Exclusion Chromatography (SEC) data could not obtained for the catechol containing polymers because of their likely adhesion onto the high surface area SEC column. To demonstrate that the PEU backbone was stable under the deprotection condition and the molecular mass of acetonide protected catechol polymers could be used for comparison of catechol containing PUEs, a 5% tyrosine PEU was put under the deprotection reaction condition and subject to SEC analysis at different reaction times. Almost no decrease in molecular mass was observed up to 2 h (Table 2).

TABLE 2

Molecular weight analysis of 5% Tyr and the products at different reaction times under the deprotection condition.

| | $M_n$[a] (kDa) | $M_w$[b] (kDa) | $Đ_M$[c] |
|---|---|---|---|
| 5% Tyr | 49.6 | 63.1 | 1.27 |
| 40 min | 57.1 | 68.5 | 1.20 |
| 80 min | 48.4 | 56.9 | 1.17 |
| 120 min | 50.6 | 60.0 | 1.19 |

[a]Number-averaged molecular weight.
[b]Weight-averaged molecular weight.
[c]Molecular weight distribution $Đ_M = M_w/M_n$.

Accordingly, the $M_w$, $M_n$ and $Đ_M$ of the amino acid-based PEU polymers having acetonide protected catechol groups may be used to provide relative $M_w$, $M_n$ and/or $Đ_M$ data for unprotected catechol functionalized embodiments of the amino acide-based PEU adhesives of the present invention. In some embodiments, catechol functionalized PEU adhesives of the present invention may be formed from a corresponding acetonide protected catechol functionalized PEU having a $M_n$ of from about 40 kDa to about 150 kDa. In some embodiments, the catechol functionalized PEU adhesives of the present invention may be formed from a corresponding acetonide protected catechol functionalized PEU having a $M_n$ of from about 40 kDa to about 125 kDa. In some embodiments, the catechol functionalized PEU adhesives of the present invention may be formed from a corresponding acetonide protected catechol functionalized PEU having a $M_n$ of from about 50 kDa to about 100 kDa. In some embodiments, the catechol functionalized PEU adhesives of the present invention may be formed from a corresponding acetonide protected catechol functionalized PEU having a $M_n$ of from about 50 kDa to about 75 kDa. In some embodiments, the catechol functionalized PEU adhesives of the present invention may be formed from a corresponding acetonide protected catechol functionalized PEU having a $M_n$ of from about 75 kDa to about 150 kDa. In some embodiments, the catechol functionalized PEU adhesives of the present invention may be formed from a corresponding acetonide protected catechol functionalized PEU having a $M_n$ of from about 100 kDa to about 150 kDa. In some embodiments, the catechol functionalized PEU adhesives of the present invention may be formed from a corresponding acetonide protected catechol functionalized PEU having a $M_n$ of from about 125 kDa to about 150 kDa. In some embodiments, the catechol functionalized PEU adhesives of the present invention may be formed from a corresponding acetonide protected catechol functionalized PEU having a $M_n$ of from about 45 kDa to about 90 kDa.

In some embodiments, catechol functionalized PEUs adhesives of the present invention may be formed from a corresponding acetonide protected catechol functionalized PEU having a $M_w$ of from about 60 kDa to about 300 kDa. In some embodiments, the catechol functionalized PEU adhesives of the present invention may be formed from a corresponding acetonide protected catechol functionalized PEU having a $M_w$ of from about 60 kDa to about 250 kDa. In some embodiments, the catechol functionalized PEU adhesives of the present invention may be formed from a corresponding acetonide protected catechol functionalized PEU having a $M_w$ of from about 60 kDa to about 200 kDa. In some embodiments, the catechol containing PEU adhesives of the present invention may be formed from a corresponding acetonide protected catechol functionalized PEU having a $M_w$ of from about 60 kDa to about 150 kDa. In some embodiments, the catechol containing PEU adhesives of the present invention may be formed from a corresponding acetonide protected catechol functionalized PEU having a $M_w$ of from about 60 kDa to about 100 kDa. In some embodiments, the catechol containing PEU adhesives of the present invention may be formed from a corresponding acetonide protected catechol functionalized PEU having a $M_w$ of from about 60 kDa to about 300 kDa. In some embodiments, the catechol containing PEU adhesives of the present invention may be formed from a corresponding acetonide protected catechol functionalized PEU having a $M_w$ of from about 100 kDa to about 300 kDa. In some embodiments, the catechol containing PEU adhesives of the present invention may be formed from a corresponding acetonide protected catechol functionalized PEU having a $M_w$ of from about 150 kDa to about 300 kDa. In some embodiments, the catechol containing PEU adhesives of the present invention may be formed from a corresponding acetonide protected catechol functionalized PEU having a $M_w$ of from about 200 kDa to about 300 kDa. In some embodiments, the catechol containing PEU adhesives of the present invention may be formed from a corresponding acetonide protected catechol functionalized PEU having a $M_w$ of from about 250 kDa to about 300 kDa. In some embodiments, the catechol containing PEU adhesives of the present invention may be formed from a corresponding acetonide protected catechol functionalized PEU having a $M_w$ of from about 50 kDa to about 90 kDa.

As set forth above the molecular mass distribution ($Đ_M$) is equal to $M_w/M_n$. Again using the measured molecular mass ($M_n$ and $M_w$) of the corresponding acetonide protected catechol functionalized PEUs, an approximate $Đ_M$ of the catechol functionalized PUEs may be calculated for comparison. In some embodiments, the catechol functionalized PUEs may have an approximate $Đ_M$ ($M_w/M_n$ for the corresponding acetonide protected catechol functionalized PEU) of from about 1.1 to about 2.5. In some embodiments, the catechol functionalized PUEs may have an approximate $Đ_M$ ($M_w/M_n$ for the acetonide protected catechol functionalized PEU) of from about 1.1 to about 2.0. In some embodiments, the catechol functionalized PUEs may have an approximate $Đ_M$ ($M_w/M_n$ for the corresponding acetonide protected catechol functionalized PEU) of from about 1.1 to about 1.5. In some embodiments, the catechol functionalized PUEs may have an approximate $Đ_M$ ($M_w/M_n$ for the corresponding acetonide protected catechol functionalized PEU) of from about 1.5 to about 2.5. In some embodiments, the catechol functionalized PUEs may have an approximate $Đ_M$ ($M_w/M_n$ for the acetonide protected catechol functionalized PEU) of from about 2.0 to about 2.5. In some embodiments, the catechol functionalized PUEs may have an approximate $Đ_M$ ($M_w/M_n$ for the acetonide protected catechol functionalized PEU) of from about 2.0 to about 2.5.

As Table 1 indicates, the decomposition temperatures indicate all of the tested PEU-based polymer adhesives are stable up to 250° C. In some embodiments, the catechol functionalized PEU adhesives of the present invention may have a thermal decomposition temperature ($T_d$) of from about 250 to about 300. In some embodiments, the catechol functionalized PEU adhesives of the present invention may have a thermal decomposition temperature ($T_d$) of from about 250 to about 275. In some embodiments, the catechol functionalized PEU adhesives of the present invention may have a thermal decomposition temperature ($T_d$) of from about 275 to about 300. In some embodiments, the catechol functionalized PEU adhesives of the present invention may have a thermal decomposition temperature ($T_d$) of from about 250 to about 290.

Similarly, the glass transition temperatures of all of the PEUs shown in Table 1 above are above room temperature and in the range of from about 29° C. to about 45° C. In some embodiments, the catechol functionalized PEU adhesives of the present invention may have a glass transition temperature ($T_g$) of from about 20° C. to about 50° C. In some embodiments, the catechol functionalized PEU adhesives of the present invention may have a glass transition temperature ($T_g$) of from about 20° C. to about 40° C. In some embodiments, the catechol functionalized PEU adhesives of the present invention may have a glass transition temperature ($T_g$) of from about 20° C. to about 30° C. In some embodiments, the catechol functionalized PEU adhesives of the present invention may have a glass transition temperature ($T_g$) of from about 30° C. to about 50° C. In some embodiments, the catechol functionalized PEU adhesives of the present invention may have a glass transition temperature ($T_g$) of from about 40° C. to about 50° C.

In another aspect, the present invention is directed to one or more methods for making the amino acid-based PEU adhesives described above. In general outline, these amino acid-based PEU adhesives may be synthesized using a two or three step process comprising: (i) combining one or more amino acids and a linear or branched diol or polyol to form one or more counter-ion protected amino acid-based polyester monomers; (ii) forming an amino acid-based PEU by interfacial polymerization of these counter-ion protected amino acid-based polyester monomers with a PEU forming material like phosgene or triphosgene; and (iii), in some embodiments, post-polymerization functionalization of the resulting amino acid-based PEU with one or more catechol functional groups. (See generally, Examples 3-7, below.)

As set forth above, the amino acid or acids used to form the counter-ion protected amino acid-based polyester monomers may be any α-amino acid other than proline. In some embodiments, amino acid or acids used to form the counter-ion protected amino acid-based polyester monomers may be alanine (ala—A); arginine (arg—R); asparagine (asn—N); aspartic acid (asp—D); cysteine (cys—C); glutamine (gln—Q); glutamic acid (glu—E); glycine (gly—G); histidine (his—H); isoleucine (ile—I); leucine (leu—L); lysine (lys—K); methionine (met—M); phenylalanine (phe—F); serine (ser—S); threonine (thr—T); tryptophan (trp—W); tyrosine (tyr—Y); valine (val—V) or any combination or derivative thereof. In some embodiments, the amino acid or acids used to form the counter-ion protected amino acid-based polyester monomers may be a functionalized or protected α-amino acid. In some embodiments, amino acid or acids used to form the counter-ion protected amino acid-based polyester monomers may comprise one or more benzyl protected tyrosine molecules, tert-butyloxycarbonyl (BOC) protected tyrosine molecules.

In one or more of these embodiments, the amino acid or acids are reacted with a linear or branched polyol having from 2 to 60 carbon atoms and an acid to form a counter-ion protected amino acid-based polyester monomer. In some embodiments, the polyol may have from 2 to 40 carbon atoms. In some embodiments, the polyol may have from 2 to 20 carbon atoms. In some embodiments, the polyol may have from 2 to 10 carbon atoms. In some embodiments, the polyol may be a diol, triol, or tetraol. In some embodiments, the polyol may be a diol having from 2 to 20 carbon atoms. In some embodiments, the polyol is a diol having from 2 to 17 carbon atoms. In some embodiments, the polyol is a diol having from 2 to 13 carbon atoms. In some embodiments, the polyol is a diol having from 2 to 10 carbon atoms. In some embodiments, the polyol is a diol having from 10 to 20 carbon atoms. In some embodiments, the polyol is a diol having 7 carbon atoms.

Suitable polyols may include, without limitation, 1,6-hexanediol, 1,8-octanediol, 1,9-nonanediol, 1,10-decanediol, 1,11-undecanediol, 1,12-dodecanediol, 1,13-tridecanediol, 1,14-tetradecanediol, 1,15-pentadecanediol, 1,16-hexadecanediol, 1,17-heptadecanediol, 1,18-octadecanediol, 1,19-nonadecanediol, 1,20-icosanediol, 2-butene-1,4-diol, 3,4-dihydroxy-1-butene, 7-octene-1,2-diol, 3-hexene-1,6-diol, 1,4-butynediol, trimethylolpropane allyl ether, 3-allyloxy-1,2-propanediol, 2,4-hexadiyne-1,6-diol, 2-hydroxymethyl-1,3-propanediol, 1,1,1-Tris(hydroxymethyl)propane, 1,1,1-tris(hydroxymethyl)ethane, pentaerythritol, di(trimethylolpropane) dipentaerythritol and combinations thereof. In the embodiments, the polyol may be 1,8-octanediol and is commercially available from Sigma Aldrich Company LLC (St. Louis, Mo.) or Alfa Aesar (Ward Hill, Mass.).

In some embodiments, the counter-ion protected amino acid-based polyester monomers are formed by first dissolving one or more selected amino acids and selected polyol in a suitable solvent. One of ordinary skill in the art will also be able to select a suitable solvent for the selected amino acid or acids and the selected polyol the without undue experimentation. Suitable solvents include without limitation, toluene, dichloromethane, chloroform, dimethylformamide (DMF) or combinations thereof. In some embodiments, the solvent used may be toluene. Further, as will be apparent to those of skill in the art, steps should be taken to prevent transamidation of the ester bonds on the polyester backbone or catechol side chains. In some embodiments, transamidation may be prevented or limited by protecting the amine groups on the amino acid-based polyester monomers being formed with one or more counter-ions. Accordingly, a suitable acid or other source of counter-ions may be added to the solution prior to or during formation of the polyester monomer. One of ordinary skill in the art will be able to select a suitable counter-ion without undue experimentation. Materials capable of producing suitable protecting counter-ions may include without limitation, p-toluene sulfonic acid monohydrate, chlorides, bromides, acetates. trifloroacetate, or combinations thereof. In some embodiments, the acid used may be p-toluene sulfonic acid monohydrate. In some embodiments, the acid used may be HCl.

In these embodiments, the solution is then heated to a temperature of from 110° C. to about 114° C. and refluxed for from about 20 hours to about 48 hours to form a counter-ion protected amino acid-based polyester monomer having two or more amino acid residues separated by from about 2 to about 60 carbon atoms, depending upon the polyol used. (See Scheme 1, below). In some embodiments, the solution is heated to a temperature of from about 110° C. to about 112° C. In some embodiments, the solution is heated to a temperature of about 110° C. In some of these embodiments, the solution may be refluxed for from about 20 hours to about 40 hours. In some of these embodiments, the solution may be refluxed for from about 20 hours to about 30 hours. In some of these embodiments, the solution may be refluxed for from about 20 hours to about 24 hours.

The crude product of the reactions may be purified using any means known in the art for that purpose, including, without limitation, filtration, crystallization, or column chromatography. One or ordinary skill in the art would know how to purify these products without undue experimentation. In some embodiments, the crude reaction product may be purified by first vacuum filtering to remove the residual solvent and then decolorized in activated carbon to remove any residual salts or unreacted monomers. In some embodiments, the crude reaction product may then be recrystallized from boiling water from 1 to 10 times to produce a purified product. In some embodiments, the crude product may be recrystallized from a 1:1 mixture of water and alcohol from 1 to 10 times to produce a purified product. In some embodiments, after cooling to ambient temperature, the crude product may be filtered, washed with diethyl ether and then recrystallized with water. In some embodiments, the crude product may be filtered, washed with diethyl ether, and collected by vacuum filtration. In some embodiments, the crude product was filtered, concentrated and dissolved in $CHCl_3$, washed with 5% HCl twice, brine once, dried over $Na_2SO_4$ and the solvent removed in vaccuo to produce the purified product.

In some embodiments, the amino acid-based polyester monomers may be synthesized as shown in Scheme 1, below.

Scheme 1

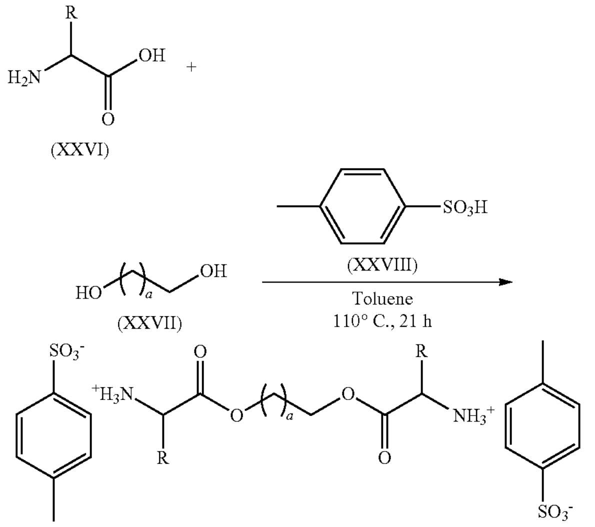

(XXVI)

(XXVII)

(XXVIII)

(XXIX)

wherein R is an amino acid side chain and a is an integer from about 2 to about 20. In some embodiments, R may be any one or more of $—CH_3$, $—(CH_2)_3NHC(NH_2)C{=}NH$, $—CH_2CONH_2$, $—CH_2COOH$, $—CH_2SH$, $—(CH_2)_2COOH$, $—(CH_2)_2CONH_2$, $—NH_2$, $—CH_2C{=}CH—N{=}CH—NH$, $—CH(CH_3)CH_2CH_3$, $—CH_2CH(CH_3)_2$, $—(CH_2)_4NH_2$, $—(CH_2)_2SCH_3$, $—CH_2Ph$, $—CH_2OH$, $—CH(OH)CH_3$, $—CH_2—C{=}CH—NH\text{-}Ph$, $—CH_2\text{-}Ph\text{-}OH$, $—CH(CH_3)_2$. or $—CH_2C_6H_4OCH_2C_6H_5$. In some embodiments, XXVI may be a benzyl protected tyrosine, a tort-butyloxycarbonyl (BOC) protected tyrosine or another functionalized or protected α-amino acid. In some of these embodiments, a may be an integer from about 1 to about 20. In some of these embodiments, a may be an integer from about 1 to about 15. In some of these embodiments, a may be an integer from about 1 to about 12. In some of these embodiments, a may be an integer from about 10 to about 20. In some of these embodiments, a may be an integer from about 4 to about 12. In some of these embodiments, a may be an integer from about 6 to about 12. In some of these embodiments, a may be 8.

In the embodiments shown in Scheme 1 above, one or more amino acids XXVI, a linear diol having from 2 to 20 carbon atoms XXVII, and p-toluene sulfonic acid monohydrate XXVIII are dissolved in toluene, heated to a temperature of about 110° C. and refluxed for about 21 hours to produce the di-p-toluene sulfonic acid salt of an amino acid-based diester monomer XXIX having two or more amino acid residues separated by from about 2 to about 20 carbon atoms, depending upon the polyol XXVII used. (See also, Examples 3-6). In some embodiments, the amino acid XXVI, polyol XXVII and acid may be dissolved in a suitable solvent such as toluene, DMF, and 1,4-paradioxane. One of ordinary skill in the art will be able to select a suitable solvent without undue experimentation.

In some other embodiments, a counter-ion protected amino acid-based polyester monomer according to one or more embodiments of the present invention may be synthesized as shown in Scheme 2, below.

Scheme 2

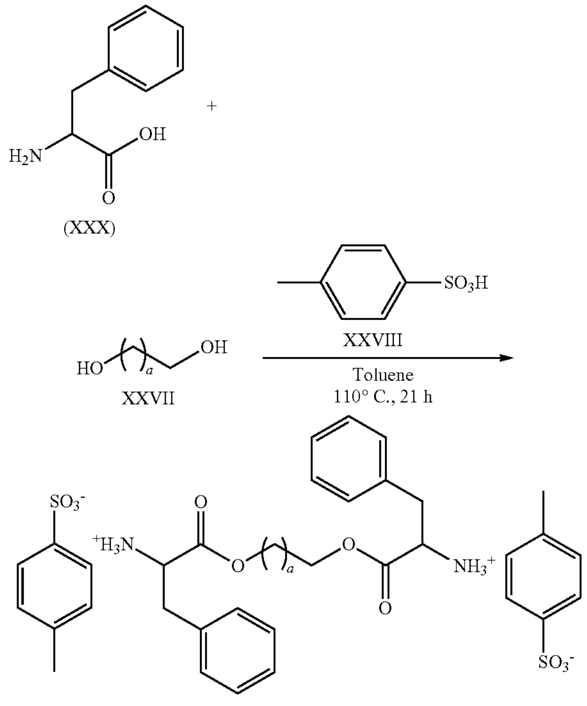

(XXX)

XXVII

XXXI wherein a is an integer from about 1 to about 20. In some of these embodiments, a may be an integer from about 1 to about 15. In some of these embodiments, a may be an integer from about 1 to about 12. In some of these embodiments, a may be an integer from about 10 to about 20. In some of these embodiments, a may be an integer from about 4 to about 12. In some of these embodiments, a may be an integer from about 6 to about 12. In some of these embodiments, a may be 8.

In the embodiments shown in Scheme 2 above, L-phenylalanine XXX, a linear diol having from 2 to 20 carbon atoms XXVII, and p-toluene sulfonic acid monohydrate XXVIII are dissolved in toluene, heated to a temperature of from about 110° C. and refluxed for about 21 hours produce the di-p-toluene sulfonic acid salt of a L-phenylalanine based diester monomer XXXI having two phenylalanine residues separated by from about 2 to about 20 carbon atoms, depending upon the diol XXVII used. (See Scheme 2, above). In some of these embodiments, the solution may be heated to a temperature of from about 110° C. to about 112° C. In some of these embodiments, the solution may be refluxed for from about 20 hours to about 48 hours. In some of these embodiments, the solution may be refluxed for from about 20 hours to about 40 hours. In some of these embodiments, the solution may be refluxed for from about 20 hours to about 30 hours. In some embodiments, the di-p-toluene sulfonic acid salt of an L-phenylalanine based diester monomer XXXI, having two L-phenylalanine residues separated by from about 2 to about 20 carbon atoms, may be synthesized as set forth in Example 4.

In some embodiments, counter-ion protected amino acid-based polyester monomers according to one or more embodiments of the present invention may be synthesized from L-leucine XXXII, a linear diol from 2 to 20 carbon atoms in length XXVII, and p-toluene sulfonic acid monohydrate XXVIII as shown in Scheme 3, below.

Scheme 3

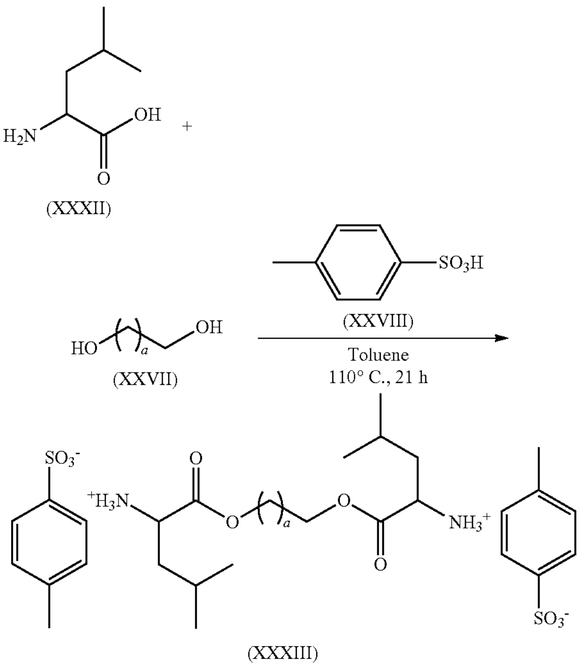

(XXXII)

(XXVII)

(XXXIII)

wherein a is an integer from about 1 to about 20. In some of these embodiments, a may be an integer from about 1 to about 15. In some of these embodiments, a may be an integer from about 1 to about 12. In some of these embodiments, a may be an integer from about 10 to about 20. In some of these embodiments, a may be an integer from about 4 to about 12. In some of these embodiments, a may be an integer from about 6 to about 12. In some of these embodiments, a may be an integer from about 6 to about 10.

In the embodiments shown in Scheme 3 above, L-leucine XXXII, linear diol of from 2 to 20 carbon atoms in length XXVII, and p-toluene sulfonic acid monohydrate XXVIII are dissolved in toluene, heated to a temperature of from about 110° C. and refluxed for about 21 hours produce the di-p-toluene sulfonic acid salt of an L-leucine based diester monomer XXXIII having two L-leucine residues separated by from about 2 to about 20 carbon atoms, depending upon the diol XXVII used. (See Scheme 3, above). One of ordinary skill in the art will be able to select a suitable solvent or solvents without undue experimentation. In some of these embodiments, the solution may be heated to a temperature of from about 110° C. to about 112° C. In some of these embodiments, the solution may be refluxed for from about 20 hours to about 48 hours. In some of these embodiments, the solution may be refluxed for from about 20 hours to about 40 hours. In some of these embodiments, the solution may be refluxed for from about 20 hours to about 30 hours. In some embodiments, the di-p-toluene sulfonic acid salt of an L-leucine based diester monomer XXXIII, having two L-leucine residues separated by from about 2 to about 20 carbon atoms, may be synthesized as set forth in Example 3.

In some other embodiments, another type of counter-ion protected amino acid-based polyester monomers according to the invention having one or more benzyl protected tyrosine residues may be synthesized as shown in Scheme 4, below.

Scheme 4

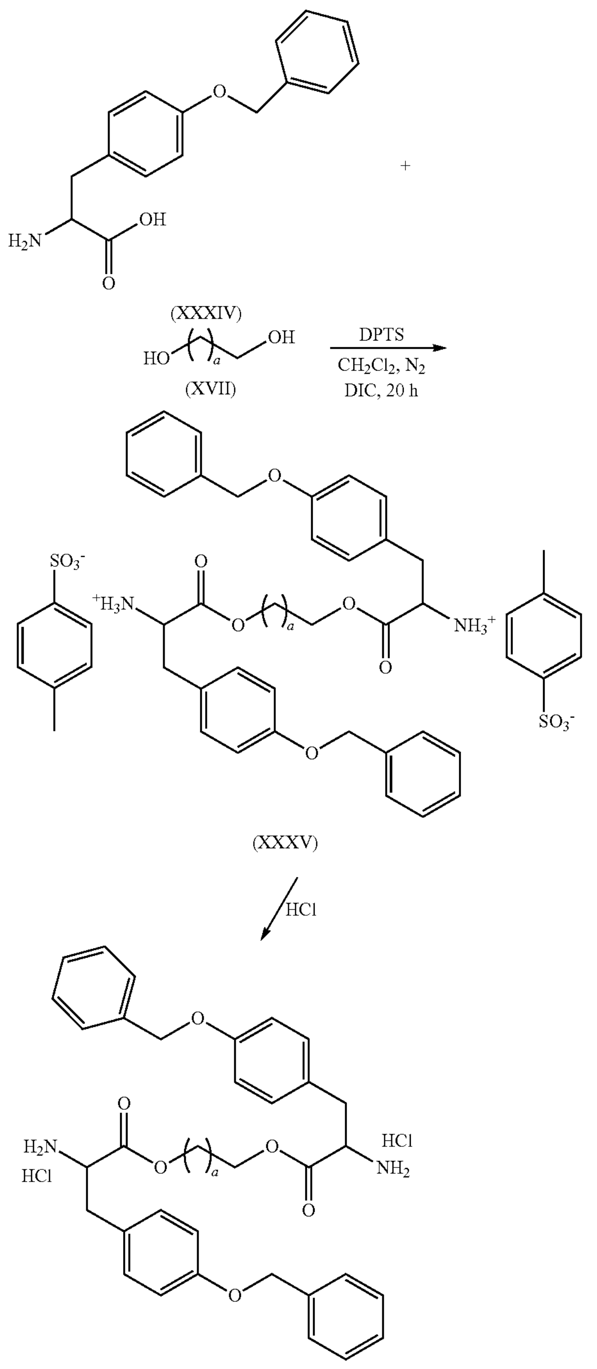

(XXXIV)

(XVII)

(XXXV)

(XXXVI)

wherein a is an integer from about 1 to about 20. In some of these embodiments, a may be an integer from about 1 to about 15. In some of these embodiments, a may be an integer from about 1 to about 12. In some of these embodiments, a may be an integer from about 10 to about 20. In some of these embodiments, a may be an integer from about 4 to about 12. In some of these embodiments, a may be an integer from about 6 to about 12. In some of these embodiments, a may be an integer from about 8 to about 12.

In these embodiments, a benzyl protected tyrosine XXXIV is used as the amino acid for the formation of the counter-ion protected polyester monomer. In these embodiments, the method used to produce the counter-ion protected polyester monomer described above may be modified slightly to produce the di-p-toluene sulfonic acid salt of the benzyl protected tyrosine based diester monomer XXXV, as shown in the first part of Scheme 4, above. In these embodiments, the benzyl protected L-tyrosine XXXIV (N-Boc-O-benzyl-L-tyrosine), a linear diol of from about 2 to about 20 carbon atoms in length XXVII, and a suitable coupling agent such as 4-(dimethylamino)pyridinium 4-toluenesulfonate (DPTS) are first dissolved in a suitable solvent (such as anhydrous dichloromethane) under a nitrogen atmosphere. One of ordinary skill in the art will be able to select a suitable coupling agent without undue experimentation. Suitable coupling agents may include without limitation. Suitable coupling agents may include, without limitation, 2-(1H-benzotriazol-1-yl)-1,1,3,3-tetramethyluronium hexafluorophosphate (HBTU), (benzotriazol-1-yloxy)tris(dimethylamino)phosphonium hexafluorophosphate (BOP), bis-(2-oxo-3-oxazolidinyl)phosphinic chloride (BOP-Cl), (1-cyano-2-ethoxy-2-oxoethylidenaminooxy)dimethylamino-morpholino-carbenium hexafluorophosphate (COMU™), dicyclohexylcarbodiimide (DCC), diisopropylcarbodiimide (DIC), 3-(diethoxyphosphoryloxy)-1,2,3-benzotriazin-4(3H)-one (DEPBT), N-(3-dimethylaminopropyl)-N'-ethylcarbodiimide hydrochloride (EDC), 2-(1H-7-azabenzotriazol-1-yl)-1,1,3,3-tetramethyl uronium hexafluorophosphate (HATU), O-benzotriazole-N,N,N',N'-tetramethyl-uronium-hexafluorophosphate (HBTU), 2-(6-Chloro-1H-benzotriazole-1-yl)-1,1,3,3-tetramethylaminium hexafluorophosphate (HCTU), (7-azabenzotriazol-1-yloxy) tripyrrolidinophosphonium hexafluorophosphate (PyAOP), (benzotriazol-1-yloxy)tripyrrolidinophosphonium hexafluorophosphate (PyBOP), bromotripyrrolidinophosphonium hexafluorophosphate (PyBrOP), O-(7-azabenzotriazole-1-yl)-N,N,N',N'-tetramethyluronium tetrafluoroborate (TATU), O-(benzotriazol-1-yl)-N,N,N',N'-tetramethyluronium tetrafluoroborate (TBTU), N,N,N',N'-tetramethyl-O-(3,4-dihydro-4-oxo-1,2,3-benzotriazin-3-yl)uranium tetrafluoroborate (TDBTU), 2-(5-norborene-2,3-dicarboximido)-1,1,3,3-tetramethyluronium tetrafluoroborate (TNTU), O-[(ethoxycarbonyl)cyanomethylenamino]-N,N,N',N'-tetra methyluronium tetrafluoroborate (TOTU), 2-(2-pyridon-1-yl)-1,1,3,3-tetramethyluronium tetrafluoroborate (TPTU), or N,N,N'N'-tetramethyl-O—(N-succinimidyl)uronium tetrafluoroborate (TSTU).

One of ordinary skill in the art will likewise be able to select a suitable solvent without undue experimentation. Suitable solvents may include without limitation anhydrous dichloromethane, DMF, 1,4-paradioxane. And while the reagents in the reaction shown Scheme 4 are dissolved under a nitrogen atmosphere, it should be understood that any anhydrous gas may have been used including, but not limited to, nitrogen, helium, or argon, without departing from the scope of the present invention.

In these embodiments, the temperature is then reduced to about 0° C. and N,N'-diisopropylcarbodiimide (DIC) added to the solution as a coupling agent. And while the reaction shown in Scheme 4 above used DIC as a coupling agent, it should be understood that any suitable coupling agent may have been used including, but not limited to, DIC, HBTU, BOP, COMU™, DCC, DEPBT, EDC, HATU, HBTU, HCTU, PyAOP, PyBOP, PyBrOP, TATU, TBTU, TDBTU, TNTU, TOTU, TPTU, TSTU, and combinations thereof, without departing from the scope of the present invention. The resulting mixture is stirred for from about 2 hours to about 48 hours to produce the di-p-toluene sulfonic acid salt of a benzyl protected tyrosine based diester monomer XXXV having two benzyl-protected tyrosine residues separated by from about 2 to about 20 carbon atoms (depending upon the polyol used) as shown in the first part of Scheme 4 above.

In the second part of Scheme 4 above, the p-toluene sulfonic acid protecting groups of the di-p-toluene sulfonic acid salt of the benzyl protected tyrosine based diester monomer XXXV are replaced with hydrochloric acid protecting groups to better facilitate quantification of the products for detection analysis. In these embodiments, the p-toluene sulfonic acid protecting groups are replaced with HCl protecting groups by reacting the di-p-toluene sulfonic acid salt of the benzyl protected tyrosine based diester monomer XXXV with HCl to produce the dihydrochloric acid salt of the benzyl protected tyrosine based diester monomer XXXVI.

In some embodiments, the counter-ion protected amino acid-based polyester monomers used to form the amino acid-based PEU adhesives of the present invention may include, without limitation, di-p-toluenesulfonic acid salt of bis-L-leucine-octane-1,8-diester XL (M1), di-p-toluenesulfonic acid salt of bis-L-phenylalanine-octane-1,8-diester XLI (M2), di-hydrochloric acid salt of bis-O-benzl-L-tyrosine-octane-1,8-diester XLII (M3).

In some embodiments, the counter-ion protected amino acid-based polyester monomers used to form the amino acid-based PEU adhesives of the present invention may have one the following formulas:

(XXXVII)

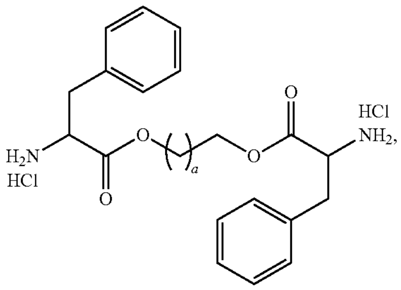

(XXXI)

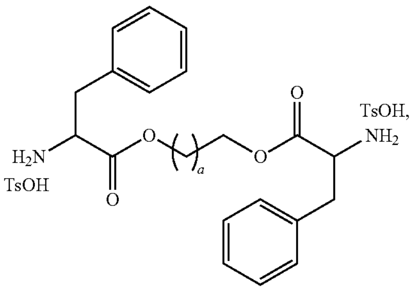

-continued (XXXVIII)

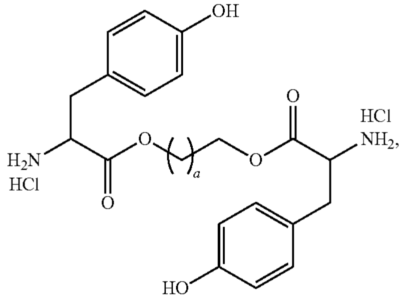

(XXXIX)

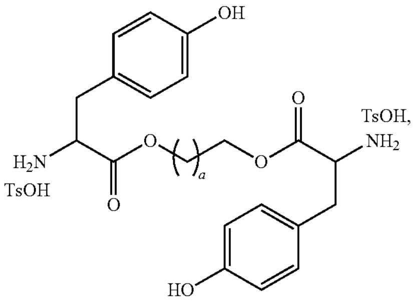

(XXXIII)

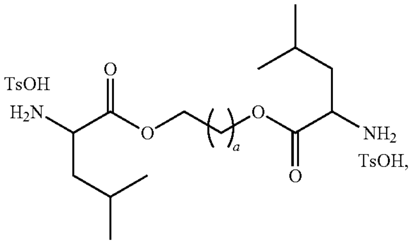

(XL)

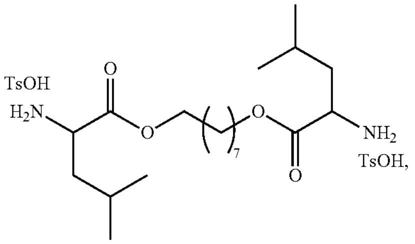

(XLI)

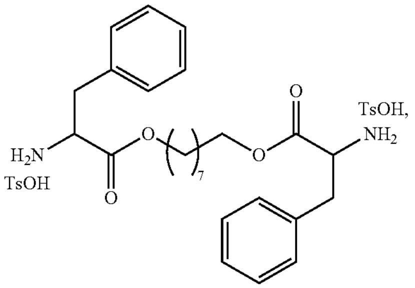

-continued (XLII)

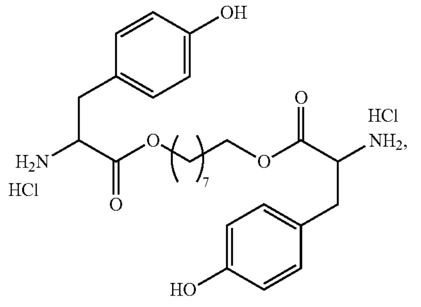

(XXXV)

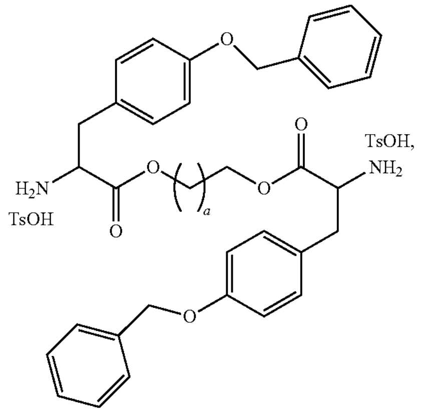

(XXXVI)

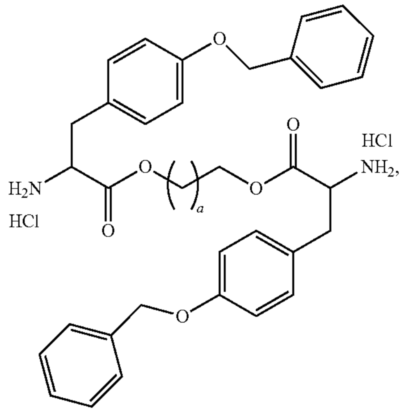

(XLIII)

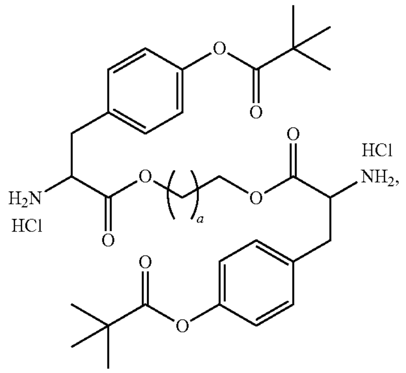

-continued (XLIV)

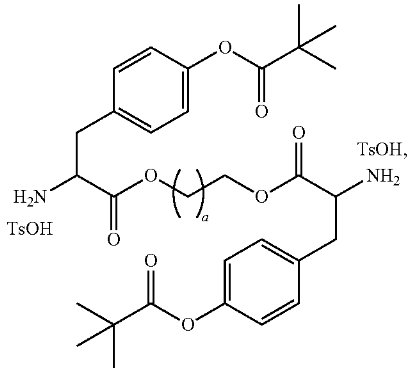

(XX)

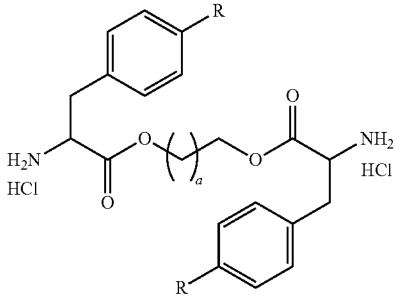

or (XLV)

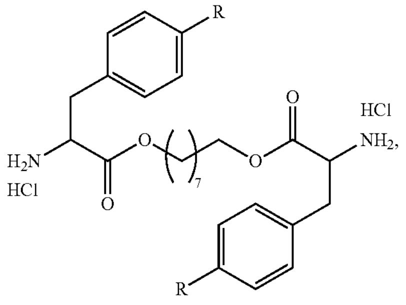

wherein a is an integer from about 1 to about 20 and R is H, OH, or $—OCOO(CH_2)_2C_6H_3(OH)_2$.

In a second step, the counter-ion protected amino-acid-based polyester monomers discussed above are polymerized with a PEU forming material such as phosgene, diphosgene or triphosgene using an interfacial polymerization methods to form amino acid-based PEU adhesives according to one or more embodiments of the present invention. As used herein, the term “interfacial polymerization” refers to polymerization that takes place at or near the interfacial boundary of two immiscible fluids. In some embodiments, the interfacial polymerization reaction is a polycondensation reaction.

In these embodiments, the counter-ion protected amino acid-based polyester monomers discussed above are combined in a desired molar ratio with a first fraction of a suitable organic water soluble base such as sodium carbonate, potasium carbonate, sodium bicarbonate, or potassium bicarbonate and dissolved in water. One of ordinary skill in the art will be able to dissolve the counter-ion protected amino acid-based polyester monomers and organic water soluble base in water without undue experimentation. In some embodiments, the counter-ion protected amino acid-based polyester monomers and organic water soluble base may be dissolved in water using mechanical stirring and a warm water bath (approximately 35° C.).

To introduce the urea bond to the amino acid functionalized monomer or monomers, a PEU forming material is employed. As used herein, the terms "PEU forming compound" and "PEU forming material" are used interchangeably to refer to a material capable of placing a carboxyl group between two amine groups, thereby forming a urea bond. Suitable PEU forming material may include, without limitation, triphosgene, diphosgene, or phosgene. It should be noted that, diphosgene (a liquid) and triphosgene (a solid crystal) are understood to be more suitable than phosgene, as they are generally known as safer substitutes for phosgene, which is a toxic gas. The reaction of the counter-ion protected amino acid-based polyester monomer or monomers with triphosgene, diphosgene or phosgene to create an amino acid-based PEU may be achieved as described below or in any number of ways generally known to those of skill in the art.

In some embodiments, amino acid-based PEU adhesives of the present invention may be synthesized by homopolymerization of a single type of counter-ion protected amino acid-based polyester monomer as shown in Scheme 5 below:

Scheme 5

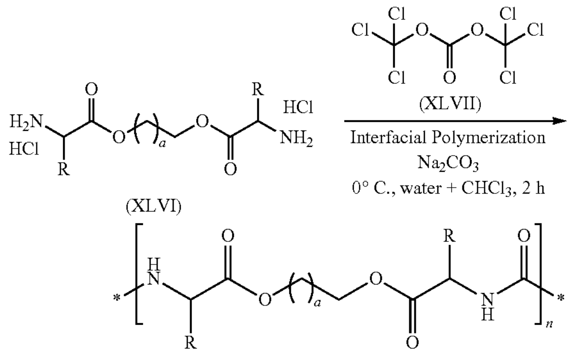

(XLVI)

(XLVIII)

wherein R is $—CH_3$, $—(CH_2)_3NHC(NH_2)C{=}NH$, $—CH_2CONH_2$, $—CH_2COOH$, $—CH_2SH$, $—(CH_2)_2COOH$, $—(CH_2)_2CONH_2$, $—CH_2C{=}CH—N{=}CH—NH$, $—CH(CH_3)CH_2CH_3$, $—CH_2CH(CH_3)_2$, $—(CH_2)_2SCH_3$, $—CH_2Ph$, $—CH_2OH$, $—CH(OH)CH_3$, $—CH_2—C{=}CH—NH\text{-}Ph$, $—CH_2\text{-}Ph\text{-}OH$, $—CH(CH_3)_2$, $—CH_2C_6H_4OCH_2C_6H_5$, $—CH_2C_6H_4OCOOCH_2(CH_3)_3$, or a combination thereof; a is an integer from about 1 to about 20; and n is an integer from about 20 to about 200. In these embodiments, the mechanical, adhesive, thermal, degradation, and solubility based methods of delivery properties of the homopolymer may be regulated by controlling the type and ratio of amino acids and polyols used to form the counter-ion protected amino acid-based polyester monomer used.

In these embodiments, the counter-ion protected amino acid-based polyester monomer XLVI is combined with a first fraction of a suitable base such as sodium carbonate, potasium carbonate, sodium bicarbonate, or potassium bicarbonate, and dissolved in water using mechanical stirring and a warm water bath (approximately 35° C.). Again, one of ordinary skill in the art will be able to dissolve the counter-ion protected amino acid-based polyester monomers and organic water soluble base in water without undue experimentation. The reaction is then cooled to a temperature of from about −10° C. to about 2° C. and an additional fraction of base is dissolved in water and added to the reaction mixture.

Next, a first fraction of a PEU forming compound XLVII is dissolved in a suitable solvent and added to the reaction mixture. One of ordinary skill will be able to select a suitable solvent for the PEU forming compound XLVII without undue experimentation. Selection of a suitable solvent for the PEU forming compound XLVII will, of course, depend upon the particular compound chosen, but may include, without limitation, distilled chloroform, dichloromethane, or dioxane. In the embodiment shown in Scheme 5 above, the PEU forming compound XLVII is provided in the form of triphosgene and the solvent is chloroform. After a period of from about 2 to about 60 minutes, a second fraction of the PEU forming material (such as triphosgene or phosgene) is dissolved in a suitable solvent, such as distilled chloroform or dichloromethane, and added dropwise to the reaction mixture over a period of from about 0.5 to about 12 hours to produce a crude homopolymer. The crude product may be purified using any means known in the art for that purpose. In some embodiments, the crude homopolymer product may be purified by transferring it into a separatory funnel and precipitating it into boiling water.

In some other embodiments, the amino acid-based PEU adhesives of the present invention may be synthesized by copolymerizing two or more different types of counter-ion protected polyester monomers, with each type of counter-ion protected monomers having a different and distinct combination of amino acid residues. In many (but not all) of these embodiments, each type of counter-ion protected amino acid-based polyester monomer used will comprise a single type of amino acid residue and a single type polyol residue so that the counter-ion protected polyester monomer will have uniform properties. Moreover, as should be apparent to those of skill in the art, using monomers with known and uniform properties permits the tuning of the amino acid-based PEU adhesives of the present invention to obtain desired adhesive and/or other properties. In some embodiments, this may be accomplished by selection of counter-ion protected polyester monomer types that have the desired properties and then controlling the feed rate of the selected monomers and during polymerization. In this way, it is possible to synthesize amino acid-based PEU adhesives having adhesive, mechanical, elastic modulus, thermal, degradation, and solubility based methods of delivery, desirable for specific applications.

Once the two or more selected counter-ion protected amino acid-based polyester monomers have been prepared, they may be copolymerized with a PEU forming material as set forth above for homopolymers and/or in Scheme 6 below to form an amino acid-based PEU adhesive XLIX having first segments comprising the residue of a first counter-ion protected amino acid-based polyester monomer XLVI and second segments comprising the residue of a second counter-ion protected amino acid-based polyester monomer XXIX.

Scheme 6

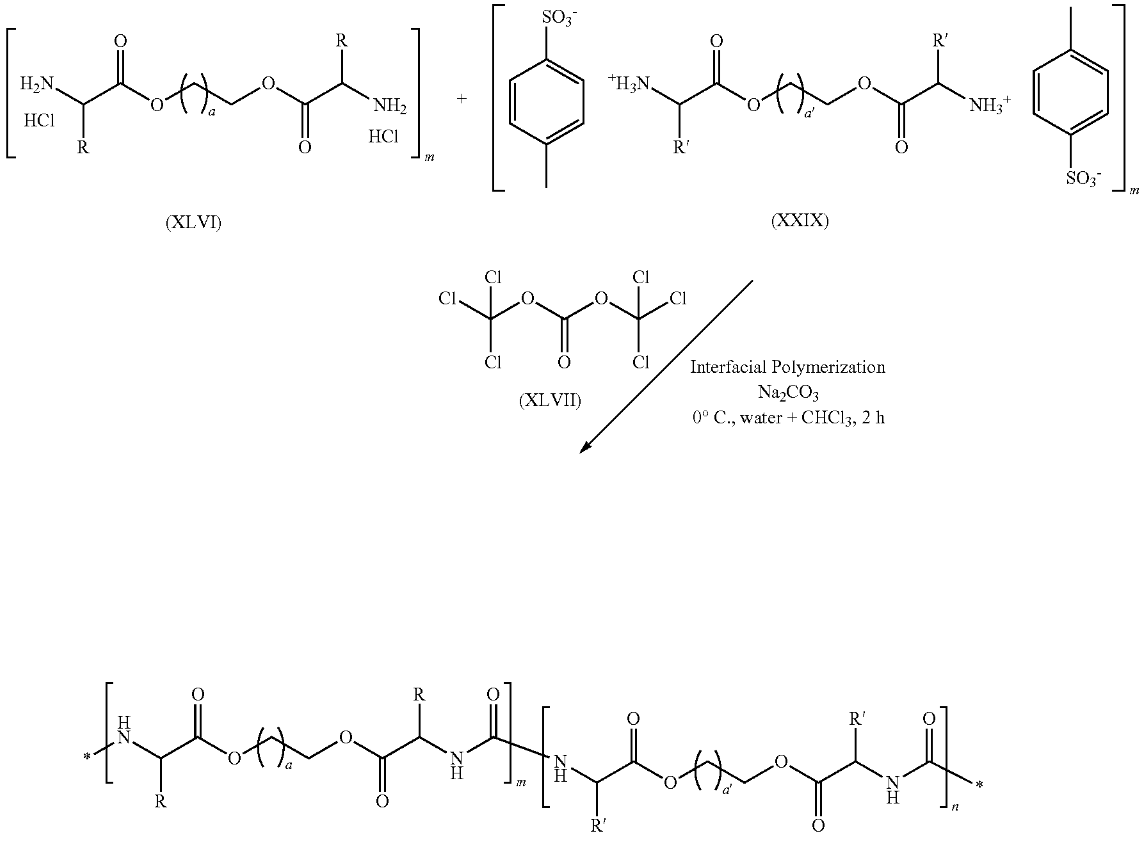

(XLVI) (XXIX) (XLVII) (XLIX)

In the embodiments shown in Scheme 6, R and R' are $—CH_3$, $—(CH_2)_3NHC(NH_2)C{=}NH$, $—CH_2CONH_2$, $CH_2COOH$, $—CH_2SH$, $—(CH_2)_2COOH$, $—(CH_2)_2CONH_2$, $—NH_2$, $—CH_2C{=}CH—N{=}CH—NH$, $—CH(CH_3)CH_2CH_3$, $—CH_2CH(CH_3)_2$, $—(CH_2)_4NH_2$, $—(CH_2)_2SCH_3$, $—CH_2Ph$, $—CH_2OH$, $—CH(OH)CH_3$, $—CH_2—C{=}CH—NH\text{-}Ph$, $—CH_2Ph\text{-}OH$, $—CH(CH_3)_2—CH_2C_6H_4OCH_2C_6H_5$, or $—CH_2C_6H_4OCOOCH_2(CH_3)_3$; a and a' are each an integer from about 1 to about 20; m is a mole fraction from about 0.01 to about 0.30 and n is a mole fraction from about 70 to about 0.99.

In some of these embodiments, a is an integer from 1 to 15. In some of these embodiments, a is an integer from 1 to 12. In some of these embodiments, a is an integer from 10 to 20. In some of these embodiments, a is an integer from 4 to 12. In some of these embodiments, a' is an integer from 6 to 12. In some of these embodiments, a' is an integer from 8 to 12. In some of these embodiments, a' is an integer from 1 to 15. In some of these embodiments, a' is an integer from 1 to 12. In some of these embodiments, a' is an integer from 10 to 20. In some of these embodiments, a' is an integer from 4 to 12. In some of these embodiments, a' is an integer from 6 to 12. In some of these embodiments, m is a mole fraction of from about 0.05 to about 0.30. In some of these embodiments, m is a mole fraction of from about 0.01 to about 0.20. In some of these embodiments, m is a mole fraction of from about 0.01 to about 0.15. In some of these embodiments, m is a mole fraction of from about 0.01 to about 0.10. In some of these embodiments, m is a mole fraction of from about 0.05 to about 0.30. In some of these embodiments, m is a mole fraction of from about 0.10 to about 0.30. In some of these embodiments, m is a mole fraction of from about 0.15 to about 0.30. In some of these embodiments, m is a mole fraction of from about 0.20 to about 0.30. In some of these embodiments, n is a mole fraction of from about 0.75 to about 0.99. In some of these embodiments, n is a mole fraction of from about 0.80 to about 0.99. In some of these embodiments, n is a mole fraction of from about 0.85 to about 0.99. In some of these embodiments, n is a mole fraction of from about 0.90 to about 0.99. In some of these embodiments, n is a mole fraction of from about 0.70 to about 0.95. In some of these embodiments, n is a mole fraction of from about 0.70 to about 0.85. In some of these embodiments, n is a mole fraction of from about 0.70 to about 0.75. In some of these embodiments, n is a mole fraction of from about 0.90 to about 0.95.

In some embodiments, such as the embodiments shown in Scheme 7, below, the amino acid-based PEU adhesive of the present invention may be a copolymer a first counter-ion protected amino acid-based polyester monomer XX having amino acid residues or functionalized amino acid residues with good adhesion properties and a counter-ion protected amino acid-based polyester monomer XXIX having other amino acids and other useful mechanical, thermal, degradation, and solubility properties, as described above. See Scheme 7, below.

Scheme 7

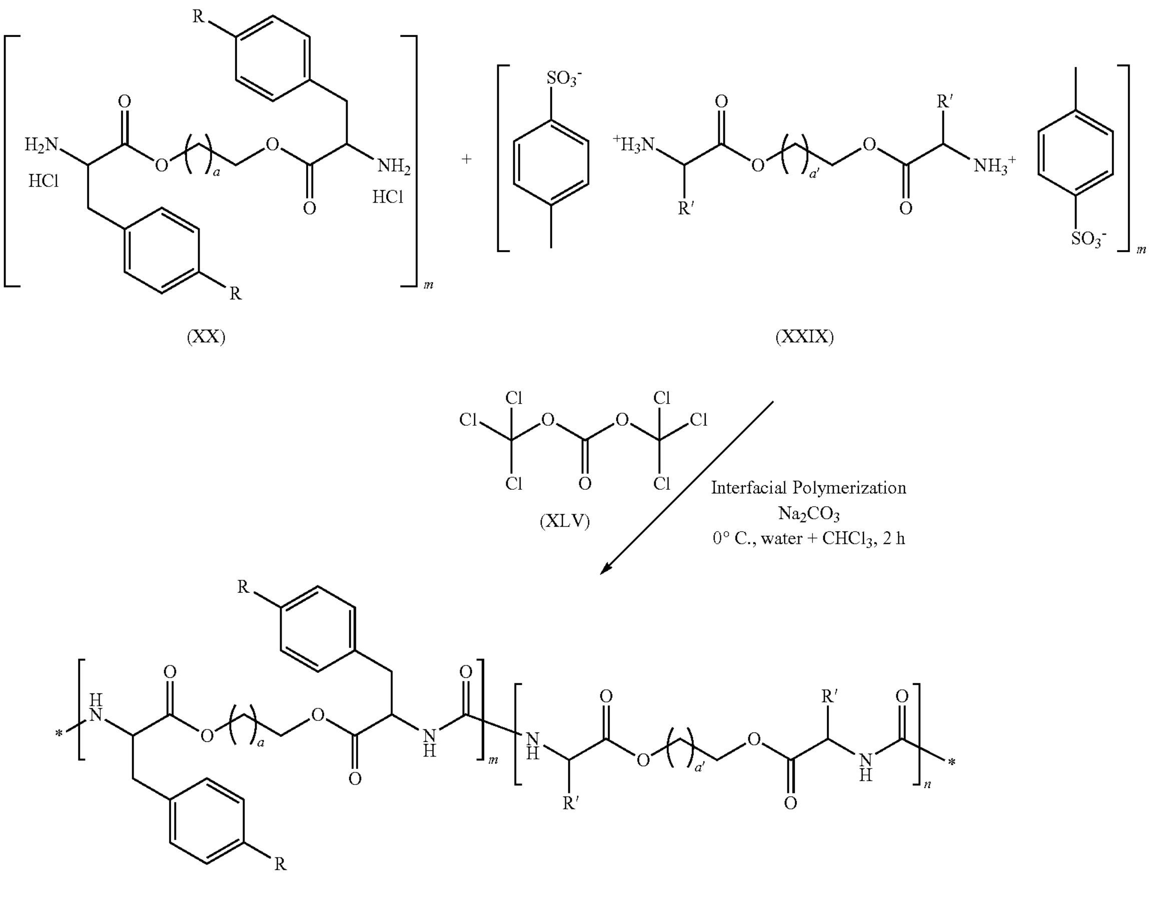

(XX) (XXIX) (XLV)

(III)

In the embodiments shown in Scheme 7, R may be H, OH, $—OCH_2C_6H_5$, or $—OCOOCH(CH_3)_3$ and R' may be $—CH_3$, $—(CH_2)_3NHC(NH_2)C{=}NH$, $—CH_2CONH_2$, $—CH_2COOH$, $—CH_2SH$, $—(CH_2)_2COOH$, $—(CH_2)_2CONH_2$, $—CH_2C{=}CH—N{=}CH—NH$, $—CH(CH_3)CH_2CH_3$, $—CH_2CH(CH_3)_2$, $—(CH)_2SCH_3$, $—CH_2Ph$, $—CH_2OH$, $—CH(OH)CH_3$, $—CH_2—C{=}CH—NH\text{-}Ph$, $—CH_2\text{-}Ph\text{-}OH$, or $—CH(CH_3)_2$. In these embodiments, a, a', m and n may all be as set forth above with respect to Scheme 6.

In addition, while Scheme 7 shows HCl and p-toluene sulfonic acid counter-ions, it should be appreciated that any suitable counter ion may be used. Materials capable of producing suitable protecting counter-ions may include without limitation, p-toluene sulfonic acid monohydrate, chlorides, bromides, acetates. trifloroacetate, or combinations thereof. One of ordinary skill in the art will be able to select a suitable counter-ion without undue experimentation.

In some embodiments in which the first segment of the amino acid-based PEU adhesive of the present invention is to be tyrosine or a catechol functionalized tyrosine, the first monomer XX in Scheme 7 above may comprise one or preferably two tyrosine or benzyl protected tyrosine residues. While in some embodiments, the amino acid-based PEU adhesive of the present invention may be made from tyrosine-based polyester monomers (see e.g., molecules V and VIII, above), it has been found that use of unprotected tyrosine-based polyester monomers can lead to unwanted cross reactions and the formation of unwanted branch structures. Accordingly, it is advantageous to protect the tyrosine phenol groups prior to polymerization for embodiments of the present invention where the functional group on the first segment of the amino acid-based PEU adhesives of the present invention is to be tyrosine or catechol functionalized tyrosine. In some embodiments, tyrosine-based polyester monomers according to the present invention may be made from BOC or benzyl protected tyrosine-based polyester monomers.

In some embodiments, amino acid-based PEU adhesives having tyrosine functional groups (Tyr-PEU) may be prepared by post-polymerization modification of PEU polymers having protected tyrosine residues. (See e.g. molecule VIII) In some embodiments, Tyr-PEU may be formed by a palladium catalyzed hydrogenation reaction to deprotect benzyl protecting groups to provide the phenyol group of the tyrosine functional group. Catechol functionalized PEUs (CA-PEU) may then be achieved through post-polymerization functionalization.

In one or more of these embodiments, an amino-acid-based PEU is formed as shown in Scheme 7 above, wherein the first monomer XX has two benzyl protected tyrosine residues ($R{=}OCH_2C_6H_5$). The resulting PEU will, therefore, comprise one or more first segments having two benzyl protected tyrosine residues ($R{=}OCH_2C_6H_5$) and one or more second segments having two other amino acid residues.

In these embodiments, the benzyl protected tyrosine residues on these PEUs are first deprotected to produce a PEU with two tyrosine residues and having the formula:

(VIII)

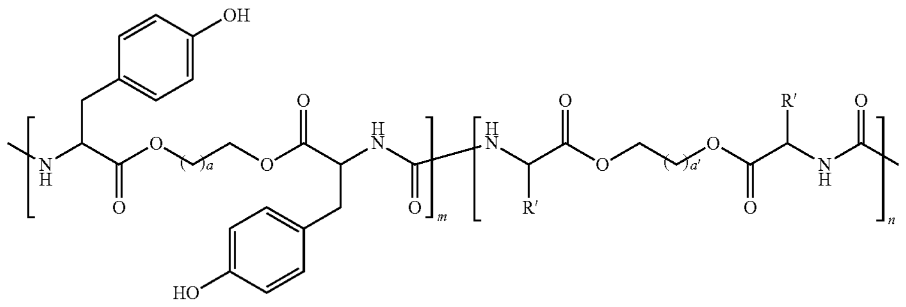

wherein R' is $-CH_3$, $-(CH_2)_3NHC(NH_2)C{=}NH$, $-CH_2CONH_2$, $-CH_2COOH$, $-CH_2SH$, $-(CH_2)_2COOH$, $-(CH_2)_2CONH_2$, $-NH_2$, $-CH_2C{=}CH{-}N{=}CH{-}NH$, $-CH(CH_3)CH_2CH_3$, $-CH_2CH(CH_3)_2$, $-(CH_2)_4NH_2$, $-(CH_2)_2SCH_3$, $-CH_2Ph$, $-CH_2OH$, $-CH(OH)CH_3$, $-CH_2{-}C{=}CH{-}NH{-}Ph$, $-CH_2{-}Ph{-}OH$, or $-CH(CH_3)_2$. In these embodiments, a, a', m and n may all be as set forth above with respect to Scheme 6, above.

The benzyl protected tyrosine residues may be deprotected by any suitable means known in the art for that purpose. In some embodiments, the benzyl protected tyrosine residues may be deprotected by reaction with a reducing agent, such as a hydrogen in the presence of palladium on carbon catalyst. Likewise, BOC protected tyrosine residues may be deprotected by any suitable means known in the art for that purpose. In some embodiments, the BOC protected tyrosine residues may be deprotected by reacting them with an acid group such as TFA in dichloromethane.

In some embodiments of the present invention, the tyrosine residues of the resulting deprotected PEUs VIII above may be functionalized with a catechol group. As will be apparent to those of skill in the art, these catechol groups must be functionalized to bond with the phenol groups on the tyrosine residues of the PEU and protected to prevent unwanted cross linking and/or formation of unwanted branched structures. In some embodiments, the catechol compounds may comprise a carboxyl functionalized catechol group. In some of these embodiments, the carboxyl functional group may be separated from the catechol group by from 1 to 6 carbon atoms. In some of these embodiments, the carboxyl functional group may be separated from the catechol group by from 2 to 5 carbon atoms. In some of these embodiments, the carboxyl functional group may be separated from the catechol group by from 2 to 4 carbon atoms. In some embodiments, the catechol compound may be the deaminated form of the naturally occurring 3,4-dihydroxyphenylalanine (DOPA). In some embodiments, the catechol compound may be 3,4-dihydroxyhydrocinnamic acid and is commercially available from Sigma Aldrich Company LLC (St. Louis, Mo.) or Alfa Aesar (Ward. Hill, Mass.).

The catechol groups of the protected catechol compounds may be protected in any manner known in the art for that purpose provided that provided that removal of the protecting group does not cause degradation of the parent compound. In some embodiments, acetonide protection mechanisms known in the art may be utilized to protect the catechol groups. In some embodiments, the catechol groups may be added to tyrosine residues on PEU adhesives of the present invention via one or more carboxyl functionalized acetonide protected catechol compounds. In some embodiments, these carboxyl functionalized acetonide protected catechol compounds may have the formula:

(L)

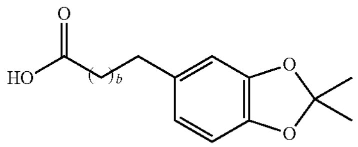

wherein b is an integer from about 0 to about 6. In some embodiments b may be an integer from about 2 to 6. In some embodiments b may be an integer from about 3 to 6. In some embodiments b may be an integer from about 2 to 5. In some embodiments b may be an integer from about 2 to 4. In some embodiments b may be 1. In some embodiments, the carboxyl functionalized protected catechol compound comprises 2,2-dimethyl-1,3-benzodioxole-5-propanoic acid, 2,2-dimethyl-1,3-benzodioxole-5-butanoic acid, 2,2-dimethyl-1,3-benzodioxole-5-petnanoic acid, 2,2-dimethyl-1,3-benzodioxole-5-hexanoic acid, 2,2-dimethyl-1,3-benzodioxole-5-heptanoic acid, or 2,2-dimethyl-1,3-benzodioxole-5-octanoic acid.

In some embodiments, the carboxyl functionalized protected catechol compounds may be prepared from the corresponding carboxyl functionalized catechol by reaction with acetone under basic conditions. In some embodiments, the carboxyl functionalized protected catechol compounds may be prepared as described in Example 1, below.

Accordingly, in these embodiments, the PEU VIII is first reacted with a carboxyl functionalized protected catechol compound, thereby adding a protected catechol group to the tyrosine residues of the first segments of the PEU by means of a condensation reaction between the carboxyl group on the carboxyl functionalized protected catechol and the phenol group on the tyrosine residue of the first segments of the PEU to form a protected catechol functionalized PEU intermediate XXII. In some embodiments, amino acid-based PEU intermediates with protected catechol groups (CA (AN)-PEU) were synthesized through an esterification reaction between an acetonide protected 3,4-dihydroxyhydrocinnamic acid XXI and the phenol groups on the tyrosine residues.

In some embodiments, the protected catechol functionalized PEU intermediate may have the formula:

(XXII)

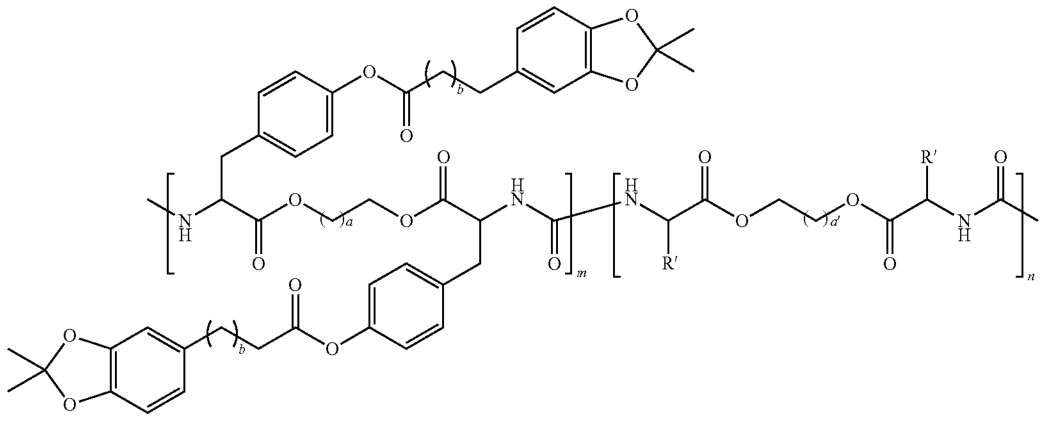

wherein R' is $-CH_3$, $-(CH_2)_3NHC(NH_2)C{=}NH$, $-CH_2CONH_2$, $-CH_2COOH$, $-CH_2SH$, $-(CH_2)_2COOH$, $-(CH_2)_2CONH_2$, $-NH_2$, $-CH_2C{=}CH-N{=}CH-NH$, $-CH(CH_3)CH_2CH_3$, $-CH_2CH(CH_3)_2$, $-(CH_2)_4NH_2$, $-(CH_2)_2SCH_3$, $-CH_2Ph$, $-CH_2OH$, $-CH(OH)CH_3$, $-CH_2-C{=}CH-NH-Ph$, $-CH_2$-Ph-OH, or $-CH(CH_3)_2$ and b is an integer from about 0 to about 6. In these embodiments, a, a', m and n may all be as set forth above with respect to Scheme 6, above.

Finally, protected catechol functionalized PEU intermediate may be deprotected by any suitable means known in the art for that purpose to produce an amino acid-based PEU adhesive according to one or more embodiments of the present invention. The method selected for deprotecting the protected catechol functionalized PEU intermediate will, of course, depend upon the way in which the catechol group has been protected. In some embodiments, an acetonide protected catechol compound is used to form the protected catechol functionalized PEU intermediate. In these embodiments, the acetonide protected catechol groups may be deprotected by reaction with a strong acid such as triflouroacetic acid (TFA) and a proton scavenger such as triisopropylsilyl (TIPS) to obtain free catechol groups. Again, these methods are well known in the art and one of ordinary skill in the art will be able to select a suitable acid without undue experimentation. In the embodiment shown in Scheme 8, for example, the acid is TFA. One of ordinary skill in the art will likewise be able to select a suitable proton scavenger without undue experimentation. In the embodiment shown in Scheme 8, for example, the proton scavenger is TIPS. In some embodiments, the acetonide protected catechol groups may be deprotected as decribed in Example 7.

In some embodiments, the resulting degradable amino acid-based PEU adhesive may have the formula:

(VII)

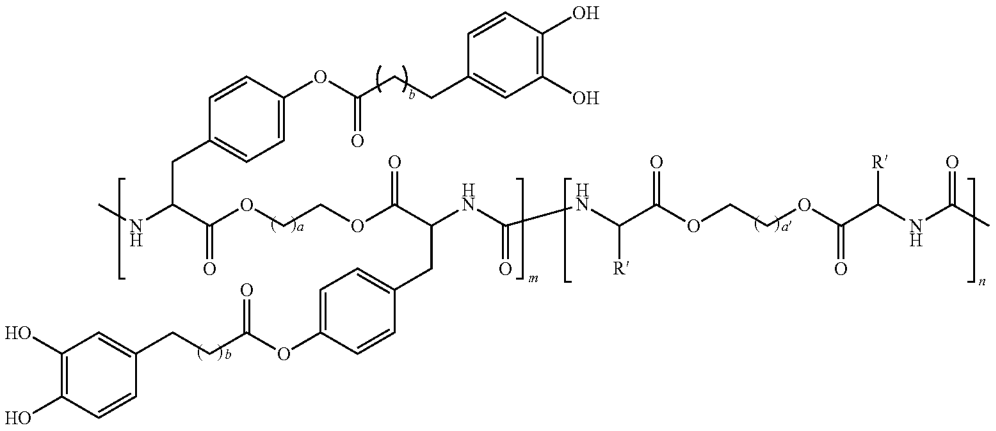

wherein R' is $-CH_3$, $-(CH_2)_3NHC(NH_2)C{=}NH$, $-CH_2CONH_2$, $-CH_2COOH$, $-CH_2SH$, $-(CH_2)_2COOH$, $-(CH_2)_2CONH_2$, $-NH_2$, $-CH_2C{=}CH-N{=}CH-NH$, $-CH(CH_3)CH_2CH_3$, $-CH_2CH(CH_3)_2$, $-(CH_2)_4NH_2$, $-(CH_2)_2SCH_3$, $-CH_2Ph$, $-CH_2OH$, $-CH(OH)CH_3$, $-CH_2-C{=}CH-NH-Ph$, $-CH_2$-Ph-OH, or $-CH(CH_3)_2$ and b is an integer from about 0 to 6. In these embodiments, a, a', m and n may all be as set forth above with respect to Scheme 6.

Experimental

In order to better evaluate the properties of the amino acid-based PEU adhesives of the present invention, a series of eight amino acid-based PEU adhesives having different functional groups present in different molar ratios were prepared. All of these amino acid-based PEU adhesives were copolymers having 1,8-octane-L-leucine based second segments and first segments having different functional units, namely, L-phenylalanine, L-tyrosine, acetonide protected catechol functionalized L-tyrosine and catechol functionalized L-tyrosine present in a mole fraction of 0.05 or 0.10 of the PEUs tested. Physical properties and lap-shear adhesion strength were characterized and compared between these copolymers with different contents of functional units. Surface energies of these PEUs and Johnson-Kendall-Roberts (JKR) work of adhesion were also investigated. Preliminary tissue adhesion properties were evaluated by using porcine skins as adherends.

Polymer Synthesis and Characterization. Scheme 8 below shows the synthetic route of the PEU-based adhesive polymers used for the following experiments. Phenylalanine, leucine and benzyl protected tyrosine containing PEUs were prepared via interfacial polycondensation between respective monomers and triphosgene, as set forth above. It has been found that fast reaction rates and nearly quantitative yields can be achieved through interfacial polymerization under low temperature. Further, since interfacial polymerization is kinetically controlled, precise stoichiometric control between monomers and triphosgene is less critical. Two different monomer feed ratios (5:95 and 10:90) were used to obtain PEUs with different contents of phenylalanine and benzyl protected tyrosine units. The $^1$H NMR of the obtained polymers showed that ratios of monomers incorporated into the PEUs were close to the feed ratios. For these experiments, all PEUs were named to indicate the functional unit and its feeding amount. All other units were leucine-based as indicated in Scheme 8. For example, 10% Phe is a PEU with 10% of phenylalanine based units, while 10% CA means the PEU has 10% of catechol functional units. See molecules X (5% Phe), XI (5% Tyr), XXI (5% CA(AN)), XII (5% CA), XIII (10% Phe), XIV (10% Tyr), XXII (10% CA(AN)), and XV (10% CA), above.

Scheme 8
The Synthesis Route of PEU-Based Adhesives
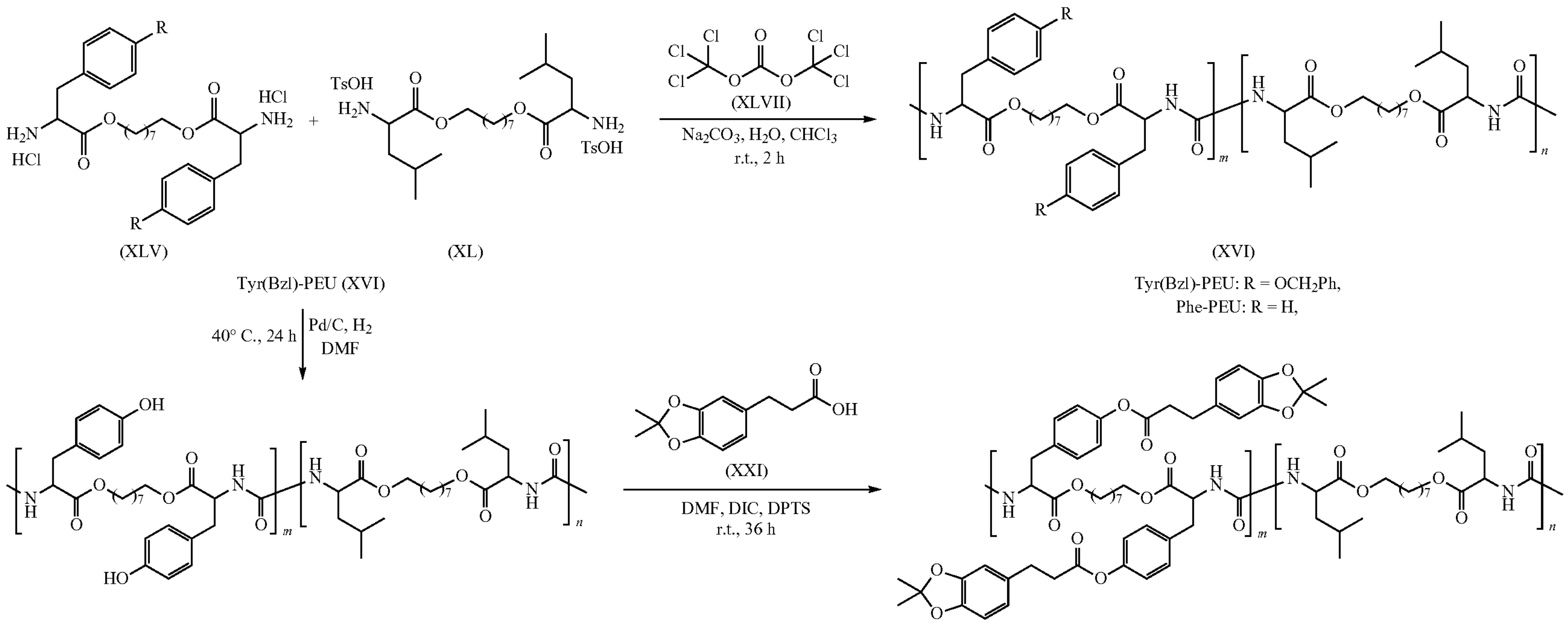
(XLV) (XL)
(XVI)
Tyr(Bzl)-PEU: R = $OCH_2Ph$,
Phe-PEU: R = H,
(XVII)
Tyr-PEU
(XXII)
CA(AN)-PEU -continued
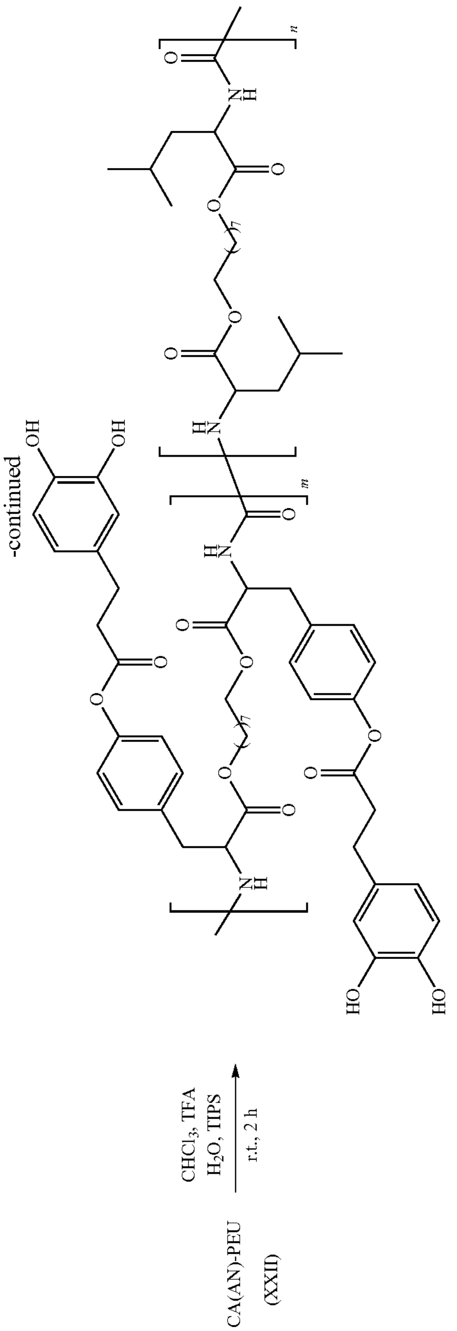
(XVIII)
CA-PEU
m = 0.05, n = 0.95 or
m = 0.1, n = 0.9

Tyrosine functional units containing PEUs (Tyr-PEU) were prepared by a palladium catalyzed hydrogenation reaction to replace the benzyl protecting groups with hydrogen atoms. Catechol functionalized PEUs (CA-PEU) were achieved through post-polymerization functionalization as described above. First, PEUs with protected catechol groups (CA(AN)-PEU) were synthesized and added to the Tyr-PEU through esterification reaction between acetonide protected 3,4-dihydroxyhydrocinnamic acid and phenol groups of the Tyr-PEU. After deprotection with trifluoroacetic acid, free catechol groups were obtained.

Figure 1:
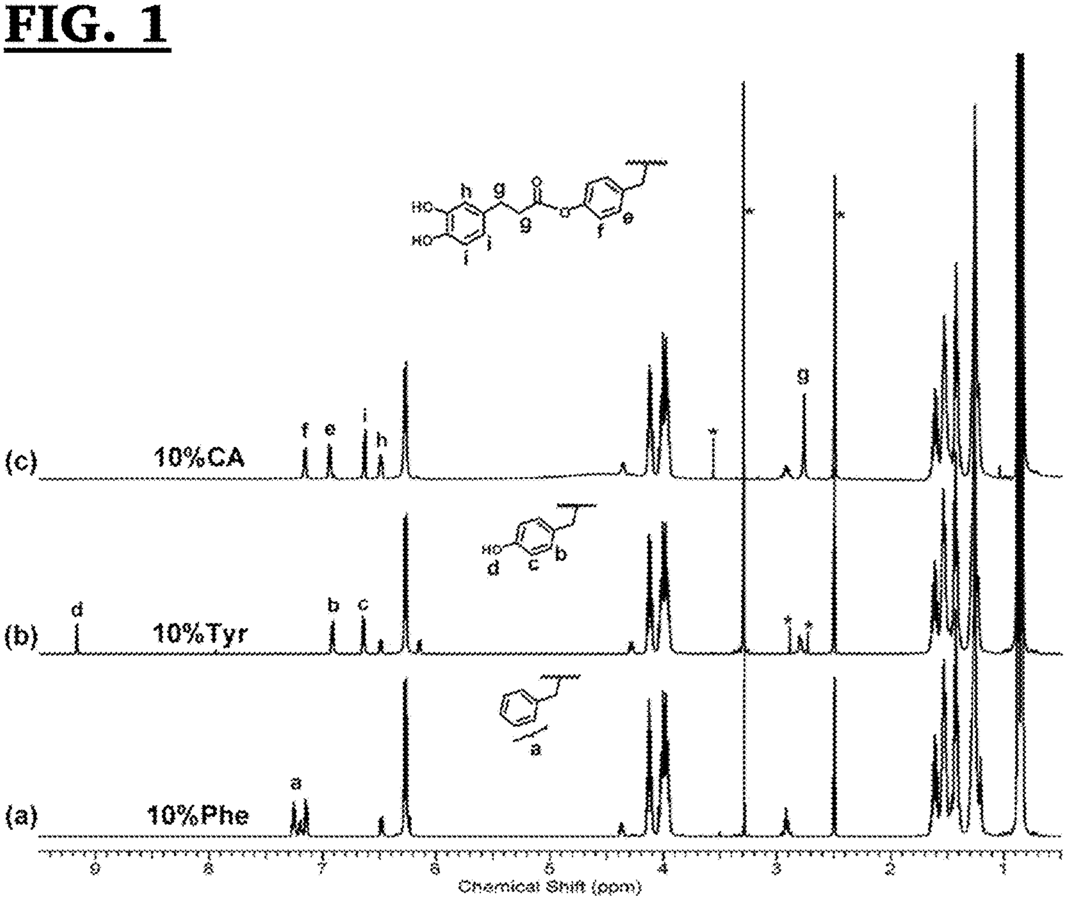
FIG. 1 is a schematic comparing the $^1$H NMR spectra of a PEU polymer having 10% phenylalanine groups (10% Phe) (line (a)), a PEU polymer having 10% tyrosine groups (10% Tyr) (line (b)), and a PEU polymer according to one or more embodiments of the present invention having 10% catechol groups (10% CA) (line (c)). The peaks corresponding to functional units are assigned.

The PEUs with different functional groups were characterized by $^1$H NMR spectroscopy. FIG. 1 shows the $^1$H NMR spectra of 10% Phe, 10% Tyr and 10% CA with assignments. Aromatic protons of 10% Phe have chemical shifts between 7.14 ppm and 7.29 ppm (FIG. 1, line (a)). FIG. 1, line (b) shows characteristic peaks from tyrosine units: peaks located at 6.64 ppm and 6.92 ppm are from tyrosine aromatic protons, while the single peak at 9.17 ppm is assigned to hydroxyl protons. The hydrogenation reaction removed benzyl protecting groups completely, which was confirmed by comparing $^1$H NMR spectra before and after the reaction. Peaks corresponding to benzyl aromatic and methylene protons disappeared after hydrogenation (FIG. 2). FIG. 1, line (c) indicates all the phenol groups were reacted to form ester bonds since no peak at 9.17 ppm is observed. The single peak located at 2.77 ppm comes from methylenes of 3,4-dihydroxyhydrocinnamic acid. The aromatic protons from catechol group have chemical shifts of 6.47-6.53 ppm and 6.62-6.66 ppm; peaks at 6.94 ppm and 7.16 ppm are from tyrosine units. The deprotection reaction was successful confirmed by $^1$H NMR (FIG. 1 and $^{13}$C NMR (FIG. 3). PEUs with 5% functional groups were synthesized and also characterized by NMR spectroscopy.

TABLE 3

Surface Tension of Liquids Used for the Contact Angle Measurement.

| | Ethylene Glycol | Formamide | Glycerol | $H_2O$ | Propylene Glycol |
|---|---|---|---|---|---|
| $\gamma_L^d$ (mN/m) | 32.8 | 39.5 | 37 | 21.8 | 26.4 |
| $\gamma_L^p$ (mN/m) | 16 | 18.7 | 26.4 | 51 | 9 |
| $\gamma_L$ (mN/m) | 48.8 | 58.2 | 63.4 | 72.8 | 35.4 |

The results of contact angle measurements are plotted according to eq. 1 and shown in FIGS. 4A-B. FIG. 4A shows plot and fitting curves for 5% polymers and FIG. 4B shows plot and fitting curves for 10% polymers. Surfaces energies of the polymers were calculated and the results are listed in Table 4. Table 4 shows that the surface energies of all polymers include a polar component with comparable value to the dispersive component. These results confirmed the presumption that PEU-based polymers have polar properties. As can be seen, all of the polymers tested have similar surface energies, both the dispersive and polar parts. Generally, the different functional groups of these polymers did not result in significant differences in their surface energies. Considering only 5% or 10% of the total repeating units were functional groups, the low percentage of functional groups did not greatly change the surface properties of the polymers.

TABLE 4

Surface Energies of the PEUs.

| | 5% Phe | 5% Tyr | 5% CA | 10% Phe | 10% Tyr | 10% CA |
|---|---|---|---|---|---|---|
| $\gamma_S^d$ (mJ/m$^2$) | 14.8 ± 4.0 | 14.1 ± 5.2 | 12.9 ± 4.2 | 14.9 ± 4.3 | 11.4 ± 4.7 | 14.4 ± 4.7 |
| $\gamma_S^p$ (mJ/m$^2$) | 13.2 ± 4.0 | 15.3 ± 5.8 | 16.5 ± 5.0 | 13.7 ± 4.5 | 19.1 ± 6.5 | 15.3 ± 5.2 |
| $\gamma_S$ (mJ/m$^2$) | 28.0 ± 5.7 | 29.4 ± 7.8 | 29.4 ± 6.5 | 28.6 ± 6.2 | 30.5 ± 8.0 | 29.7 ± 7.0 |

Surface Energy Studies.

Surface energy is an important parameter to understand interfacial interactions between materials. Surface energy of a polymer can be estimated from contact angle measurements. The following equation was used to calculate the surface energies of PEUs:

$$\frac{(1+\cos\theta_{LP})\gamma_L}{2\sqrt{\gamma_L^d}} = \sqrt{\gamma_S^d} + \sqrt{\frac{\gamma_L^p}{\gamma_L^d}}\sqrt{\gamma_S^p} \quad (1)$$

where $\theta_{LP}$ is the Young's contact angle, $\gamma_L$ is the liquid surface tension, $\gamma_L^d$ is the dispersion component of liquid surface tension, $\gamma_L^p$ is the polar component of liquid surface tension, $\gamma_S^d$ is the dispersion component of polymer surface energy and $\gamma_S^p$ is the polar component. By measuring contact angle with different probe liquids and fitting the data using eq. 1, the dispersion and polar components of polymer surface energy can be obtained from the slope and intercept. The liquids used in this study and there properties are listed in Table 3.

Lap-Shear Adhesion Measurements.

Adhesion properties of these PEU-based polymers were examined in a lap shear configuration by bonding two mirror polished aluminum adherends together. Lap shear is a commonly used adhesion bonding test 5% and 10% functionalized PEU polymers were tested at ambient temperature. To study the adhesion under physiological condition, the 5% functionalized polymers were also tested at 37° C. Lap-shear results for all polymers are provided in FIG. 5A-B.

FIG. 5A, indicates that 5% Phe and 5% Tyr have lap-shear adhesion strengths of 0.80±0.22 MPa, and 0.84±0.19 MPa, respectively. When the phenylalanine containing segments were increased to 10%, lap-shear adhesion strength near 0.92 MPa was achieved. PEUs with increased tyrosine units (10% Tyr) had 1.08±0.22 MPa of lap-shear adhesion strength. The difference between these four polymers was minimal, indicating the incorporation of phenol groups as side chains did not result in a significant difference in adhesive strength. Similarly, the 5% increase on both PHE and Tyr functional segments did not influence the lap-shear strength. With regard to the PEUs bearing catechol groups, 5% functional group incorporation lead to an increase in the adhesive strength to 1.47±0.43 MPa, while the PEU with 10% CA groups exhibited a slightly increase in adhesive strength properties to 1.18±0.17 MPa compared to Phe or Tyr based PEUs. Nevertheless, catechol group incorporation leads to an increase in the lap-shear adhesion strength. The adherends testing polymers with phenylalanine, tyrosine and catechol functional units presented a majority of cohesive failure type. This indicates that these PEUs have relatively strong interactions with aluminum surfaces. It is believed that these interactions could be polar interactions or hydrogen bonding, considering the fact that these polymers a have relatively large polar component of surface energy and ester/urea bonds. The lap shear adhesion strength was determined by cohesive strength of polymer between adherends. Thus, it is believed that the slightly increased lap-shear adhesion for catechol polymers may come from increased mechanical strength of the polymer.

It is known that catechol groups are able to form stable linkages when the cross-linker, $N(C_4H_9)_4(IO_4)$, is introduced to the system. In these experiments, a 0.3 equivalent of cross-linker relative to catechol groups was chosen for cross-linking. This ratio has been shown to yield the strongest adhesion for polymers mimicking mussel adhesive proteins. The addition of cross-linker into 5% CA increased the lap-shear adhesion strength to 2.46±1.03 MPa, while for 10% CA, the adhesive strength dropped to around 0.57 MPa, as shown in FIG. 5A. Adhesive failure was observed for these two measurements, which was different compared to PEUs without cross-linking treatment. FIG. 6A-6B shows images of adherends with different failure types. Cross-links formed in polymer with 5% catechol groups increased the cohesive strength of the material and increased lap-shear adhesion strength. It is thought that for 10% CA, the decreased adhesion strength indicated an increase in cross-linking affected the lap-shear adhesive strength of the material. Cohesion and adhesion should be balanced to obtain optimal adhesive performance.

To compare the PEU adhesives with commercial glues, the lap-shear adhesion of ethyl cyanoacrylate (Super Glue Corp., CA) and epoxy (5 minutes setting epoxy, Super Glue Corp., CA) was measured under identical conditions (e.g., quantity of glue, substrate and cure conditions). Cyanoacrylate and epoxy showed adhesion of 3.0±1.8 MPa and 6.3±0.6 MPa respectively. The bonding strength of the cross-linked 5% catechol functionalized PEU adhesive is close to cyanoacrylate, but somewhat weaker than the epoxy.

When adhesion measurements were performed at 37° C., all of the 5% polymers (5% Phe, 5% Tyr and 5% CA) showed decreased lap-shear adhesion as shown in FIG. 5B, and the failure type remained cohesive. Compared with ambient temperature tests, the elevated temperature resulted in weaker cohesion strength of these materials and lead to decreased lap-shear adhesive strength. This was confirmed by mechanical test results of 5% Phe. See, FIG. 7 and Table 5. The Young's modulus of 5% Phe decreased from 3.0±1.1 MPa to 1.8±0.2 MPa when testing temperature increased from room temperature to 37° C., indicating decreased mechanical strength of the polymer under elevated temperature. For 5% CA after cross-linking, the failure type was also adhesive. The decreased adhesion could result from more cross-links or more dynamic cross-links formed at 37° C. compared to those at room temperature. This led to a lower affinity to adherends and hence decreased laps-shear adhesive strength.

TABLE 5

Mechanical properties of 5% Phe.

| | E' (MPa) | Stress at break (MPa) | Strain at break (%) |
|---|---|---|---|
| Test at R.T. | 3.0 ± 1.1 | 2.9 ± 0.7 | 457.0 ± 5.5 |
| Test at 37° C. | 1.8 ± 0.2 | 2.2 ± 0.4 | 693.0 ± 17.8 |

Lap shear adhesion tests of polymers on porcine skins were performed to evaluate the adhesives' possible applications on skin mimics. With the biological similarity to human dermis, porcine skins are commonly used for biomedical experiments. 5% functionalized PEU adhesive polymers were chosen because they have shown relatively strong adhesion on aluminum adherends, especially after cross-linking. The lap-shear adhesion results are shown in FIG. 8. PEU adhesive polymers with phenylalanine, tyrosine and catechol functional groups yielded weaker lap-shear adhesion strengths of around 3 kPa. The addition of cross-linker improved the lap-shear adhesive strength to about 9 kPa, which was very close to commercial TISSEEL® fibrin glue. All of the tests performed on porcine skins showed adhesive failure type. The adhesive strength was comparable to other types of adhesives, such as poly(acrylic acid) based adhesive, but it is lower than other recently reported catechol functionalized polymers. All the un-cross-linked polymers showed limited adhesion to the porcine skins. The introduction of catechol did not result in improved adhesion, although it is know that catechol groups have higher bonding capability to tissues. The weak bonding might result from the low percentages of catechol groups and the relatively high boiling point solvent (dioxane) that was used here. The addition of cross-linker resulted in higher lap-shear adhesive strength. It is believed that this may be due to increased interaction between polymer and porcine skin, which could result from a Michael-type addition between quinone form of catechol groups and thiol groups from porcine skins.

Work of Adhesion.

To measure the interfacial or intrinsic strength of an adhesive bond between solids is a fundamental issue in the science of adhesion. JKR-type experiments based on the JKR theory of contact mechanics have been developed to measure the intrinsic strength of adhesive bonds between solids. The work of adhesion has been a key thermodynamic parameter to characterize the interactions between two dissimilar surfaces. The work of adhesion of these PEU based polymer adhesives was determined in the framework of JKR contact mechanics. For the contact between a hemispherical probe and a flat surface, the JKR model predicts the radius (a) of contact deformation resulting from the joint influences of surface and external forces. They are related by eq 2:

$$a^3 = \frac{R}{K}\left[F + 3\pi RW + \sqrt{6\pi RWF + (3\pi RW)^2}\right] \tag{2}$$

Wherein R is the radius of the probe, K is the combined elastic modulus, W is the work of adhesion and F is the applied load. A polydimethylsiloxane (PDMS) lens were used as the soft probe. The radius of contact was obtained by analyzing the contact spots. The forces (F) were recorded by a force sensor. The cubic contact radius versus force curves for the measurements between PDMS probe and 5% functionalized PEU polymer adhesives shown in FIG. 9A-C. By fitting the loading curve with the JKR model, the work of adhesion (W) and the elastic modulus (K) were obtained. The work of adhesion as a function of composition was summarized in Table 6.

Since PDMS mainly has dispersive interactions with other surfaces, the work of adhesion between a PDMS lens and PEU polymer films can be estimated by eq 3:

$$W_{theo} = 2\sqrt{\gamma_{PDMS} \cdot \gamma_S^d} \quad (3)$$

$\gamma_{PDMS}$ is the surface energy of PDMS and a value of 22 $mJ/m^2$ was used, $\gamma_S{}^d$ is the dispersive component of surface energy of the polymer. The work of adhesion was calculated and listed in Table 6. Functionalized polymers (5%) were investigated to study the adhesion properties since they showed higher lap-shear adhesion on aluminum adherends when cross-linked. All of the polymers showed a JKR work of adhesion in the range of 31 $mJ/m^2$ to 34 $mJ/m^2$ and were in good agreement of the surface energy results measured by contact angle. Almost no difference on work of adhesion was observed for the polymers with phenylalanine, tyrosine and catechol functional groups. Since there are only dispersive interactions between the PDMS lens and the polymer surface, these results demonstrate that the polymers have similar dispersive interactions with the PDMS lens. As shown in FIG. 9A-C, a significant amount of hysteresis between loading curves and unloading curves were observed. The hysteresis indicates non-equilibrium processes such as energy used in bulk deformations aside from the thermodynamic work of adhesion needed in separating the two surfaces. Although the approach shows dispersive interaction, polar interactions may contribute to adhesive hysteresis similar to PDMS-glass.

TABLE 6

JKR Work of Adhesion of 5% Polymers.

| | Calculated W ($mJ/m^2$) | Measured W ($mJ/m^2$) |
|---|---|---|
| 5% Phe | 36.2 ± 1.3 | 31.4 ± 0.8 |
| 5% Tyr | 35.2 ± 2.4 | 33.8 ± 1.0 |
| 5% CA | 33.7 ± 1.8 | 33.1 ± 0.8 |

In sum, 0, the adhesion properties and surface energies of PEUs adhesives bearing phenylalanine, tyrosine and catechol functional units were characterized and compared with all types of PEUs show relatively strong adhesion on aluminum adherends, especially the materials possessing catechol functional units. Meanwhile, cross-linking treatment of catechol containing PEUs lead to a significant increase in lap-shear adhesion strength. Cross-linked catechol functionalized PEU-based adhesives showed comparable lap-shear adhesive strength to commercial fibrin glue on porcine skin. The JKR work of adhesion matches well with surface energy studies. With the advantageous tunable mechanical property and degradability, it is believed that these bio-mimetic adhesives may provide a new clinical option for further development.

EXAMPLES

The following examples are offered to more fully illustrate the invention, but are not to be construed as limiting the scope thereof. Further, while some of examples may include conclusions about the way the invention may function, the inventors do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Materials 1,8-octanediol, L-phenylalanine, L-leucine, N-Boc-O-benzyl-L-tyrosine, 3,4-dihydroxyhydrocinnamic acid, thionyl chloride, 2,2-dimethoxypropane, triphosgene, calcium hydride, p-toluenesulfonic acid monohydrate, trifluoroacetic acid, palladium on carbon (10 wt. % loading), triisopropylsilane, tetrabutylammonium periodate ($Bu_4N(IO_4)$) were purchased from Sigma-Aldrich or Alfa Aesar. N,N'-diisopropylcarbodiimide (DIC) and N-(3-dimethylaminopropyl)-N'-ethylcarbodiimide hydrochloride (EDC) were obtained from Oakwood Products, Inc. Porcine skins were purchased from a local grocery store. Acetonide-protected 3,4-dihydroxyhydrocinnamic acid and 4-(dimethyl amino) pyridinium 4-toluenesulfonate (DPTS) were synthesized following procedures in the literature and described in detail in the Examples that follow. Unless otherwise stated, all solvents used were reagent grade and all chemicals were used as received without further purification.

Polydimethylsiloxane (PDMS) lenses for JKR measurements were prepared from Sylgard®184 elastomer kit purchased from Dow Corning and used as received. A ratio of base to curing agent (10:1 by mass) was mixed with a spatula. The PDMS mixtures were degassed under vacuum to remove air bubbles. Lens preparation involved placing 1 to 3 mg of mixture under water in a polystyrene dish using a blunt tipped syringe needle. Elastomeric sheets were prepared by weighing 5.5 grams of elastomer mixture in polystyrene dishes (60 mm×15 mm). Sheets and lenses were cured simultaneously at 65° C. for 4 h. After curing, water was removed from the dish and nitrogen gas dried the lenses. The lenses and sheet were extracted of unreacted oligomers in a glass petri dish with toluene and a piece of filter paper. The solvent and filter paper were changed at least three times over seven days. After removing excess toluene, the extracted lenses cured under vacuum for an additional 4 h at 65° C.

General Procedures $^1H$ and $^{13}C$ NMR spectra were recorded using Varian NMR spectrophotometer (300 MHz or 500 MHz). Number-average molecular mass ($M_n$), weight-average molecular mass ($M_w$), and molecular mass distribution ($Đ_M$) were determined by size exclusion chromatography (SEC), and molecular mass values were determined by light scattering. The SEC analysis was performed on a Waters CHM column heater module equipped with three HR-Styragel columns and a triple detector system. THF was used as eluent at a flow rate of 1.0 mL/min at 35° C. Thermogravimetric analysis (TGA) measurements were performed over an interval of ambient temperature to 600° C. at a heating rate of 10° C./min under a N, atmosphere. Differential scanning calorimetry (DSC) were performed on TA Q2000 from −50 to 200° C. at a scanning rate of 10° C./min.

Example 1

Synthesis of 2,2-Dimethyl-1,3-benzodioxole-5-propanoic acid XXI 2,2-Dimethyl-1,3-benzodioxole-5-propanoic acid XXI was synthesized as set forth in Scheme 9, below.

Scheme 9

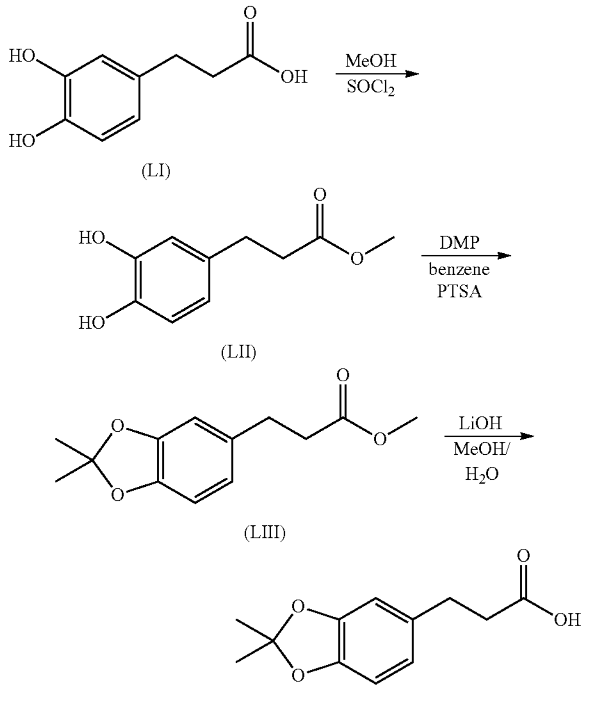

(LI) (LII) (LIII) (XXI)

Synthesis of methyl 3-(3,4-dihydroxyphenyl)propanoate LII 3,4-dihydroxyhydrocinnamic acid LI (12.5 g, 68.6 mmol) was dissolved in 100 mL anhydrous MeOH and cooled with ice bath. Thionyl chloride (13.0 mL, 171.5 mmol) was added dropwise with stirring. Ice bath was removed after 30 min and the reaction was stirred at r.t. for 24 h. Solvent was removed by rotary evaporation. Dried under high vacuum gave product as a dark blue viscous oil quantitatively. The oily product became solid after being placed in the freezer. $^1$H NMR (500 MHz, $CDCl_3$): 2.61 (t, J=7.70 Hz, 2H), 2.83 (t, J=7.70 Hz, 2H), 3.69 (s, 3H), 5.69 (br. s., 2H), 6.60 (dd, J=8.07, 1.96 Hz, 1H), 6.71 (d, J=1.96 Hz, 1H), 6.77 (d, J=8.07 Hz, 1H). $^{13}$C NMR (125 MHz, $CDCl_3$): 30.25, 35.94, 51.89, 115.43, 120.51, 133.19, 142.12, 143.66, 174.38.

Synthesis of 2,2-Dimethyl-1,3-benzodioxole-5-propanoic acid methyl ester LII

Methyl 3-(3,4-dihydroxyphenyl)propanoate LI. (5.18 g, 26.4 mmol) and 2,2-dimethoxypropane (13 mL, 106 mmol) were added to 200 mL anhydrous benzene in a 250 mL two-neck round bottom flask. One neck of the flask was equipped with Soxhelet extractor and the other neck was sealed with a septum for sampling. The thimble in the extractor was filled with granular anhydrous $CaCl_2$ to trap MeOH and $H_2O$. The mixture was flushed with argon for 10 min and then heated to reflux under $N_2$ for 5 min. p-Toluenesulfonic acid monohydrate (PTSA, 0.25 g, 1.3 mmol) was added quickly and the reaction was monitored by the ferric chloride test. The reaction was stopped and cooled to room temperature once a negative test was achieved (about 3 hrs). The yellow reaction mixture was filtered through a short silica-gel column and washed with DCM. The combined filtrate and washings were concentrated via rotovap and purified by silica-gel column. The eluent was DCM/hexane (1/50, v/v) followed by EtOAc/hexane (1/25, v/v). Yellow oil (5.5 g, 88%) was obtained as the product. $^1$H NMR (300 MHz, $CDCl_3$): 1.65 (s, 6H), 2.58 (t, J=7.90 Hz, 2H), 2.85 (t, J=7.76 Hz, 2H), 3.67 (s, 3H), 6.56-6.67 (m, 3H). $^{13}$C NMR (75 MHz, $CDCl_3$): 25.81, 30.71, 36.05, 51.57, 108.01, 108.52, 117.63, 120.39, 133.60, 145.79, 147.45, 173.31.

Synthesis of 2,2-Dimethyl-1,3-benzodioxole-5-propanoic acid XXI. LiOH aqueous solution (0.33 g, 13.9 mmol dissolved in 8 mL $H_2O$) was added to a methanol solution of 2,2-Dimethyl-1,3-benzodioxole-5-propanoic acid methyl ester LII (1.64 g, 6.93 mmol dissolved in 8 mL of methanol) in portions. After overnight reaction, methanol was removed by rotovap. The pH of the remaining solution was adjusted to 5-6 by 2 M HCl. The mixture was then extracted with EtOAc for three times. Combined organic layers was dried with $Na_2SO_4$ and evaporated in vacuo to obtain a white solid as product (1.30 g, 84%). $^1$H NMR (500 MHz, $CDCl_3$): 1.65 (s, 6H), 2.55-2.63 (m, 2H), 2.79-2.88 (m, 2H), 6.55-6.66 (m, 3H), 9.34 (br. s., 1H). $^{13}$C NMR (125 MHz, $CDCl_3$): 25.79, 30.72, 36.70, 108.01, 108.53, 117.60, 120.37, 133.61, 145.80, 147.48, 179.38.

Example 2

Synthesis of 4-(Dimethylamino)pyridinium 4-Toluenesulfonate (DPTS)

Hydrated p-toluenesulfonic acid (PTSA, 12.00 g, 63.1 mmol) was dried by azeotropic distillation of a toluene solution using a Dean-Stark trap. 4-(Dimethylamino)pyridinium (8.50 g, 49.4 mmol) dissolved in hot toluene was added to the above solution at about 60° C. After stirring for 1 hr, the solution was cooled to room temperature, filtered, washed with toluene and vacuum dried. After recrystallization with dichloromethane for three times, the product was obtained as a white crystal (16.03 g, 86%). $^1$H NMR (500 MHz, DMSO-$d_6$): 2.28 (s, 3H), 3.17 (s, 6H), 6.97 (d, J=7.82 Hz, 2H), 7.11 (d, J=7.83 Hz, 2H), 7.47-7.51 (m, 2H), 8.18-8.23 (m, 2H), 13.19 (br. s., 1H). $^{13}$C NMR (125 MHz, DMSO-$d_6$): 21.23, 107.43, 125.95, 128.51, 138.10, 139.57, 146.15, 157.42.

Example 3

Synthesis of Di-p-toluenesulfonic Acid Salt of Bis-L-leucine-octane-1,8-diester XL (M1)

1,8-octanediol (10.00 g, 0.068 mol), L-leucine (20.46 g, 0.156 mol), p-toluenesulfonic acid monohydrate (31.07 g, 0.163 mol) and toluene (200 mL) were mixed in a 500 mL round-bottom flask equipped with Dean-Stark trap and a magnetic stir bar. The system was heated to reflux for 20 h. After the reaction mixture was cooled to ambient temperature, the product was filtered and washed with diethyl ether. The solid product was recrystallized with water for three times to yield 42.9 g (yield 88%) white powder as the product. $^1$H NMR (300 MHz, DMSO-$d_6$): 0.89 (d, J=5.86 Hz, 12H), 1.28 (br. s., 8H), 1.51-1.65 (m, 8H), 1.66-1.78 (m, 2H), 2.29 (s, 6H), 3.98 (t, J=7.03 Hz, 2H), 4.07-4.23 (m, 4H), 7.12 (dd, J=8.49, 0.59 Hz, 4H), 7.42-7.54 (m, 4H), 8.30 (br. s., 6H). $^{13}$C NMR (125 MHz, DMSO-$d_6$): 21.22, 22.37, 22.58, 24.26, 25.58, 28.32, 28.89, 51.09, 66.06, 125.93, 128.51, 138.18, 145.94, 170.38.

Example 4

Synthesis of Di-p-toluenesulfonic Acid Salt of Bis-L-phenylalanine-octane-1,8-diester XLI (M2)

1,8-octanediol (10.00 g, 0.068 mol), L-phenylalanine (25.79 g, 0.156 mol), p-toluenesulfonic acid monohydrate (31.07 g, 0.163 mol) and toluene (200 mL) were mixed in a 500 mL round-bottom flask equipped with Dean-Stark trap and a magnetic stir bar. The system was heated to reflux for 20 h. After the reaction mixture was cooled to ambient temperature, the product was filtered and washed with diethyl ether. The solid product was dissolved in 3 L of hot water and decolored using activated carbon black (2.00 g) for 2-3 min. After hot filtration and cooling to room temperature, a white solid product was obtained by vacuum filtration. The product was then recrystallized with water for three times to yield 45.9 g (yield 86%) white powders as product. $^1$H NMR (500 MHz, DMSO-$d_6$): 1.08-1.22 (m, 8H), 1.37-1.49 (m, 4H), 2.29 (s, 6H), 3.02 (dd, J=14.06, 7.95 Hz, 2H), 3.14 (dd, J=13.94, 5.87 Hz, 2H), 3.98-4.08 (m, 4H), 4.28 (dd, J=7.83, 6.11 Hz, 2H), 7.11 (dd, J=8.44, 0.61 Hz, 4H), 7.20-7.36 (m, 10H), 7.48 (d, J=7.83 Hz, 4H), 8.36 (br. s., 6H). $^{13}$C NMR (125 MHz, DMSO-$d_6$): 21.25, 25.49, 28.20, 28.86, 36.65, 53.83, 65.96, 125.99, 127.65, 128.65, 128.97, 129.76, 135.18, 138.56, 145.46, 169.47.

Example 5

Synthesis of Bis-N-Boc-0-benzl-L-tyrosine-octane-1,8-diester XXXVI (a=7)

1,8-octanediol (1.64 g, 11.2 mmol), N-Soc-0-benzyl-L-tyrosine (10.00 g, 26.9 mmol) and DPTS (0.66 g, 2.24 mmol) were dissolved in 60 mL anhydrous dichloromethane under $N_2$. The temperature was lowered to 0° C. with an ice bath after all the solids were dissolved. DIC (4.9 mL, 31.36 mol) was added via syringe in one portion. The reaction was stirred overnight while the temperature gradually increased to room temperature. The mixture was filtered, concentrated and dissolved in $CHCl_3$. The solution was washed with 5% HCl twice, brine once, dried over $Na_2SO_4$ and solvent was removed in vaccuo. A light yellow solid (9.31 g, 97%) was obtained with column chromatography on silica gel in MeOH/$CHCl_3$ (5/95, v/v). $^1$H NMR (500 MHz, DMSO-$d_6$): 1.31 (s, 8H), 1.43 (s, 18H), 1.55-1.65 (m, 4H), 2.96-3.10 (m, 4H), 4.03-4.15 (m, 4H), 4.53 (d, J=6.85 Hz, 2H), 4.97 (d, J=7.58 Hz, 2H), 5.04 (s, 4H), 6.87-6.94 (m, 4H), 7.02-7.09 (m, 4H), 7.30-7.46 (m, 10H). $^{13}$C NMR (125 MHz, DMSO-$d_6$): 25.78, 28.32, 28.48, 29.07, 37.57, 54.57, 65.36, 70.02, 114.90, 127.40, 127.93, 128.55, 130.34, 137.03, 157.90.

Example 6

Synthesis of Di-hydrochloric Acid Salt of Bis-O-benzl-L-tyrosine-octane-1,8-diester XLII (M3)

80 mL HCl solution (4.0 M in dioxane) was added to 7.60 g (8.91 mmol) Sis-N-Soc-O-benzl-L-tyrosine-octane-1,8-diester and the mixture was stirred overnight under $N_2$. The mixture was concentrated and freeze-dried. The obtained solid was washed three times with diethyl ether to yield a light yellow powder (6.1 g, 94%) as product. $^1$H NMR (500 MHz, DMSO-$d_6$): 1.09-1.24 (m, 8H), 1.35-1.50 (m, 4H), 3.00 (dd, J=13.94, 8.07 Hz, 2H), 3.16 (dd, J=14.06, 5.50 Hz, 2H), 3.99 (t, J=5.22 Hz, 4H), 4.13 (dd, J=7.95, 5.75 Hz, 2H), 5.06 (s, 3H), 6.90-7.01 (m, 4H), 7.15 (d, J=8.56 Hz, 4H), 7.28-7.49 (m, 10H), 8.73 (br. s., 6H). $^{13}$C NMR (125 MHz, DMSO-$d_6$): 25.60, 28.27, 28.96, 35.63, 53.76, 65.68, 66.81, 69.59, 115.23, 127.22, 128.02, 128.27, 128.87, 130.95, 137.50, 158.01, 169.56.

Example 7

Interfacial Polymerization

General Procedures. As shown in Scheme 8, 1,8-octanediol-L-phenylalanine and 1,8-octanediol-L-leucine-based poly(ester urea) (Phe-PEU), 1,8-octanediol-O-benzyl-L-tyrosine and 1,8-octanediol-L-leucine-based poly(ester urea) (Tyr(Bzl)-PEU) were synthesized using the following procedure. Monomers (20.4 mmol in total, 1 equiv) and sodium carbonate (4.54 g, 42.8 mmol, 2.1 equiv) were dissolved in 200 mL of water in a four-neck 2 L round-bottom flask equipped with mechanical stirring. The cloudy solution was placed in a 35° C. water bath and stirred for 1 h. The system was cooled to 0° C. with an ice bath. Additional sodium carbonate (2.38 g, 22.4 mmol, 1.1 equiv) dissolved in 40 mL water was added. When the temperature of reaction mixture dropped to 0° C., triphosgene (2.22 g, 7.5 mmol, 0.37 equiv) dissolved in 45 mL chloroform was added quickly under vigorous stirring. The cooling bath was removed after 30 min of stirring. An additional aliquot of triphosgene solution (0.40 g, 1.4 mmol, 0.067 equiv, in 15 mL chloroform) was added dropwise over an additional 30 min period. After 2 h, the reaction mixture was transferred to a separatory funnel. After washing with water, the organic phase was precipitated into hot water under mechanical stirring. After cooling to ambient temperature, the polymer was obtained after filtration and vacuum drying.

10% Phe XIII (PEU with monomers feed ratio XLI:XL (M2:M1)=10:90). $^1$H NMR (500 MHz, DMSO-$d_6$): 0.77-0.94 (m, 108H), 1.20-1.67 (m, 174H), 2.91 (t, J=6.60 Hz, 4H), 3.91-4.06 (m, 40H), 4.08-4.18 (m, 18H), 4.37 (d, J=7.09 Hz, 2H), 6.22-6.30 (m, 18H), 6.48 (d, J=8.07 Hz, 2H), 7.14-7.29 (m, 10H).

5% Phe X (PEU with monomers feed ratio XLI:XL (M2:M1)=5:95) has the same NMR shifts as 10% Phe, only the integrations are different. 5% Tyr(Bzl) (PEU with monomers feed ratio M3:M1=5:95) and 10% Tyr(Bzl) (PEU adhesive copolymer with monomer feed ratio XLII:XL (M3:M1)=10:90) have the same NMR shifts. All the PEU adhesive polymers possess the same backbone structure and share the same L-leucine segment. The chemical shifts of the different functionalized units are described in the following parts.

10% Tyr(Bzl) (PEU adhesive copolymer with 10% benzyl-protected tyrosine segments). $^1$H NMR (500 MHz, DMSO-$d_6$): 5.04 (s, 4H, —$ArOCH_2$—Ar), 6.89 (d, J=8.31, 4H, tyrosine unit aromatic), 7.05 (d, J=8.56 Hz, 4H, tyrosine unit aromatic), 7.26-7.44 (m, 10H, Bzl unit aromatic H).

Synthesis of 10% Tyr XIV (PEU adhesive copolymer with 10% tyrosine segments). 10% Tyr(Bzl) (6.00 g) was dissolved in DMF (60 mL), followed by the addition of palladium/carbon (0.80 g, 10 wt % of Pd). The suspension was shaken under hydrogen (60 psi) at 40° C. for 24 hrs. After filtration with Celite 545, the solution was concentrated and precipitated into water. A white solid (5.10 g, 89%) was obtained after filtration and vacuum dry. $^1$H NMR (500 MHz, DMSO-$d_6$): 6.64 (d, J=8.56 Hz, 4H, aromatic H), 6.92 (d, J=8.56 Hz, 4H, aromatic H), 9.17 (s, 2H, —Ar—OH).

Synthesis of 10% CA(AN) XXV (PEU adhesive copolymer with 10% acetonide protected catechol segments). 10% Tyr (1.00 g), acetonide protected 3,4-dihydroxyhydrocinnamic acid (0.21 g, 0.92 mmol) and DPTS (0.054 g, 0.18 mmol) were dissolved in 10 mL DMF under $N_2$. The temperature was cooled to 0° C. with ice-water bath and EDC (0.18 g, 0.92 mmol) was added in one portion. The mixture was stirred for 36 h at room temperature and then precipitated into water (pH=8-9, adjusted by addition of $NaHCO_3$). A white solid (1.01 g, 92%) was obtained after filtration and vacuum dry. $^1$H NMR (500 MHz, DMSO-$d_6$): 2.82 (dd, J=12.84, 5.75 Hz, 8H, —$OOCCH_2CH_2Ar$—), 6.62-6.67 (m, 6H, aromatic H from protected catechol), 6.93 (d, J=8.31 Hz, 4H, aromatic H from tyrosine unit), 7.15 (d, J=8.31 Hz, 4H, aromatic H from tyrosine unit).

Synthesis of 10% CA XV (PEU adhesive copolymer with 10% catechol segments). 10% CA(AN) (1.00 g) was added to 10 mL degassed $CHCl_3$ in a 50 mL round-bottom flask equipped with stir bar under argon. After the polymer was dissolved, a mixture of 4 mL trifluoroacetic acid, 0.2 mL $H_2O$ and 5 drops of triisopropylsilane was added. The mixture was stirred under argon for 2 h at room temperature. It was then concentrated and precipitated into cold diethyl ether. A white solid (0.79 g, 80%) was obtained after vacuum dry. $^1$H NMR (500 MHz, DMSO-$d_6$): 2.77 (br. s., 8H, —$OOCCH_2CH_2Ar$—), 6.47-6.53 (m, 2H, aromatic H from catechol, overlaps with —$OCNHCH(CH_2Ar)CO$—), 6.62-6.66 (m, 4H, aromatic H from catechol), 6.94 (d, J=8.31 Hz, 4H, aromatic H from tyrosine unit), 7.16 (d, J=8.31 Hz, 4H, aromatic H from tyrosine unit).

5% Tyr XI, 5% CA(AN) XXIV and 5% CA XII containing 5% functional units were synthesized using the same procedures described above for 10% Tyr(Szl) except that a PEU adhesive copolymer having 5% benzyl protected tyrosine segments (5% Tyr(Szl) was used in place of the PEU adhesive copolymer having 10% benzyl protected tyrosine segments as set forth above. The 5% Tyr(Szl) was synthesized using the method described above, with a 5:95 molar ratio of the di-hydrochloric acid salt of bis-O-benzl-L-tyrosine-octane-1,8-diester XLII (M3) (See Examples 5 & 6, above) to the di-p-toluenesulfonic acid salt of bis-L-leucine-octane-1,8-diester XL (M1) (See Example 3, above).

Example 8

Mechanical Property Measurements of 5% Phe

Thin films of 5% Phe were fabricated using a vacuum compression machine (TMP Technical Machine Products Corp.). The machine was preheated to 74° C. and 0.9 g of the polymer was added into the mold. After 5 minutes of melting, the system was degassed three times. 10,000 lbs, 15,000 lbs, 20,000 lbs, 25,000 lbs of pressure were applied for 4 minutes respectively. After that, the mold was cooled down with 1000 psi of pressure to prevent the wrinkle on the film's surface. The films were visually inspected to ensure that no bubble were present.

The elastic modulus of each polymer film was obtained using Instron (Instron 5567 Universal Testing Machine with a chamber for temperature control). The gauge length was set as 12 mm and the crosshead speed was 3 mm/min. The dimensions of the specimens were 20 mm in length, 4.5 mm in width and 0.6 mm in thickness. The tensile tests were carried out at room temperature (25±1° C.) with rectangular samples and at physiological temperature (37±1° C.) with rectangular samples. (See Table 5 and FIG. 7). The elastic moduli were calculated using the slope of linear fitting of the data from strain of 0% to 3%. The reported results are the average values for three individual measurements.

Example 9

Lap-Shear Adhesion Testing

Lap-shear adhesive strength experiments were completed according to the ASTM D1002 standard with a minor modification. Aluminum substrates were prepared from mirror polished aluminum plate with a thickness of 1.6 mm. Each adherend was cut into a rectangular shape, 7.50 cm long×1.25 cm wide; a centered hole of 0.64 cm diameter was drilled into each adherend 1.25 cm from one end. The adherends were washed in sequence with hexane, ethanol, acetone, deionized water and then dried overnight prior to use.

5% Phe, 5% Tyr, 5% CA (AN), 5% CA, 10% Tyr, 10% CA (AN), 10% CA polymer solutions in THF (0.2 g/mL, 25 μL) were added on one adherend and spread over the lap area. The adherends were overlapped at 1.25×1.25 cm in a lap shear configuration. For the tests with cross-linker, 20 μL 0.25 g/mL polymer solution and 5 μL $Bu_4N(IO_4)$ solution (0.3 equiv of cross-linker per catechol group, in THF) were applied. The adherends were then clipped and allowed to cure for 1 h at room temperature, 24 h at 65° C., and 1 h at room temperature. See FIG. 5A.

Lap-shear adhesion measurements were performed for 5% Phe, 5% Tyr, 5% CA(AN), 5% CA, 10% Tyr, 10% CA(AN), 10% CA using an Instron 5567 materials testing system equipped with 1000 N load cell. The adherends were pulled apart at a rate of 1.3 mm/min. The adhesive strength was obtained by dividing the maximum load (N) observed by the area of the adhesive overlap ($m^2$), giving the lap-shear adhesion in Pascals ($Pa=N\ m^{-2}$). For the 37° C. adhesion tests, the adherends were cured for 1 h at room temperature, 24 h at 65° C., and 1 h at 37° C. The measurements were conducted on Instron 5567 with a chamber to control temperature as 37±1° C. See FIG. 5B.

Porcine skins were cut into 5 cm×1.5 cm sized strips and were used without further purification or modification. Solutions 5% Phe, 5% Tyr, 5% CA(AN), 5% CA, 10% Tyr, 10% CA(AN), 10% CA in dioxane (0.2 g/mL, 20 μL) were added on both adherends and spread over the lap area. For the tests with cross-linker, 20 μL 0.25 g/mL polymer solutions and 5 μL $Bu_4N(IO_4)$ solutions (0.3 equiv of cross-linker per catechol group, in dioxane) were applied. The adherends were overlapped in a lap-shear configuration and a ~15 g weight (comprised of copper shot in a 15 mL centrifuge tube) was place on top of the joint. The overlap area of each sample was measured. The adherends were then allowed to cure for 4 h at room temperature. The lap-shear measurements were performed on Instron 5567 under room temperature. For comparison purposes, the porcine skin adherends were glued together using a commercial fibrin surgical sealant (TISSEEL®, Baxter). The TISSEEL® fibrin glue was prepared according to manufacturer's instructions, and 100 μL was applied in the same manner of PEU adhesives. All other conditions were kept the same as PEU adhesive samples. The results are shown in FIG. 8, above.

Example 10

Contact Angle Measurement

Polymer thin films of 5% Phe, 5% Tyr, 5% CA(AN), 5% CA, 10% Tyr, 10% CA(AN), 10% CA were prepared as set forth above and were spin coated on pre-cleaned glass slides from 1% (w/v) dioxane solutions. Contact angles of five liquids of known surface tensions (water, ethylene glycol, propylene glycol, formamide and glycerol) on the polymer films were measured using a Ramé-Hart contact angle goniometer. At least five measurements were performed on different spots and averaged. The measurements were conducted under room temperature. See Table 3 and FIGS. 4A-B.

Example 11

JKR Work of Adhesion Measurements

Optical microscopy measured lenses' radii using an Olympus Microscope analyzed by CellSens® software. The lens was placed on top of a thin elastomeric ribbon. A home built JKR apparatus measured the work of adhesion. The load cell was purchased from Futek, model LSB 200 with a maximum capacity of 1 N and attached to a translating stage moving in the Z direction. A fixed zig-zag glass arm was fixed to an XY translating base. The ribbon and lens were placed on the glass support and the load cell traveled toward the lens supported by the stationary glass arm.

Substrates were prepared by spin coating 1% (w/v) dioxane solutions of 5% Phe, 5% Tyr, 5% CA(AN), 5% CA, 10% Tyr, 10% CA(AN), 10% CA polymers on pre-cleaned glass slides and dried under vacuum for 2 hrs. The film thickness was around 50 nm measured by ellipsometry (VASE M-2000, J.A. Woollam Co.). The substrates were manually brought into close proximity to the rubber lens without contact and then brought into contact with a computer controlled high resolution Picometer® motor. After established contact, the lens was loaded in 0.1 to 0.2 mN intervals at 0.02 μm/s, after equilibrating for one minute. Unloading measurements were done continuously at a rate of 0.01 μm/sec. Loading and unloading rates were done at the slowest rate allowed by the instrumentation. The lens traveled an estimated distance of four to six μm one way measured by a 0-15-0 dial test indicator. Work of adhesion of PDMS-PDMS was measured prior to confirm the accuracy of the JKR instrument and the preparation of smooth PDMS lenses. See FIGS. 9A-C. The work of adhesion was calculated and listed in Table 6.

In light of the foregoing, it should be appreciated that the present invention significantly advances the art by providing a amino acid-based PEU adhesive (and related methods) that is structurally and functionally improved in a number of ways. While particular embodiments of the invention have been disclosed in detail herein, it should be appreciated that the invention is not limited thereto or thereby in as much as variations on the invention herein will be readily appreciated by those of ordinary skill in the art. The scope of the invention shall be appreciated from the claims that follow.

What is claimed is:

1. A biodegradable tissue adhesive comprising an amino acid-based poly(ester urea) having one or more catechol functional groups wherein said amino acid-based poly(ester urea) further comprises two or more polyester monomer segments; wherein each of said two or more polyester monomer segments comprise the residue of two or more amino acids separated by the residue of a diol or polyol having from 2 to 20 carbon atoms.

2. The biodegradable tissue adhesive of claim 1, wherein said amino acid-based poly(ester urea) further comprises a residue of phenylalanine or tyrosine.

3. The biodegradable tissue adhesive of claim 1 wherein the two or more amino acids in said two or more monomer segments are each selected from the group consisting of alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), serine (ser—S), threonine (thr—T), tryptophan (trp—W), tyrosine (tyr—Y), valine (val—V), benzyl protected tyrosine, BOC protected tyrosine and combinations thereof.

4. The biodegradable tissue adhesive of claim 1 wherein said at least one of said two or more polyester monomer segments contains a catechol functionalized phenylalanine or tyrosine residue.

5. The biodegradable tissue adhesive of claim 1 wherein said at least one of said two or more polyester monomer segments is branched.

6. The biodegradable tissue adhesive of claim 1, wherein said amino acid-based poly(ester urea) is a copolymer comprising:

one or more first monomer segments containing two or more catechol-functionalized amino acid residues separated by the residue of a diol or polyol having from 2 to 20 carbon atoms; and one or more second monomer segments containing two or more amino acid residues separated by the residue of a diol or polyol having from 2 to 20 carbon atoms.

7. The biodegradable tissue adhesive of claim 6 wherein said one or more first monomer segments has the formula:

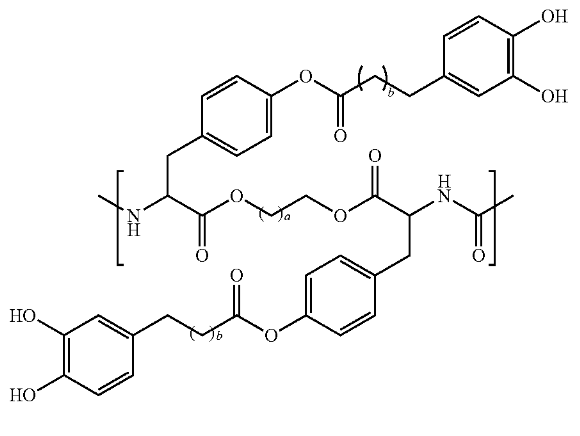

wherein a is an integer from 1 to 20 and b is an integer from 1 to 6.

8. The biodegradable tissue adhesive of claim 6 wherein the two amino acid residues of said one or more second monomer segments are residues of amino acids selected from the group consisting of alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), serine (ser—S), threonine (thr—T), tryptophan (trp—W), tyrosine (tyr—Y), valine (val—V), and combinations thereof.

9. The biodegradable tissue adhesive of claim 6 wherein said one or more second monomer segments has the formula:

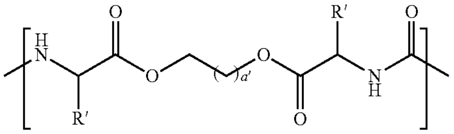

wherein R' is $—CH_3$, $—(CH_2)_3NHC(NH_2)C{=}NH$, $—CH_2CONH_2$, $—CH_2COOH$, $—CH_2SH$, $—(CH_2)_2COOH$, $—(CH_2)_2CONH_2$, $—NH_2$, $—CH_2C{=}CH—N{=}CH—NH$, $—CH(CH_3)CH_2CH_3$, $—CH_2CH(CH_3)_2$, $—(CH_2)_4NH_2$, $—(CH_2)_2SCH_3$, $—CH_2Ph$, $—CH_2OH$, $—CH(OH)CH_3$, $—CH_2—C{=}CH—NH\text{-}Ph$, $—CH_2\text{-}Ph\text{-}OH$, or $—CH(CH_3)_2$; and a' is an integer from 1 to 20.

10. The biodegradable tissue adhesive of claim 1 having the formula:

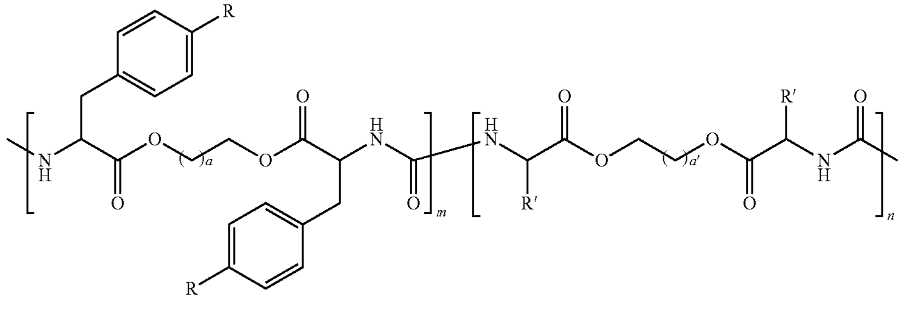

wherein R is $—OCOO(CH_2)_2C_6H(OH)_2$, $—OCOO(CH_2)_2C_6H_3(OH)_2$, $—OCOO(CH_2)_3C_6H_3(OH)_2$, $—OCOO(CH_2)_4C_6H_3(OH)_2$, $—OCOO(CH_2)_5C_6H_3(OH)_2$, $—OCOO(CH_2)_6C_6H_3(OH)_2$, and $—OCOO(CH_2)_7C_6H_3(OH)_2$; R' is $—CH_3$, $—(CH_2)_3NHC(NH_2)C{=}NH$, $—CH_2CONH_2$, $—CH_2COOH$, $—CH_2SH$, $—(CH_2)_2COOH$, $—(CH_2)_2CONH_2$, $—NH_2$, $—CH_2C{=}CH—N{=}CH—NH$, $—CH(CH_3)CH_2CH_3$, $—CH_2CH(CH_3)_2$, $—(CH_2)_4NH_2$, $—(CH_2)_2SCH_3$, $—CH_2Ph$, $—CHOH$, $—CH(OH)CH_3$, $—CH_2—C{=}CH—NH\text{-}Ph$, $—CH_2\text{-}Ph\text{-}OH$, or $—CH(CH_3)_2$; a and a' are each an integer from about 1 to about 20; and m and n are mole fractions.

11. The biodegradable tissue adhesive of claim 1 having a formula selected from the group consisting of:

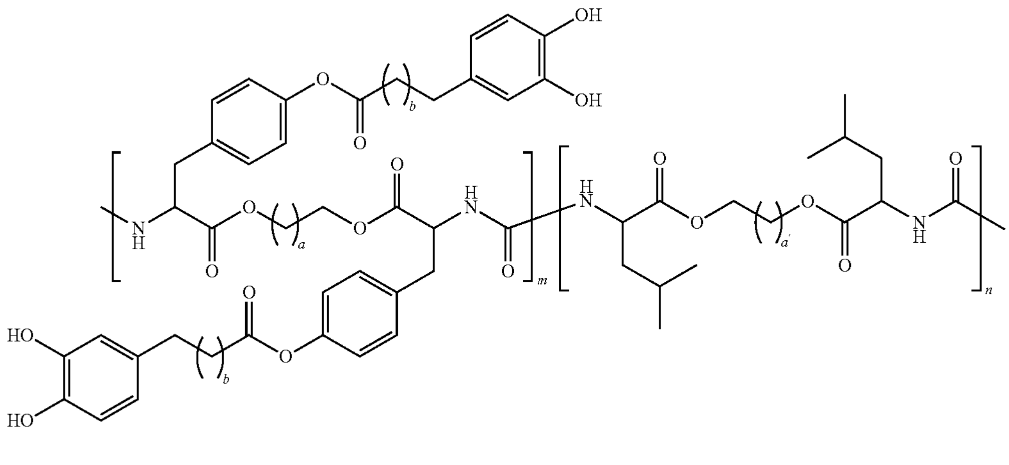
,

-continued
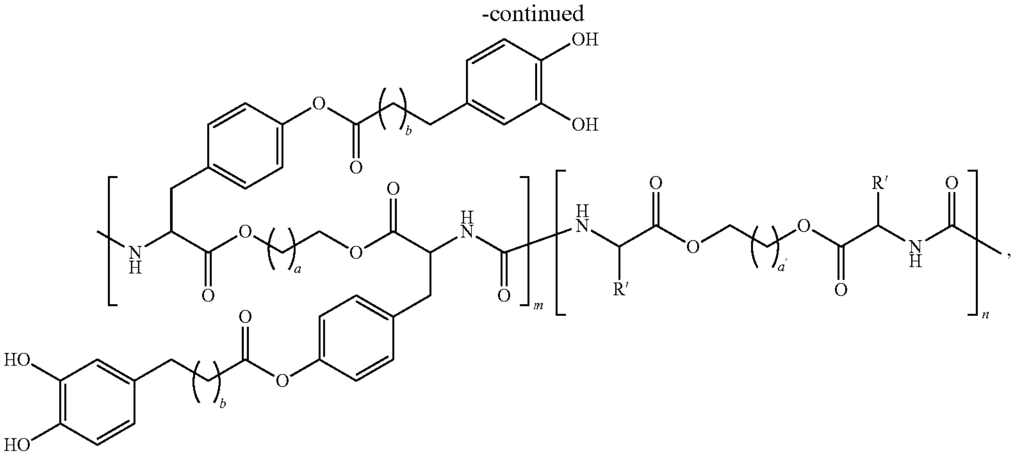
,
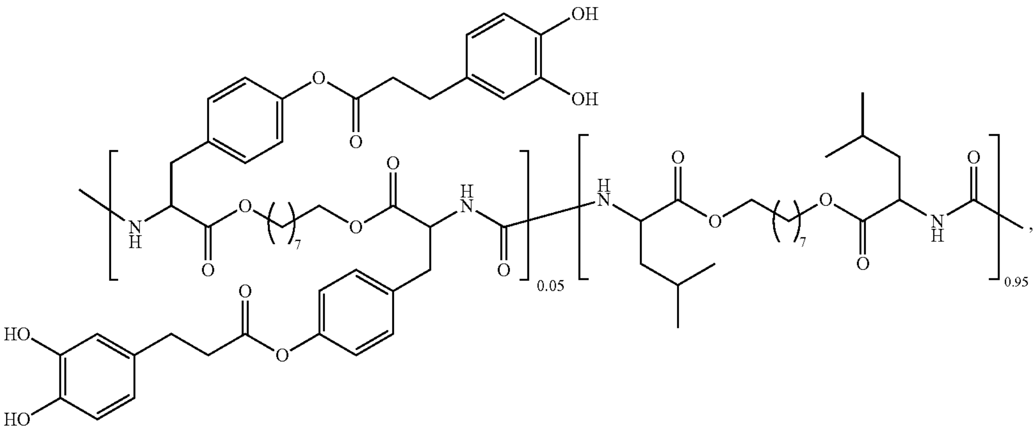
,
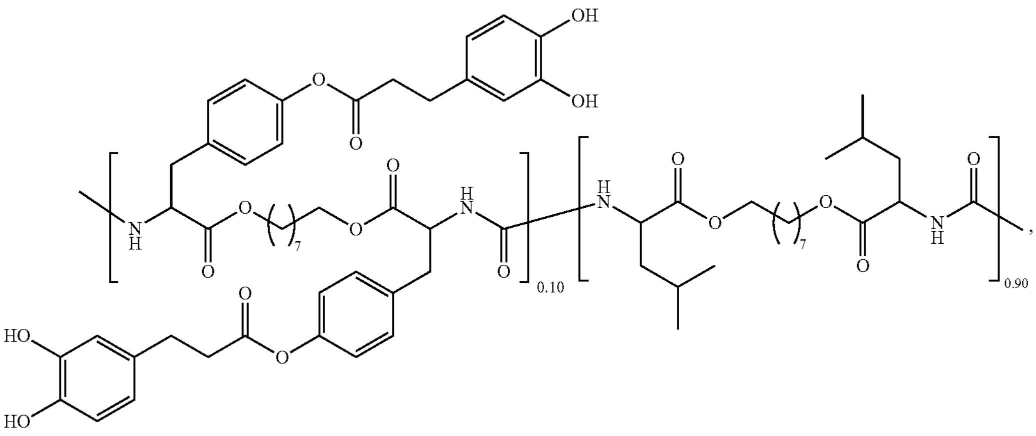
,
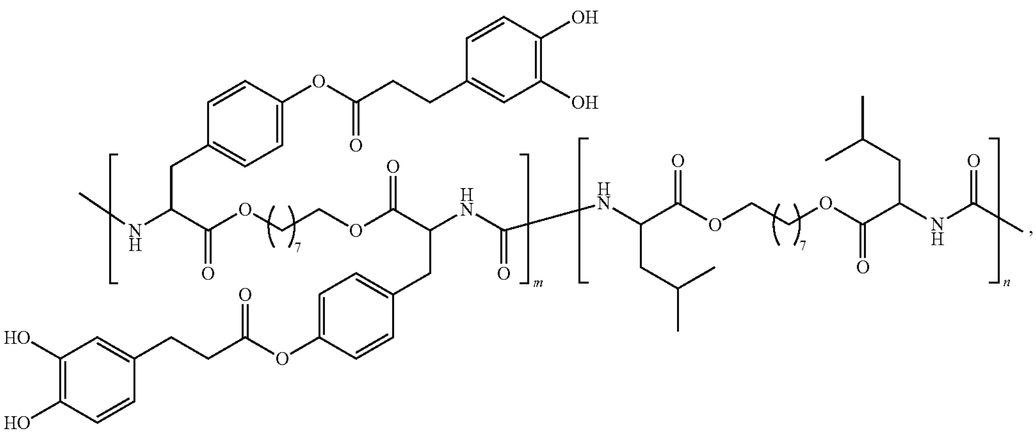
, and

-continued

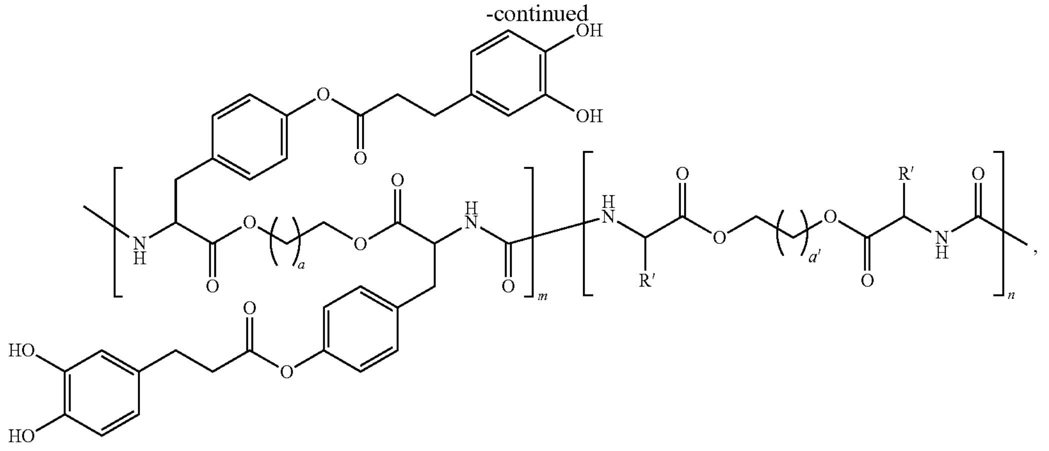

wherein R' is —$CH_3$, —$(CH_2)_3NHC(NH_2)C$═NH, —$CH_2CONH_2$, —$CH_2COOH$, —$CH_2SH$, —$(CH_2)_2COOH$, —$(CH_2)_2CONH_2$, —$NH_2$, —$CH_2C$═CH—N═CH—NH, —$CH(CH_3)CH_2CH_3$, —$CH_2CH(CH_3)_2$, —$(CH_2)_4NH_2$, —$(CH_2)_2SCH_3$, —$CH_2Ph$, —$CH_2OH$, —$CH(OH)CH_3$, —$CH_2$—C═CH—NH-Ph, —$CH_2$-Ph-OH, or —CH$(CH_3)_2$; a and a' are each integers from 1 to 20; b is an integer from 1 to 6; m is a mole fraction from 0.01 to 0.30; and n is a mole fraction from 0.70 to 0.99.

12. The biodegradable tissue adhesive of claim 1 further comprising an oxidative cross linker.

13. A method for making the biodegradable tissue adhesive of claim 1 comprising:

A. preparing a first counter-ion protected polyester monomer, wherein said first counter-ion protected polyester monomer comprises two benzyl protected tyrosine residues separated by from 2 to 20 carbon atoms;

B. preparing a second counter-ion protected polyester monomer, wherein said second counter-ion protected polyester monomer comprises two amino acid residues separated by from 2 to 20 carbon atoms;

C. reacting said first counter-ion protected polyester monomer and second counter-ion protected polyester monomer with a poly(ester urea) forming compound to form a first amino acid-based poly(ester urea) intermediate having a first segment comprising the residue of said first counter-ion protected polyester monomer and a second segment comprising the residue of said second counter-ion protected polyester monomer;

D. removing the protecting benzyl groups from the tyrosine residues of said first segment of said first amino acid-based poly(ester urea) intermediate to form a tyrosine-based poly(ester urea) adhesive;

E. preparing a carboxyl functionalized protected catechol compound, said carboxyl functionalized protected catechol compound comprising a protected catechol group and a carboxyl group;

F. reacting said carboxyl functionalized protected catechol compound with the hydroxyl groups of the tyrosine-based poly(ester urea) adhesive, thereby coupling said protected catechol group to said tyrosine-based poly(ester urea) adhesive to form a second amino acid-based poly(ester urea) intermediate having one or more protected catechol groups; and G. deprotecting the one or more protected catechol groups on said second poly(ester urea) intermediate to produce a degradable amino acid-based poly(ester urea) tissue adhesive having catechol functional groups.

14. The method of claim 13 wherein one or both of said first counter-ion protected polyester monomer and said second counter-ion protected polyester monomer are branched.

15. The method of claim 13 wherein, said second counter-ion protected polyester monomer comprises the residues of two amino acids selected from the group consisting of alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), serine (ser—S), threonine (thr—T), tryptophan (trp—W), tyrosine (tyr—Y), valine (val—V), benzyl protected tyrosine, BOC protected tyrosine and combinations thereof, and said two amino acids are separated by from 2 to 20 carbon atoms.

16. The method of claim 13 wherein, the molar ratio of said first counter-ion protected polyester monomer to said second counter-ion protected counter-ion protected polyester monomer is from about 1:20 to about 1:10.

17. The method of claim 13 wherein said carboxyl functionalized protected catechol compound comprises 2,2-dimethyl-1,3-benzodioxole-5-propanoic acid.

18. The method of claim 13 wherein, said first amino acid-based poly(ester urea) intermediate has the formula:

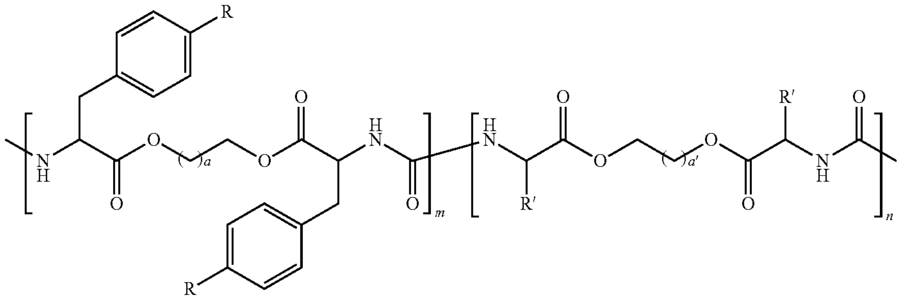

wherein R is —$OCH_2$-Ph or —$OCOOC(CH_3)_3$; R' is —$CH_3$, —$(CH_2)_3NHC(NH_2)C{=}NH$, —$CH_2CONH_2$, —$CH_2COOH$, —$CH_2SH$, —$(CH_2)_2COOH$, —$(CH_2)_2CONH_2$, —$NH_2$, —$CH_2C{=}CH—N{=}CH—NH$, —$CH(CH_3)CH_2CH_3$, —$CH_2CH(CH_3)_2$, —$(CH_2)_4NH_2$, —$(CH_2)_2SCH_3$, —$CH_2Ph$, —$CH_2OOH$, —$CH(OH)CH_3$, —$CH_2$—$C{=}CH$—NH-Ph, —$CH_2$-Ph-OH, or —$CH(CH_3)_2$; a and a' are each an integer from about 1 to about 20; and m and n are mole fractions.

19. The method of claim 13 wherein, said second amino acid-based poly(ester urea) intermediate has the formula:

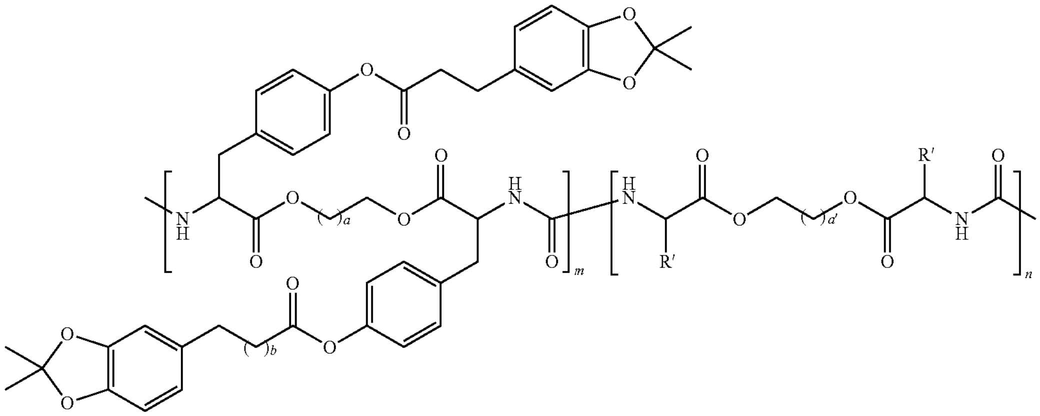

wherein R' is —$CH_3$, —$(CH_2)_3NHC(NH_2)C{=}NH$, —$CH_2CONH_2$, —$CH_2COOH$, —$CH_2SH$, —$(CH_2)_2COOH$, —$(CH_2)_2CONH_2$, —$NH_2$, —$CH_2C{=}CH—N{=}CH—NH$, —$CH(CH_3)CH_2CH_3$, —$CH_2CH(CH_3)_2$, —$(CH_2)_4NH_2$, —$(CH_2)_2SCH_3$, —$CH_2Ph$, —$CH_2OH$, —$CH(OH)CH_3$, —$CH_2$—$C{=}CH$—NH-Ph, —$CH_2$-Ph-OH, or —$CH(CH_3)_2$; a and a' are each an integer from about 1 to about 20; each b is an integer from 1 to 6; and m and n are mole fractions.

20. The biodegradable tissue adhesive of claim 6 wherein said one or more first monomer segments comprise from about 0.01 mole percent to about 0.30 mole percent of the amino acid-based poly(ester urea) copolymer.

21. The biodegradable tissue adhesive of claim 6 having the formula:

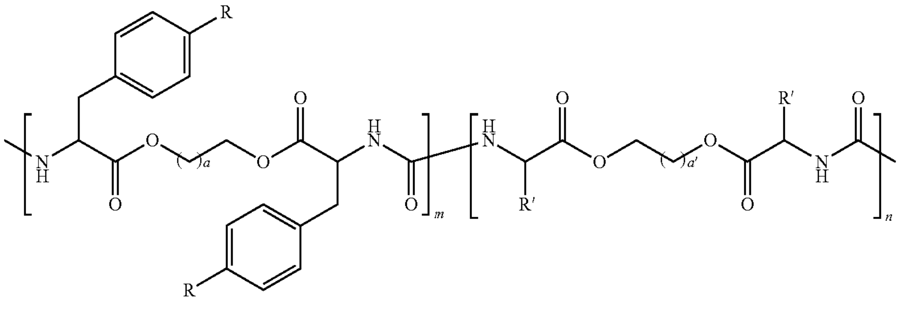

wherein R is —$OCOO(CH_2)_2C_6H_3(OH)_2$, —$OCOO(CH_2)_2C_6H_3(OH)_2$, —$OCOO(CH_2)_3C_6H_3(OH)_2$, —$OCOO(CH_2)_4C_6H_3(OH)_2$, —$OCOO(CH_2)_5C_6H_3(OH)_2$, —$OCOO(CH_2)_6C_6H_3(OH)_2$, and —$OCOO(CH_2)_7C_6H_3(OH)_2$; R' is —$CH_3$, —$(CH_2)_3NHC(NH_2)C{=}NH$, —$CH_2CONH_2$, —$CH_2COOH$, —$CH_2SH$, —$(CH_2)_2COOH$, —$(CH_2)_2CONH_2$, —$NH_2$, —$CH_2C{=}CH$—$N{=}CH$—$NH$, —$CH(CH_3)CH_2CH_3$, —$CH_2CH(CH_3)_2$, —$(CH_2)_4NH_2$, —$(CH_2)_2SCH_3$, —$CH_2Ph$, —$CH_2OH$, —$CH(OH)CH_3$, —$CH_2$—$C{=}CH$—NH-Ph, —$CH_2$-Ph-OH, or —$CH(CH_3)_2$; a and a' are each an integer from about 1 to about 20; and m and n are mole fractions.

* * * * *